(12) United States Patent
Tachas

(10) Patent No.: US 7,501,400 B1
(45) Date of Patent: Mar. 10, 2009

(54) INHIBITION OF GASTRIC ACID PRODUCTION AND/OR SECRETION

(76) Inventor: George Tachas, 2 Clunes Street, Kingsbury, Victoria, 3083 (AU)

( * ) Notice: Subject to any disclaimer, the term of this patent is extended or adjusted under 35 U.S.C. 154(b) by 0 days.

(21) Appl. No.: 09/979,666

(22) PCT Filed: May 24, 2000

(86) PCT No.: PCT/AU00/00498

§ 371 (c)(1),
(2), (4) Date: Mar. 7, 2002

(87) PCT Pub. No.: WO00/71164

PCT Pub. Date: Nov. 30, 2000

(30) Foreign Application Priority Data

May 24, 2000 (AU) .................. PQ0510

(51) Int. Cl.
  *A06K 31/70* (2006.01)
  *C07H 21/04* (2006.01)
  *C12Q 1/68* (2006.01)
(52) U.S. Cl. .............. 514/44; 536/24.5; 435/6
(58) Field of Classification Search .......... 435/6; 514/44; 536/23.1, 24.5
See application file for complete search history.

(56) References Cited

U.S. PATENT DOCUMENTS

| 5,330,982 | A | * | 7/1994 | Tyers ............... 514/214.03 |
| 5,739,119 | A | * | 4/1998 | Galli et al. ............ 514/44 |
| 5,801,154 | A | * | 9/1998 | Baracchini et al. ......... 514/44 |
| 5,817,480 | A | * | 10/1998 | Murry et al. ............ 435/69.1 |
| 5,914,269 | A | * | 6/1999 | Bennett et al. ........... 435/375 |
| 5,998,148 | A | * | 12/1999 | Bennett et al. ........... 435/6 |
| 6,087,489 | A | * | 7/2000 | Dean ................ 536/24.5 |

FOREIGN PATENT DOCUMENTS

| WO | WO 95/20043 A | 7/1995 |
| WO | WO 95/21380 A | 8/1995 |
| WO | 98/32467 | 7/1998 |
| WO | 99/41375 | 8/1999 |

OTHER PUBLICATIONS

Agrawal et al. Molecular Medicine Today, 2000, vol. 6, p. 72-81.*
Opalinska et al. Nature Reviews Drug Discovery, 2002, vol. 1, p. 503-514.*
Jen et al. Stem Cells 2000, vol. 18, p. 307-319.*
Rao et al., NeuroReport 1995, vol. 6, pp. 2373-2377.*
Maeda et al. Journal of Biological Chemistry 1990, vol. 265, pp. 9027-9032.*
Rao et al, "Attenuation of gastrin-induced gastric acid secretion . . . ," *neuroreport*, vol. 6, No. 17, pp. 2373-2377 (1995).
Sachs, G., et al; "The Pharmacology of the Gastric Acid Pump: The $H^+$, $K^+$ ATPase[1,2]"; *Annu. Ref. Pharmacol. Toxicol.*; vol. 35; pp. 277-305 (1995).

* cited by examiner

*Primary Examiner*—Tracy Vivlemore
(74) *Attorney, Agent, or Firm*—Nixon & Vanderhye

(57) ABSTRACT

The present invention relates to methods for the treatment or prevention of gastric acid disturbances and for reducing the breakdown of acid sensitive agents in the gastrointestinal tract. The present invention also relates to a method for transfecting parietal cells in vivo. The present invention also relates to synthetic oligonucleotides which may be used in these methods.

13 Claims, 3 Drawing Sheets

3.31 +/- 0.89
1.57 +/- 0.40
1.63 +/- 0.28

1.46 +/- 0.18
1.88 +/- 0.07
2.99 +/- 0.99

2.36 +/- 0.88
0.84 +/- 0.29
0.86 +/- 0.32

4.62+/- 0.71
1.84+/- 0.32
1.83+/- 0.10

1.41+/- 0.07
1.80+/- 0.12
2.82+/- 0.27

3.22+/- 0.48
1.34+/- 0.37
0.74+/- 0.11

INHIBITION OF GASTRIC ACID PRODUCTION AND/OR SECRETION

This is a national stage application filed under 35 USC 371 based on International Application No. PCT/AU00/000498 filed May 24, 2000, and claims priority under 35 USC 119 of Australian Patent Application PQ 0510 filed May 24, 1999.

FIELD OF INVENTION

The present invention relates to methods for the treatment or prevention of gastric acid disturbances and for reducing the breakdown of acid sensitive agents in the gastrointestinal tract. The present invention also relates to a method for transfecting parietal cells in vivo. The present invention also relates to synthetic oligonucleotides which may be used in these methods.

BACKGROUND OF THE INVENTION

Gastric reflux, gastritis, dyspepsia, stomach ulcers, duodenal ulcers and other gastric acid disturbances affect more than one in 600 people. About 10% of the world's population have gastric or duodenal ulcers at some time in their lives. Disturbances such as gastritis, dyspepsia, 70% of stomach ulcers and 90% of duodenal ulcers are thought to be caused by the bacterium *Helicobacter pylori*. In other cases the causative agent of the ulcers is thought to be nonsteroid anti-inflammatory drugs (NSAIDs) or conditions leading to hypersecretion of gastric acid. Gastric reflux occurs when the muscular valve at the lower end of the oesophagus (i.e. the lower intraoesophageal sphincter) malfunctions, by transient relaxation, allowing acid from the stomach into the oesophagus. Chronic gastric reflux leads to high level exposure of the oesophagus to acid, and leads to complications known as gastrooesophageal reflux disease (GORD).

The treatment in gastric acid secretion disturbances involves reduction of gastric acid production and/or secretion. In gastric reflux a reduction in acid levels allows the healing of the oesophageal mucosa and then prophylaxis involves maintenance therapy to keep acid levels low and to thereby prevent recurrence. In the case of ulcers a reduction in acid levels allows the healing of the stomach or duodenal mucosa, and then prophylaxis involves maintenance therapy to keep acid levels low to thereby prevent damage recurring. If the causative agent of the ulcer is the bacterium *Helicobacter pylori*, the treatment involves a reduction of acid levels, which allows acid sensitive broad-spectrum antibiotics to be used to eradicate the bacterium and to cure the disease.

It is understood that gastric acid secretion is regulated by neuronal (acetylcholine), hormonal (gastrin) and paracrine (histamine:somatostatin) mechanisms. All the pathways converge on and modulate the activity of the gastric proton pump enzyme, $H^+,K(^+)$-ATPase of the parietal cell. Precise information on the mechanisms of pump activation and identification of specific receptor subtypes in this process has led to the development of drugs capable of inhibiting and modulating acid secretion for treatment and/or prophylaxis. These include competitive antagonists that interfere with acid stimulatory receptors (such as muscarinic M1-receptor antagonists and histamine H2-receptor antagonists e.g. famotidine, cimetidine, and ranitidine) as well as more potent non-competitive inhibitors of the gastric proton pump $H^+,K(^+)$-ATPase (e.g. omeprazole, pantoprazole, lansoprazole, and rabeprazole). It also includes prostaglandin E receptor agonists such as misoprastol. Where the causative agent of the ulcer or acid disturbance is the bacterium *Helicobacter pylori*, the introduction of anti-Helicobacter therapy using antibiotics in admixture with these gastric acid reducing agents has increased the number of options available for the treatment and management of the disease.

There are however, a number of problems with and limitations in using the above-identified antagonists (inhibitors) and agonists in treatment and maintenance therapy. For instance, agonists such as misoprastol and antagonists such as histamine H2 receptor antagonists, are often the first line drugs used in therapy and maintenance. However, such agents are not completely effective because they modulate or interfere with only one of the pathways leading to acid secretion. They are slow in the treatment of the disease and it has been found that the relapse rates in maintenance therapy are high.

Further, because the effectiveness of such agents in some treatments is for a short time they are often taken a number of times per day and thus there is usually a lower compliance rate compared with drugs taken once a day or less often. Furthermore, because these agents cause adverse side-effects, lower doses, which are less effective, are commonly used. Finally, it has been found that these agents interact with cytochrome P450. Thus these agents cannot be taken in conjunction with other drugs such as diazepam, pyrethrin, and/or warfarin in multiple therapies.

Proton pump antagonists, the second line drugs, have become the more preferred agents in treatment and maintenance therapy because they are more effective than misoprastol and histamine H2 receptor antagonists. Proton pump antagonists are generally thought to be effective when taken once a day although recently it has been estimated that up to 40% of gastric reflux patients take them twice a day. Surprisingly, standard dosage, whether it is taken once or twice a day, does not reduce and maintain acid levels at the required therapeutic level throughout an entire day. Recent reports suggest that 15% and speculated up to 40% of gastric reflux patients that take standard doses twice a day still do not have sufficient effect at night. This can cause discomfort, a relapse of gastric reflux and other disturbances. Moreover, when higher doses or multiple standard doses are necessary for the desired effect to be achieved, they may cause inacidity in the stomach over extended periods of time. This inacidity has been found to cause hypergastrinaemia which can lead to G-cell abnormalities, ECL hyperplasia or other abnormalities in humans. Long term use of proton pump antagonists has also been linked with colon cancer. Surprisingly, it has recently being found that some conditions are refractory to treatment with the current proton pump inhibitor drugs. This includes 6-8% of chronic ulcer sufferers and 5-15% of gastric reflux sufferers. Furthermore, like misoprastol and histamine H2 receptor antagonists, proton pump antagonists cannot be taken in conjunction with other drugs such as diazepam, pyrethrin, and/or warfarin in multiple therapies, because these agents interact with cytochrome P450.

The proton pump antagonists are also involved in *Helicobacter pylori* eradication therapy where complicated drug regimens are commonly employed. For instance, in some regimens the antagonists are taken twice a day together with multiple daily doses of two different antibiotics for one to two weeks. In other regimens the antagonists are taken for a further two weeks making a total of one month. Because of the complicated drug regimens and the adverse side effects, patient compliance has often been found to be a problem. Non-compliance results in ineffective eradication therapy where because the antagonists are not been taken in the correct dosage the gastric acid in the stomach is not reduced either sufficiently or quickly enough and for a long enough time to enable acid sensitive antibiotics to work. In fact various reports suggest that conservatively about 15% or more of patients undergoing *Helicobacter pylori* eradication therapy are not cured for this very reason.

It is therefore an object of the present invention to provide acid reducing products and processes for using such products where one or more of the above problems and limitations are ameliorated.

SUMMARY OF THE INVENTION

In a first aspect the present invention provides a method for the treatment or prophylaxis of a gastric acid disturbance in a subject which method comprises administering to a subject in need thereof an effective amount of an oligonucleotide capable of modulating the activity of a target polypeptide involved in gastric acid production or secretion.

The present invention also provides the use of an effective amount of an oligonucleotide capable of modulating the activity of a target polypeptide involved in gastric acid production or secretion in the preparation of a medicament for the treatment or prophylaxis of a gastric acid disturbance.

In a second aspect the present invention provides a method of reducing the breakdown of an acid sensitive agent in the gastrointestinal tract of a subject which method comprises administering to a subject in need thereof an oligonucleotide capable of substantially modulating the activity of a target polypeptide involved in gastric acid production or secretion.

In a preferred embodiment of the second aspect, the acid sensitive agent is selected from the group consisting of an oral medicament, a synthetic oligonucleotide and an antibiotic.

In a third aspect the present invention provides a method of transfecting a parietal cell in vivo which method comprises administering orally to a subject a formulation comprising an oligonucleotide and a pharmacologically acceptable carrier.

In a fourth aspect the present invention provides a synthetic or isolated oligonucleotide capable of modulating the activity of a target polypeptide involved in gastric acid production or secretion.

In a fifth aspect the present invention provides a formulation comprising a synthetic or isolated oligonucleotide according to the fourth aspect and a pharmaceutically acceptable carrier.

In a preferred embodiment of the present invention, the target polypeptide is the histamine H2 receptor or a polypeptide which forms part of the gastric proton pump. Preferably, the target polypeptide is the alpha chain of the gastric proton pump.

In a further preferred embodiment, the oligonucleotide is capable of substantially interfering with the synthesis of the target polypeptide. Preferably, the synthetic oligonucleotide is capable of hybridizing to a polynucleotide involved in production of the alpha chain of the gastric proton pump.

The oligonucleotide may be capable of hybridizing to a region on an mRNA or pre-mRNA transcript encoding the alpha chain of the gastric proton pump, wherein the region is selected from the group consisting of:
(a) a region involved in translation initiation;
(b) a region involved in ribosome attachment to the transcript;
(c) a 5' untranslated region;
(d) a region encompassing an exon-intron boundary;
(e) a coding region; and
(f) a 3' untranslated region.

In one embodiment, the oligonucleotide is capable of hybridizing to a region on an mRNA or pre-mRNA transcript encoding the alpha chain of the gastric proton pump which is involved in translation initiation.

In another embodiment, the oligonucleotide is capable of hybridizing to a region on an mRNA or pre-mRNA transcript encoding the alpha chain of the gastric proton pump encompassing exon-intron boundary no. 1.

In yet another embodiment, the oligonucleotide is capable of hybridizing to a region on an mRNA or pre-mRNA transcript encoding the alpha chain of the gastric proton pump encompassing the sequence corresponding to bases 2396-2419 of the human coding region or part thereof.

In a further preferred embodiment, the oligonucleotide is up to 30 nucleotides in length comprising at least a seven nucleotide portion of a sequence selected from the group consisting of:

AA(T/U) (T/U)CA (T/U)AA (T/U)(T/U)C (T/U)CC (T/U)(T/U)C CCC A(T/U) (SEQ ID NO:1);

A G(T/U)G A(T/U)A (T/U)AG A(T/U)A AGG (T/U)AG GG (T/U)G(T/U) (SEQ ID NO:2);

(T/U) CA(T/U) AG(T/U) (T/U)C(T/U) CGG CC (T/U)(T/U)C CCC A(T/U) (SEQ ID NO:3);

and

G G(T/U)G A(T/U)G (T/U)AG A(T/U)G AGG (T/U)AG GG (T/U)G(T/U) (SEQ ID NO:4).

In yet a further preferred embodiment, the oligonucleotide has a sequence selected from the group consisting of:

AAU UCA TAA TTC TCC TTC CCC AU (SEQ ID NO:5);
GUG ATA TAG ATA AGG TAG GG UGU (SEQ ID NO:6);
U CAU AGT TCT CGG CC TTC CCC AU (SEQ ID NO:7);
U CAU AGT TCT CGG CC UUC CCC AU (SEQ ID NO:8);
U CAU AGU UCU CGG CC UUC CCC AU (SEQ ID NO:9);
CAU AGU TCT CGG CCT TCC CCA U (SEQ ID NO:10);
CAU AGT TCT CGG CCU UCC CCA U (SEQ ID NO:11);
CAT AGT TCT CGG CCT TCC CCA T (SEQ ID NO:12);
CAT AGT TCT CGG CCT TCC CCA TG (SEQ ID NO:13);
CAT AGT TCT CGG CCT TCC CCA TGG (SEQ ID NO:14);
CAT AGT TCT CGG CCT TCC CCA TGGT (SEQ ID NO:15);
GUG AUG TAG ATG AGG UAG GG (SEQ ID NO:16);
CA(T/U) AG(T/U) (T/U)C(TU) C GGC C(T/U)(T/U) CCC CA(T/U) (SEQ ID NO:17);
CA(T/U) AG(T/U) (T/U)C(T/U) C GGC C(T/U)(T/U) CCC C (SEQ ID NO:18);
CA(T/U) AG(T/U) (T/U)C(T/U) C GGC C(T/U)(T/U) CC (SEQ ID NO:19);
CA(T/U) AG(T/U) (T/U)C(T/U) C GGC C(T/U) (SEQ ID NO:20); and
CA(T/U) AG(T/U) (T/U)C(T/U) C GGC C (SEQ ID NO:21).

In a further preferred embodiment, the oligonucleotide comprises at least one modified internucleoside linkage. Preferably, the modified internucleoside linkage is a phosphorothioate linkage.

In a further preferred embodiment, the oligonucleotide comprises at least one modified sugar moiety. Preferably, the modified sugar moiety is selected from the group consisting of a 2'-O-propyl sugar moiety, a 2'-O-alkyl sugar moiety, a 2'-O-aminopropyl sugar moiety, a 2'-O-methyl sugar moiety (also known as 2'methoxy), a 2'-O-methoxyethyl sugar moiety (also known as 2'-O-(2-methoxyethyl) or 2'-methoxyethoxy) or a 2'-allyl sugar moiety.

In a further preferred embodiment, the oligonucleotide comprises at least one modified nucleobase. The modified nucleobase may be a 5-methylcytosine.

In a further preferred embodiment, the oligonucleotide is a chimeric oligonucleotide. Preferably, the oligonucleotide comprises at least four modified sugar moieties at either end. Preferably, the at least four modified sugar moieties at either end are selected from the group consisting of 2'-O-methyl moieties, 2'-O-methoxyethyl moieties, 2'-allyl moieties and combinations thereof.

In a further preferred embodiment, the oligonucleotide is capable of invoking RNase H activity.

In a further preferred embodiment, the oligonucleotide is conjugated to a delivery agent. Preferably, the delivery agent is selected from the group consisting of $K^+$ ions, gastric proton pump inhibitors and agents which bind to parietal cell surface receptors. The parietal cell surface receptors may be selected from the group consisting of histamine H2 receptors, acetylcholine receptors, gastrin receptors and somatostatin receptors.

In a preferred embodiment of the first and second aspects of the present invention, the oligonucleotide is administered orally.

In a further preferred embodiment of the first and second aspects, the effective amount is administered at a dosing frequency of once a day.

In a further preferred embodiment of the first and second aspects, the effective amount is administered at a dosing frequency of once every 4 to 7 days, or alternatively at a dosing frequency of less than once every 7 days.

In a further preferred embodiment of the first and second aspects, the oligonucleotide is administered in conjunction with an acid neutralizing agent or an agent which interferes with the production or secretion of acid. The acid neutralizing agent may be an antacid. The agent which interferes with the production or secretion of acid is selected from the group consisting of a muscarinic M1 receptor antagonist, a histamine H2 receptor antagonist, a prostaglandin E receptor agonist and an inhibitor of the gastric proton pump.

In a preferred embodiment of the fifth aspect, the formulation further comprises a stabilizer or an absorption enhancer.

In a further preferred embodiment of the fifth aspect, the formulation further comprises an acid neutralizing agent or an agent which interferes with the production or secretion of acid. The acid neutralizing agent may be an antacid. The agent which interferes with the production or secretion of acid may be selected from the group consisting of a muscarinic M1 receptor antagonist, a histamine H2 receptor antagonist, a prostaglandin E receptor agonist and an inhibitor of the gastric proton pump.

In yet a further preferred embodiment of the fifth aspect, the formulation is in liquid form.

In yet a further preferred embodiment of the fifth aspect, the formulation is in tablet form.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

DESCRIPTION OF THE INVENTION

As used herein the term "oligonucleotide" refers to an oligomer or polymer molecule of ribonucleic acid (RNA) or deoxynucleic acid (DNA) or mimetics thereof. The oligonucleotide may be single or double stranded, linear or covalently closed or circular in form. Preferably the oligonucleotide functions as an antisense; a ribozyme; an oligozyme; or an antigene and/or a like agent which is sufficiently complementary at the nucleotide level. i.e. hybridizes sufficiently well and with sufficient specificity, to achieve the desired result. Alternatively it may be an aptamer oligonucleotide which is sufficiently capable of binding to the target at the protein or other level to achieve the desired effect.

As used herein the phrase "capable of modulating" the activity of a target polypeptide or protein means that the oligonucleotide is capable of regulating a polypeptide or protein function up or down to achieve the desired effect. The oligonucleotide may be complementary to or capable of binding to the nucleotide sequence of a message and/or gene of the target polypeptide or protein for instance to the promoter or other regulatory parts of the gene or message. Alternatively it may be an aptamer oligonucleotide which is sufficiently capable of binding to the target at the protein or other level to achieve the desired effect.

As used herein the phrase "capable of substantially interfering with" the synthesis of a target polypeptide or protein means that the oligonucleotide is complementary to or is capable of binding to the nucleotide sequence of a message and/or gene of the target polypeptide or protein such that it interferes with the polypeptide or protein synthesis and thereby the polypeptide or protein function to achieve the desired effect.

As used herein the phrase "administering to a subject" encompasses any suitable mode of administration of the oligonucleotide. For example, the mode of administration may be oral; parenteral; topical; pulmonary, e.g. by inhalation or insufflation of powders or aerosols; intratracheal; intranasal; epidermal or transdermal. The phrase also encompasses introducing the oligonucleotide via a gene or cDNA or cRNA construct expressed in the target cell or other site in vivo.

One advantage of the present invention is the potential for effective dosing of about once a day, more preferably about once every 4 days to 1 week in humans, or less frequently than once a week. The potential for such effective low frequency dosing was not previously known to be possible in the treatment and/or prophylaxis and/or diagnosis of gastric reflux, gastritis, dyspepsia and stomach and duodenal ulcers, and other gastric acid secretion disturbances. It will be appreciated that such a low frequency of dosing may improve efficacy, improve compliance, avoid hypergastrinaemia, and/or G-cell abnormalities and/or ECL hyperplasia and/or other associated problems often observed with current treatments for gastric acid disturbances. Other advantages of the present invention is the potential to provide efficacy in gastric acid disturbances that are refractive to current treatments.

It will be appreciated that the oligonucleotides of this invention may be useful in process other than gastric acid disturbances in which the same or similar protein at the nucleotide level is involved. For example, some oligonucleotides of the present invention may be useful in the treatment of asthma and pernicious anaemia.

It will also be appreciated that the present invention provides a method of transfecting a parietal cell in vivo, which method can deliver any oligonucleotide administered orally to a parietal cell in the treatment of gastric acid disturbances or other diseases.

The Target Protein

The target protein may be any protein such as an extracellular molecule, a cell surface protein, cytoplasmic protein or a nuclear protein. This protein may have any function and may be a regulatory protein that bind the regulatory portions of DNA or RNA molecule, a structural protein, an enzyme, or any other protein function. The target protein may be the receptor for acetylcholine, gastrin, or prostaglandin E receptor or preferably histamine (histamine H2 receptor). Preferably, the target protein is the gastric proton pump, more preferably the alpha chain of the gastric proton pump protein. When seeking long action, a target protein expressed by the parietal cell is preferred.

The Oligonucleotide

In the context of this invention, the term "oligonucleotide" refers to an oligomer or polymer of ribonucleic acid (RNA) or deoxyribonucleic acid (DNA) or mimetics thereof. This term includes oligonucleotides composed of naturally-occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases.

While antisense oligonucleotides are a preferred form of antisense compound, the present invention comprehends other oligomeric compounds, including but not limited to oligonucleotide mimetics such as are described below. The antisense compounds in accordance with this invention preferably comprise from about 7 to about 30 nucleobases (i.e. from about 7 to about 30 linked nucleosides). Particularly preferred antisense compounds are antisense oligonucleotides, even more preferably those comprising from about 12 to about 25 nucleobases.

Specific examples of preferred antisense compounds useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Preferred modified oligonucleotide backbones that retain a phosphorus atom include, for example, phosphorothioates, chiral phosphorothioates, phosphorodithioates, phosphotriesters, aminoalkylphosphotriesters, methyl and other alkyl phosphonates. Various salts, mixed salts and free acid forms are also included.

Preferred modified oligonucleotide backbones that do not include a phosphorus atom include those having morpholino linkages formed in part from the sugar portion of the nucleoside. In other preferred oligonucleotide mimetics, both the sugar and internucleoside linkage of the nucleoside units are replaced with novel groups. One such oligomeric compound is referred to as a peptide nucleic acid (PNA).

Most preferred are oligonucleotides with phosphorothioate backbones, morpholino phosphorodiamidates backbones, and peptide nucleic acid backbones.

Modified nucleosides may also contain one or more sugar moieties. Preferred modifications include 2'-O-methyl sugar moiety (also known as 2'methoxy), a 2'-O-methoxyethyl sugar moiety (also known as 2'-O-(2-methoxyethyl) or 2'-methoxyethoxy) or a 2'-allyl sugar moiety.

Oligonucleotides may also include natural (unmodified) and modified nucleobases. Preferred modified nucleobases include 5-methylcytosine, 5-propynyluracil and 5-propynylcytosine.

It is not necessary for all positions in a given compound to be uniformly modified, and in fact more than one of the aforementioned modifications may be incorporated in a single compound or even at a single nucleoside within an oligonucleotide. The present invention also includes antisense compounds which are chimeric compounds. "Chimeric" antisense compounds or "chimeras", in the context of this invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art.

Chimeric antisense compounds of the invention may be formed as composite structures of two or more oligonucleotides, modified oligonucleotides, oligonucleosides and/or oligonucleotide mimetics as described above. Such compounds have also been referred to in the art as hybrids or gapmers or mixed oligonucleotide-oligonucleosides. The gap segment may be positioned between the 5' and 3' end wing, or located either at the 3' or 5' terminus (also known as hemimers or wingmers).

Another modification of the oligonucleotides of the invention involve chemically linking to the oligonucleotide one or more moieties or conjugates which enhance the activity, cellular distribution or cellular uptake of the oligonucleotide. Such moieties include but are not limited to lipid moieties such as a cholesterol moiety, cholic acid, a thioether, a thiocholesterol, an aliphatic chain, a phospholipid, a polyamine or a polyethylene glycol chain or adamantane acetic acid, a palmityl moiety or an octadecylamine or hexylamino-carbonyl oxycholesterol moiety.

The oligonucleotide also encompases any pharmaceutically acceptable salts. Preferred salts include salts formed with cations such as potassium, ammonium, magnesium or salts formed with anions such as carbonates or hydrogen carbonates.

Examples of modified oligonucleotides and pharmaceutically acceptable salts which are encompassed by the present invention are disclosed in U.S. Pat. No. 6,037,176, the entire contents of which are incorporated herein by reference.

The oligonucleotides of the present invention may be antisense, ribozyme, oligozyme, or antigene or like agents that preferably work at the nucleotide level i.e DNA or RNA levels. The function of DNA to be interfered with includes transcription. The function of RNA to be interfered with includes splicing of the RNA, translocation of RNA, translation of protein from the RNA, or RNA stability may be affected. The oligonucleotide may act in one or more ways which include but is not limited to (i) binding or competing with binding to the 5' regulatory region of the DNA and RNA molecules to decrease the rate of transcription and translation respectively; (ii) binding to the 5' untranslated region of the mRNA molecule, such as the cap site and affecting ribosome binding; or affecting unwinding of secondary structures therein; or binding about the first few nucleotides of the coding region and thereby interfering with ribosome binding; (iii) binding to the coding or 3' untranslated region of the mRNA molecule and affecting stability and half life of the mRNA, perhaps by a mechanism involving enzymatic cleavage such as cellular Rnase H or Rnase L for antisense oligonucleotides, or cellular Rnase P for oligozymes, or RNA enzymatic action of ribozymes; or (iv) binding to coding regions strongly enough so as to interfere with continuation of mRNA translation by affecting ribosome translocation, or (v) by interfering with processing of the pre-message to remove introns or to add to the CAP site or to modify polyadenylation at the 3' end or affect movement from the nucleus to the cytoplasm. It will be understood that this is not a comprehensive list.

In a preferred aspect the oligonucleotide has sufficient stability so that it has an extended period of action e.g. at least one day in humans. In a more preferred aspect the oligonucleotide is sufficiently stable in the acid environment of the gut so that it can be either administered orally and/or absorbed intact.

The oligonucleotide may also be admixed, encapsulated, conjugated, or otherwise associated with other molecules such as liposomes, receptor targeted molecules, oral, topical or other formulations for assisting in uptake, distribution, and/or absorption as described in the prior art and in U.S. Pat. No. 6,037,176.

The Nucleotide Sequences of the Target Protein

An antisense, ribozyme, oligozyme, and antigene or like agent is usually made complementary or capable of binding to the nucleotide sequence of a message and/or gene of the target protein as described in the next section below. It may have similar features to a positive regulatory or negative regulatory protein or factor, to interfere with it binding to the promoter or other regulatory parts of genes or message.

The gene and message and protein sequences of the target protein or target positive or negative regulatory protein or factor are made available through scientific or patent literature, the human genome project or other projects. Nucleic Acids (DNA and RNA) public databases contain the complete (known) nucleotide sequence of the human genome and those of selected model organisms. Four major public databases now store nucleotide sequences: GenBank and Genome Sequence DataBase (GSDB) in the United States, European Molecular Biology Laboratory (EMBL) Nucleotide Sequence Database in the United Kingdom, and the DNA Data Bank of Japan (DDBJ). The databases collaborate to share sequences, which are compiled from direct author submissions and journal scans. The four databases now house a total of almost 200 Mb of sequence. Although human sequences predominate, more than 8000 species are represented. These species include mouse, rat, rabbit, dog, pig, and primate species. It is expected the whole human genome will be known in the next 5 years which alone comprises 1000 Mb of sequence. The importance of the various components of the genome to gastric acid production and secretion, and its reduction, will then be unraveled in due course.

Hybridization of Therapeutic-Prophylactic Oligonucleotides to Target Nucleotide Sequence An antisense, ribozyme, oligozyme, and antigene or like agent when acting via the duplex approach form complementary base pairs, usually A:T(U) and G:C Watson Crick base pairs and Hoogsteen base pairs in triplex formation such as G.G:A, A.A:T, T.A:T or C.G:C or T.C:G. Other pairings and triplexes also occur.

For specificity of such oligonucleotide agents in human and animals 7 bases have been used but at least 9 base pairs in a row are preferred. For higher affinity usually longer base pairing is sought. A preferred agent is one that binds with high affinity (hybridization energy) to a region conserved in different members of the species. It preferably binds specifically to that message or gene and does not bind significantly to a similar sequence present in related messages or genes in the species.

There are a number of methods to getting an oligonucleotide drug specific to the nucleotide sequence of the target protein. Three methods a briefly described below.

Screening Libraries to Produce an Oligonucleotide Drug

Antisense, ribozymes, oligozymes, antigenes or like libraries: In the duplex approach, which usually relies on base pairing of G:C and A:T(U), it is possible to isolate antisense, ribozyme, oligozyme, antigene agents by screening libraries containing mixtures of all possible sequences randomly generated. Screening at high stringency using a target message or gene will allow for isolation of a highly specific agent. Testing in vitro it is possible to see the effect of the agent and the most active ones can be sequenced and then synthesized and tested in vivo for both high activity and high specificity.

Some of the "like agents", which rely on the sense approach: In the "sense" nucleic acid approach the gene promoter or message 5'regulatory sequence or other sequence, which will positively control synthesis i.e. lead to transcription or translation of the sequence of the target protein or its ligand, may be used to screen combinatorial (expression) libraries for oligonucleotide agents that bind to the sequences. This can be done at high stringency so that agents with high activity are isolated. Agents binding can then be tested in vitro and in vivo for activity and specificity wherein they compete with the target cells regulatory protein for binding to this regulatory site and thereby specifically interfere with transcription or translation of the target protein or its ligand.

The teachings of the present invention suggest at least one type library could be made with all possible combinations using the same or similar chemistry to the chemistry of the oligonucleotide used in Example 1 shown to reduce acid production or secretion. These may be best made on a gene chip for screening with a target nucleic acid.

Any oligonucleotide chemistry library could however be screened, and positives linked with the oligonucleotide used in Examples 1 or to an oligonucleotide with similar chemistry for delivery to the parietal cell.

Shotgun Synthesis to Produce an Oligonucleotide Drug

Oligonucleotide synthesizers are capable of making 150 different oligonucleotide sequences at one time. Thus, for about a 4 kb message such as the gastric proton pump alpha chain message, one may synthesize 150 25 nm er antisense oligonucleotides to cover the whole sequence end to end. For a more thorough approach 44 other antisense could also be made to work via interfering with 21 exon-intron splicing positions in the human gastric proton pump alpha chain mRNA, and/or 3 other splicing positions.

Of these 150-200 25 nm ers it would be expected that at least a few would work in vitro and/or in vivo if given the correct chemistry such as the chemistry of the oligonucleotide shown to work in Example 1. Shorter and longer derivatives of the oligonucleotides that work can then be tested to optimize the effect.

Similarly, one can also make all possible ribozymes to a target message. Knowing the triplets at which ribozymes cut, and identifying them in the target message, it is possible to make all the possible ribozymes that could cover the sequence end to end.

Similarly, antigene agents that work via the duplex or triplex methods can be made to all the target sequence in the region 5' to the 5'-untranslated region or any other region of the gene, and each one tested in vitro and in vivo.

Rational Design Computer Assisted Design and Knowhow to Produce Oligonucleotide Drugs Designing Antisense Oligonucleotides Knowhow combined with software packages allows one skilled in the art to determine the best antisense sequences in theory. In the antisense approach an oligonucleotide is rationally designed to be complementary to the specific message nucleotide sequence that codes for the protein, or to 5' or 3' untranslated sequences of the (pre)message or intron-exon boundaries of pre-mRNA. Some introns also have control sequences in them including ones for splicing.

There are different rules depending on the target site on the message and mechanism of action of the antisense. One approach is to target the initiation codon, where the antisense interferes with ribosome binding. The antisense that works this way may or may not target the initiation codon. Often around the AUG initiation codon there are regions with less secondary structure as can also be determined with some of the software packages, which are good target sites. Other targets sites on the message are the 5' untranslated region cap site, coding region or 3'untranslated region, in which latter two sites an antisense is preferably made of components that rely on the cellular RNAse H to degrade the message. In these latter two cases it may also be beneficial to target parts of the message which do not have significant secondary structure.

It will be understood that catalysis of target message may also occur by means of Rnase L and any other system that degrades message. Sequences on the mRNA and the antisense sequence and chemistry may be chosen to optimize formation of the relevant structures in each case.

Preferably the antisense agents are chosen to have no or low self ligating potential and no or low dimerization potential. Similarly, high duplex energy of hybridization of the antisense:mRNA is preferred. To enable the antisense to also work by overcoming the translocation energy of the ribosome, a particularly high duplex energy of hybridization is preferred.

Some of the rules for theoretically optimizing mRNA target and antisense design with regard to sequence effectiveness and specificity have being reviewed in the literature and is known to those in the art. It is not necessary to trial such a large number of molecules to identify one that works, particularly after being guided by knowing the chemistry of the oligonucleotide used in the present study to decrease acid secretion.

Designing Ribozymes

Some of the rules for theoretically optimizing ribozyme design with regard to sequence have being reviewed in the literature and is known to those in the art. They include parameters other than those referred to above for antisense.

For a catalytic oligonucleotide such as a ribozyme it is designed to be able to recognize and then degrade the target message. It has a nucleotide recognition sequence, to recognize the target message about the point where it can degrade the message and a catalytic unit for degrading the message. The catalysis may occur via a Uhlenheck hammerhead configuration formed after binding of the antisense RNA to the target substrate strand, or a Haseloff-Gerlach type hammerhead catalytic domain ribozyme, or a Hampel and Tritz hairpin catalytic domain ribozyme which is often more active under physiological conditions or other catalytic domain.

Once an effective ribozyme active agent is identified mutational changes can be used to optimize the catalytic effect.

Preferably the oligonucleotide sequence of the ribozyme is chosen so the catalytic unit can form, and to have no or low self ligating potential at the target recognition sequence, and no or low dimerization potential.

Catalysis using ribozymes may also occur by other means available to antisense such as via cellular RNase H or Rnase L if made using the appropriate reagents and/or interfering with ribosome translocation if there is a high enough melting temperature.

Designing Oligozymes

Some of the rules for theoretically optimizing oligozyme design with regard to sequence have being reviewed in the literature and is known to those in the art. They include parameters other than those referred to above for antisense.

Catalysis using oligozymes requires them to form tRNA structures with the target message so that cellular Rnase P degrades the message. Some report that the minimal substrate for human Rnase P consists of the 5'leader sequence, aminoacyl acceptor stem, T-Stem and T-loop of tRNA. And the D and anticodon stems and loops and the variable loop is replaced by a bulge, which can be as small as 1 nucleotide but preferably requires greater than 4 nucleotides, Nucleic Acids Symp Ser, (36):19-21 1997. Sequences on the mRNA and antisense are chosen to optimize formation of these structures.

Oligozymes may also work via other means such as cellular RNase H or Rnase L if made using the appropriate reagents and/or interfering with ribosome translocation if there is a high enough melting temperature.

Designing Antigenes

There are rational design methods using knowhow and software to design antigene drugs with the likely best sequences that form duplex and triplex structures with the target gene.

The triplex forming antigene agents may be made to the transcribed sequences, the intron-exon boundaries, or the 5' or 3' transcription regulatory sequences. Preferred target sites on the gene have a high purine AG content, but may also have some C, T content. One other target may be AT rich sequences. The target sites may be on one or both strands simultaneously.

The triplex forming agents may be CT, TG, or GA type triplex according to the known triplex codes and the known variations of the triplex codes. There are also know chemistries that allow one to minimize self folding of certain triplex forming oligonucleotide such as the GA type which advantage triplex formation. Certain triplex forming oligonucleotides offer potential long kinetics of action. Thus the antigene strategy is particularly advantageous when seeking a long acting drug.

The duplex forming antigene agents may also be made to bind specifically to single stranded regions of DNA in the gene known to occur when transcription or activation of transcription occurs. Preferred regions may be where RNA polymerases bind at promoters and to other regions involved in transcription regulation. In this case the antigene drugs form duplex DNA with the target gene in a way similar to antisense agents. Thus some of the same features as designing of antisense drugs may be preferred, i.e. no or low self ligating potential and no or low dimerization potential.

Other antigene agents may be chemicals and proteins or other biomolecules that bind to the target DNA sequence. These may be delivered to the parietal cell by linking to an oligonucleotide and transfecting to the parietal cell as described herein.

Choosing Sequence, Chemistry and Other Features of the Therapeutic-Prophylactic Oligo It is understood in the art that the oligonucleotide need not be 100% complementary to its target nucleic acid to be specifically hybridizable. An oligonucleotide is specifically hybridizable when binding to the target nucleic acid interferes with the normal function, and/or produces the desired effect. The antisense, ribozyme, oligozyme, or antigene agent is preferably fully complementary to and binds strongly and specifically to a target nucleotide sequence of the gene or message of the protein. If an antisense or ribozyme oligonucleotide is not fully complentary then one chemistry to improve the chances of working would be to include inosines which can bind any base or T or C5 propyne or methycytosine nucleobases, which latter three bases increase the affinity of the molecule at complementary bases. For antigene triplex forming agents there are abasic linkers and other modifications of nucleotides which are known in the art that also help in these situations. Preferably there is no or low non specific binding of the oligonucleotide to non-target sequences under physiological conditions.

Preferably the oligonucleotide agent has a chemistry that provides high affinity and high specificity to "oligonucleotide binding proteins and receptors" that may be useful for cellular distributions and uptake of oligonucleotide sequences to parietal cells. Certain antisense, ribozyme, oligozyme, or antigene agents will because of their chemistry be distributed and taken up by receptors that recognize the nucleotide derivative or analogue sidechains. Other distributions and uptake methods that are important may be active or passive. Choosing the correct chemistry to make the antisense, ribozyme, oligozyme, or antigene will improve this distribution, uptake, and the effectiveness of the oligonucleotide as is known in the art.

One such chemistry is the deoxynucleotide phosphorothioate nucleotides or 2'O modified forms as shown herein in the examples.

Preferably the agent has a chemistry that provides high efficacy relative to other chemistries and is safe.

Preferably the chemistry also allows the potential for survival in the acid environment of the stomach and thus administration via the oral route. This may enable absorption into the body via the stomach, the small or large intestine, and perhaps uptake directly by parietal cells from the gastric contents akin to topical application.

Preferably the agent has a chemistry that makes it stable in vivo with a long half life of about one day. In one preferred embodiment the chemistry provides a long to very long half life of a number of days in vivo that allows a frequency of dosing of about once every 4 days to a week or longer.

Described below are some of the chemistries that meet the above criteria for antisense, ribozyme, and antigene oligonucleotides and may allow delivery of naked oligonucleotide agents for gastric acid reduction. It will be understood however that many other chemistries can be used to make these oligonucleotide agents work to reduce gastric acid production or secretion, including providing them with other structures, formulations and/or by providing for their protected delivery.

Antisense Oligonucleotide

An antisense may be between 4-50 nucleotides or nucleotide equivalents, preferably between 7-30 nucleotides long and more preferably between 12 to about 25 nucleotides.

2' O methyl oligoribonucleotide phosphorothioates

As shown in the examples herein, a 23 nm er hybrid antisense oligonucleotide with four 2'-O-methyl oligoribonucleotide phosphorothioates at each of the 5' and 3' ends with an inside core of deoxynucleotide phosphorothioates has appropriate pharmacokinetics to reach stomach parietal cells when administered orally, and is sufficiently resistant to degradation in the acidic environment of the stomach to remain active. It is active in reducing acid output from stomach parietal cells for at least 4 days in the rat which suggests that it has a long half life in the stomach tissue and/or parietal cells.

Thus one antisense oligonucleotide chemistry that is suitable for gastric acid reduction comprises 2'-O-methyl oligoribonucleotide phosphorothioates. Such an antisense oligonucleotide may have two and more preferably four or more 2'-O-methyl oligoribonucleotide phosphorothioates at each of the 5' and 3' ends with an inside core of at least about 4 to 5 deoxynucleoside phosphorothioates when Rnase H is the method of action (i.e. hybrid antisense agent).

It will be understood by those skilled in the art that a suitable antisense may also comprise only 2'Omethyl oligoribonucleotide phosphorothioates, and/or only 1 to 3 deoxynucleoside phosphorothionates because antisense directed to the initiation site of the mRNA do not need to work via an RNase H method and thus do not need at least a 4 to 5 deoxynucleoside phosphorothioate inner core.

Such 2'Omethyl oligoribonucleotide phosphorothioates antisense have increased binding and lower toxicity, shorter distribution time relative to non-modified deoxynucleotide phosphorothioates. With a high enough melting temperature they can also be used to interfere with ribosome translocation in the coding region of the message.

Other 2' modifications of phosphorothioates that are suitable include 2'fluoro, 2'-O-propyl, 2'-O-alkyl, 2'-O-aminopropyl, 2'methoxyethoxy substitutions.

It is expected that a reverse hybrid antisense agents described in the art such as those comprising an inner core of 2'-O-methyl or related 2' modified oligoribonucleotide phosphorothioates and deoxynucleoside phosphorothioates on the outside will also work.

Moreover, oligonucleotides with deoxynucleotide phosphorothioates on at least one end should also work.

Deoxynucleotide Phosphorothioates

Deoxynucleoside phosphorothioate may also be an appropriate chemistry from which to make antisense oligonucleotides for gastric acid reduction. They comprised a part of the molecule shown herein in the examples to work in acid reduction via the oral route. They have been shown by others to have a long or very long half life varying between about 1 to 8 days, and the capacity to survive the acidic environment of the stomach. They do not tend to be absorbed intact via the duodenum into the body, but in the present system there is potential for direct uptake via the stomach from the gastric contents in which case there does not need to be absorption via the duodenum. It will also be understood by those skilled in the art that these agents can be administered by many alternative routes as naked agents. Also these agents may be assisted in absorption via the duodenum by packaging in liposomes, nanoparticles, and use of other formulations.

Other Antisense Chemistries and Formulations

It will be understood that phosphodiester, methylphosphonate, phosphorothioate, peptide nucleic acid, morpholino phosphorodiamidates, or any other antisense oligonucleotide chemistries, and hybrids of these are appropriate chemistries for an antisense oligonucleotide for use in gastric acid reduction. Even if the antisense agent does not inherently have the appropriate chemistry for delivery to the parietal cell by oral administration, it may be structurally modified or formulated for oral delivery or a different route of administration may be used.

Stabilizing Antisense-Chemical and Formulations Changes for Long Action

Many of the above identified chemistries such as those comprising a phosphorothioate backbone and 2'Omethyl modified bases, provide antisense drugs which have an inherently good level of stability. The above identified antisense chemistries and derivatives and analogues of these and other agents, may however, be further self stabilized to increase the half life of the drug. Phosphorothioates may be self stabilized at the 3' end with a loop, to increase its half life many fold. Similarly the 2'-O-methyl oligoribonucleotide phosphorothioates and the hybrid and reverse hybrid 2'-O-methyl agents may have their half life increased this way. Self stabilizing can also be used to increase specificity of a drug and its efficacy.

Increased stability may also be obtained via alpha-oligonucleotides. Stabilization factors up to 200 fold can be achieved for alpha-oligonucleotides over beta-oligonucleotides via making the last two residues . . . T-C, . . . A-C, or . . . C-C, and intermediate stabilization is found via . . . G-A, . . . T-A, or T-T terminal sequences. These agents may also be used as hybrids.

Increased stability can also be provided by using peptide nucleic acids, morpholinophosphorodiamidates and other highly nuclease resistant agents.

It is known in the art that purines, G or A may be stripped off the ends of oligonucleotide drugs in a highly acidic environment. This may be overcome by reducing residence time in the gastric contents, by administering oligonucleotide drugs in fed state or by providing formulations to further stabilize the antisense or like agents in the acidic environment of the stomach as is known in the art. Alternatively oligonucleotides with fewer susceptible purines may be chosen.

It is also known in the art that longer action may be obtained by encouraging aggregates. This may be done via including four G's which under non acidic conditions should form tetramer, and allow for slower release of antisense from the organs and/or cells.

Other modifications may be to alter the hydrophilicity or lipophilicity profile of the antisense drug to slow its release from the organ or cell.

Ribozymes and Like Catalytic Agents

Ribozymes and like catalytic agents may be made using any of the known chemistries known in the art. Formulations may be used to protect the ribozyme or like catalytic agents for delivery, in acid reduction as is known in the art. Preferably, however, as indicated above for antisense drugs, one may make a fully RNA ribozymes more nuclease and perhaps also acid resistant by using deoxynucleotide phosphorothioate ends or preferably a 2' modified oligoribonucleotide phosphorothioate ends. One may use at least two and perhaps four or more 2'-O-methyloligoribonucleotide phosphorothioates at both the 3' end and the 5' end where these ends are in the hybridizing arms. This is a similar chemistry to that used in the oligonucleotide drugs shown to work herein. One may also add 2' propyl or other 2' modifications to the sugar in the 5'and 3' ends keeping the central bases RNA.

One may also increase the nuclease and perhaps acid resistance by modifying the catalytic unit to comprise phosphorothioates or 2'Omethyl or other 2'modifications provided the nucleotides changes are in regions non essential for ribozyme activity. For a hammerhead ribozyme it is possible to modify all but about 4-6 non-contiguous nucleotide positions in the catalytic unit. Such stabilizing changes may be via 2'Omethyl oligoribonucleotide phosphorothioates provided they are not in regions essential for ribozyme activity.

Other efficacy improvements may be provided by using a 3' nucleotide cap or inverted thymidine as disclosed in the prior art J. Biol Chem 1995 Oct. 27; 270(43); 25702.

Affinity and nuclease resistance may be improved by any one or more of the alternative known improvements in chemistry or via other facilitators of activity. Some other improvements are described in WO95/06764 the contents of which are incorporated by this reference.

Antigene Oligonucleotides

An antigene agent may work by duplex formation and can thus be made using the same chemistries or combinations of chemistries referred to above for antisense drugs and shown herein to work in acid reduction i.e. deoxynucleoside and 2'Omethyl oligoribonucleoside phosphorothioates, methylphosphonates etc. The antigene agent may also work by triplex formation in which case the chemistry of the nucleotide chosen must be capable of triplex formation as is known in the art. When deoxynucleoside phosphorothioates are used preferably AG or AT triplex and perhaps GT triplex forming oligonucleotides are made. The CT triplex forming oligonucleotides can also be made with deoxynucleoside phosphorothioates but preferably one or other stereoisomers are used. The 2'-O-methyl oligoribonucleotide phosphorothioates or similar 2'-sugar modification chemistries form both duplex and triplexes and are thus also useful for triplex antigene agents for acid reduction.

Because antisense oligonucleotides with deoxynucleoside phosphorothioates and 2'Omethyl oligoribonucleotide phosphorothioates have been shown herein to be capable of gastric acid reduction when interfering with the message it is expected that they can also work effectively as antigene agents. This is because it is expected that antigene agents with this chemistry will have the required properties as naked DNA/RNA to reach the stomach parietal cells capable of acid production, and have oral bioavailability, increased nuclease resistance, and binding properties needed for acid reduction. They should also display a longer action. Antigene agents which form triplex bonds are expected to have the longest action, because of the increased half life of the bonding to the target. It will also be understood that effective antigene agents may vary in length depending on the type of antigene agent. Some triplex oligonucleotides types are preferably about 11mners, others about 15 nm ers, and others 20 nm ers. AG type triplex oligonucleotides may also need to be made longer to minimize self folding and/or to work more effectively.

Moreover, the antigene oligonucleotide may be self stabilized to increase its half life as is known in the art to increase the half life of antisense agents. Formulations may also be used to further stabilize the antigene or like agents as is known in the art and for delivery.

It will also be understood that depending on the nucleotide used, formulations may be needed to stabilize the antigene or like agents as is known in the art. Antigene agents made with any suitable chemistries will work. Modifications such as spermine and similar modified nucleotides, or deaza variants of nucleotides which may be more effective in triplex formation as is known to those in the art may be used.

Mixtures of Conventional Drugs and Novel Antisense, Ribozyme, Oligozyme, and Antigene and Like Drugs The present invention also relates to an antisense, ribozyme, oligozyme, antigene or like agent, used in mixtures with an antagonist or agonist which antagonist or agonist is capable of substantially interfering with the function or modulating the action of a target protein involved in the production or secretion of acid.

The Conventional Antagonist or Agonist

The conventional antagonist or agonist may be a partial agonist, or partial or complete antagonist or inhibitor when it enters the body or after it is modified in the body. It may bind to or compete with the protein target or a ligand of the protein target and it may do so before or after the target is modified in the body.

Some antagonists that reduce acid secretion target the proton pump and include omeprazole, lansoprazole, pantoprazole, rabeprazole, or derivatives or analogues of these.

Some antagonists that reduce acid secretion target the histamine H2 receptor and include famotidine, ranitidine, and cimetidine or derivatives or analogues of these agents.

One agonist that reduces acid secretion includes misoprastol, which targets the somatostatin prostaglandin E2 receptor.

The Mixtures

The antisense, ribozyme, oligozyme, or antigene or like molecule may target the same or different protein to that targeted by the antagonist or agonist. Preferably the protein that is targeted is the proton pump.

Administering Mixtures—Advantages in Treatment of Gastric Acid Disturbances

Using mixtures of an acid reducing antisense, ribozyme, oligozyme, antigene, or like drug and antagonist drugs according to the present technology is expected to produce a higher pH than can be achieved with the antagonist acid reducing drug used alone. This has potential advantages in the treatment of gastric acid disturbances such as improving eradication of Helicobacter, which are pH sensitive, and in ensuring the acid sensitive antibiotics remain more active, and in reducing acid levels more completely as required in hypersecretory conditions.

An acid reducing antagonist drug given in admixture with an acid reducing antisense or like oligonucleotide drug is also expected to increase the speed of acid reduction which may also have advantages in treatment and prophylaxis.

Conjugated Compounds for Improved Delivery and Improved Uptake-Action.

The present invention also relates to a conjugated compound comprising an antisense, ribozyme, oligozyme, antigene or like agent linked to a delivery agent for delivery to a target cell of interest. Preferably the target cell for delivery is the parietal cell.

The delivery agent linked to the antisense, ribozyme, oligozyme, or antigene drug may be $K^+$ ions, because these ions are actively taken up from the gastric contents via the gastric proton pump of the parietal cell, which in return secretes $H^+$ ions, that is acid.

Preferably, the delivery agent is an antagonist or agonist capable of substantially interfering with or modulating the function of a target protein involved in the production or secretion of acid.

One such target protein for delivery to parietal cells is the histamine H2 receptor in which case the antagonist may be famotidine, ranitidine, cimetidine. Other surface receptors for delivery to parietal cells include receptors for acetylcholine, gastrin and somatostatin.

Most preferably the antisense, ribozyme, oligozyme, antigene and like agents are linked to agents that allow them to be taken up by receptors and pumps that convey their contents to the cytoplasm of parietal cells before receptors fuse with lysosomes and are degraded. Thus targeting receptor that cycle through acidic compartments in the cytoplasm releasing their contents and returning to the cell surface are preferred.

Therapeutic-prophylactic oligonucleotide drugs according to the present invention may also be conjugated to agents that improve uptake by cells by non receptor mediated mechanisms. The oligonucleotides may be linked to fusogenic peptides or penetratin, transportan or other similar charged molecules or surfaces for uptake. Also agents that allow for release of the antisense from liposomes and/or delivery to appropriate compartments of cells may be conjugated to the antisense to provide for improved action.

Conjugating Procedures

The conjugation procedure will depend on the chemical nature of the agents to be joined. If one is a nucleotide and the other a peptide, there are known methods to join them as described in the International patent application US91/02224 by Gilead Science which is incorporated herein by way of reference only. Alternatively, one can use peptide nucleic acids as the backbone so the agents are connected by conventional peptide links.

$K^+$ ions can be joined to the negatively charged phosphate backbone of the antisense, ribozyme oligozyme or antigene or like drug. Alternatively they may be joined to other parts of the drug.

Chemicals such as ranitidine or famotidine can be joined to the bases, sugars, or phosphate groups of the nucleotide, derivatives or analogues of the antisynthesis agent.

Conjugated molecules can be joined such that they come apart once inside the cell according to the methods described by Meyer et al in U.S. Pat. No. 5,574,142, which is incorporated herein by way of reference.

Any conjugation procedure should preferably not interfere substantially with the ability of the bases to form complementary base pairs with the target message or gene.

Advantages of Administering Conjugates for Delivery

Conjugates such as famotidine+antisense to the proton pump, that may bind to histamine H2 receptors in the parietal cell can be used to improve delivery of the antisense drug to the parietal cell. This may increase the effective dose of an antisense drug acting on the parietal cell and decrease the dose needed for effect. With a decrease in dose there is potential for an increase in the therapeutic window (safety) and potential cost savings.

Conjugates such as famotidine+antisense to the proton pump or famotidine+antisense to the histamine H2 receptor, may also have a relatively quick immediate effect within minutes to hours because of the famotidine part. The famotidine effect alone does not last the whole day because of its relatively short half life. However, the longer action of the antisense part of the conjugate drug may ensure there is an effect for the whole day.

An antagonist—antisense etc conjugate (or mixtures) given by the oral route may also act quickly to decrease the fluxes around the parietal cells which may improve the probability of direct uptake of antisense drugs from the stomach contents. This may decrease the dose of drug effective in treatment and maintenance therapy increase therapeutic window and provide cost savings.

Joining the antagonist-antisense etc may also have other advantages over mixtures. It may overcome interactions between the agents by protecting interacting groups or by keeping interacting groups apart. It may also protect agents from interacting with P450.

An antisense agent linked to omeprazole that locates to the stomach and preferably parietal cells of interests, may also reduce acid secretion more quickly and completely, compared to either drug used alone as outlined in the mixture section.

Formulations

The present invention provides a formulation comprising an effective amount of at least one antisense, and/or ribozyme, and/or oligozyme, and/or antigene and/or like agent in admixture with a pharmaceutically acceptable carrier.

Such a formulation may be a liquid or tablet, and may comprise other stabilizers, and/or absorption penetrators, and/or enhancers, and/or delivery agents and/or other formulation agents as are known in the art. Preferably the formulation allows for oral administration.

One liquid formulation capable of oral administration comprises antisense, ribozyme, oligozyme, antigene or like agent with deoxynucleoside phosphorothioate bonds and at least one and more preferably at least four 2'-sugar modified oligoribonucleotides phosphorothioates on either one or both of the 5' and 3' ends. The 2' modifications of such an agent include 2'-O-propyl, 2'-O-alkyl, 2'-O— methoxyethyl and 2'-O-methyl substitutions.

Other formulations for administration via the oral route are described in WO9901579A1 and U.S. Pat. No. 5,869,246 the contents of which are both incorporated by this reference.

Preferred formulations provide greater gastric acid reducing affect either by protecting acid sensitive components of the oligonucleotide, by increasing the absorption through the stomach and/or small and/or large intestine, by providing improved delivery, to target cells, or by deviating the antisense drug away from organs where it may otherwise collect or be degraded.

For deviating the antisense away from certain organs the oligonucleotides may be co-administered with polyinosinic acid, dextran sulfate, polycytidic acid or other similar inert carriers.

Liposomes that are acid resistant may be used to protect acid sensitive oligonucleotide components and help target oligonucleotides specifically to parietal cells. For specific delivery the liposomes preferably have chemical agents or peptides to allow binding to target cells.

Formulations may also be used to increase length of action by providing slow and/or continuous release and/or sustained release as is known to those skilled in the formulation art. Oligonucleotide may for instance be packaged within nanoparticles to provide for sustained release over long periods.

Alternative Routes of Administration

Antisense, ribozymes, oligozymes, and antigene or like agents may be administered by any one of the known routes. The preferred route of administration depends on the type of oligonucleotide chemistry or its formulation and the target site. Administration routes for acid reduction can include the oral, intravenous, intraperitoneal, transdermal, intradermal, transcutaneous, and all other routes known in the art including inhalation.

Preferably administration is by the oral route because it is the most convenient route for self administration. Preferably administration by the oral route leads to absorption via the stomach, or small intestine or large intestine, and most preferably there is direct absorption by parietal cells from the gastric contents. Direct uptake of the oligonucleotide from stomach tissue or into parietal cells would decrease the dose required for treatment and thus increase the therapeutic window, and decrease costs associated with treatment.

Phosphorothioates can be administered by the oral, intravenous, intradermal, transdermal, subcutaneous, and other routes. They survive in the stomach after oral route administration for certain periods and under certain conditions. Thus, they may act unformulated in the stomach. Preferably they are formulated for protection against the acid environment, and also for improved uptake via the stomach. More preferably they are also formulated so as to survive intact following absorption via the small intestine.

Antisense and other like drugs containing 2'-O-methyl or other like 2' sugar modifications or hybrid drugs with at least two and preferably four or more 2'O methyl or other like 2' sugar oligoribonucleotide phosphorothioate modifications on either end, with or without deoxynucleoside phosphorothioate inner core, may also be administered by any of the routes described above. Preferably they are administered by the oral route because as shown herein in examples 1 administered this way they act to reduce parietal cell gastric acid production and/or secretion. These oligonucleotides are expected to remain intact longer in the stomach environment than phosphorothioates when unformulated and thus may act by direct uptake from the stomach contents. They may also be absorbed sufficiently intact via the small intestine and large intestine and may also act this way.

Formulation is expected to improve protection against the acid environment of the stomach and also improved uptake by stomach or the small and large intestine.

Increase Uptake Via the Oral Route

More preferably oral administration is modified to improve uptake of antisense and like drugs by absorption directly from stomach contents and most preferably by the parietal cells or other target cells of the stomach. This may be achieved in a number of ways.

One way that may be effective for more acid resistant oligonucleotides is by increasing resident time in the stomach and thereby increasing the probability of direct uptake. This can be done by reducing the volume of drug and/or liquid taken with it. This may also have the advantage of increasing absorption rates in the small intestine.

Alternatively, food, such as fatty foods, may be used to delay gastric emptying to increase time in contact with the target cells. The probability of direct uptake may also be increased as the stomach churns the food. This may provide the momentum for the agent to reach the target cell. However, the invention is not restricted to any particular mechanism.

For more acid sensitive oligonucleotides food, such as peptide foods may be used to buffer the gastric contents.

The other agents such as mucoadhesives known in the art may also be used to achieve increased uptake directly from the stomach contents. The lead antisense or other agent(s) may be formulated in any of the known methods for adhesion to the gastrointestinal tract, such as using mucoadhesives as described in U.S. Pat. No. 5,458,879 the contents of which are incorporated herein by way of reference, or other oral vehicle compositions.

They may also be introduced into liposomes for increased transfer into the target cells. Moreover targeting peptides or targeting chemicals may be placed on the surface of the liposomes which peptides or chemicals recognize target cell receptors. This may be used as an efficient way for improving (specific) cellular uptake.

Most preferably the antisense, ribozyme, and antigenes are linked to agents or introduced into liposomes with chemical agents that allow them to be taken up by receptors that convey their contents to the cytoplasm before receptors fuse with lysosomes and are degraded. Thus target receptors that cycle through acidic compartments in the cytoplasm releasing their contents and returning to the cell surface are preferred.

The antisense chemistry chosen may comprise phosphorothioates or may be of any other chemistry recognized by receptors for these agents as previously discussed.

Low phosphate diets may also be used to increase the absorption of antisense and other phosphate based agents into the body, likely to be via the normal route of the small intestine.

Using mixtures and may also assist with uptake via the oral route as previously described.

Other formulations known in the art may also be used to increase oral route uptake.

Ethanol or other agents that are absorbed directly from stomach contents may also be used to increase uptake of a linked antisense, oligozyme, ribozyme, or antigene drug.

Pharmacokinetics—the Unique Long Action of the Oligonucleotide Drugs Action of Conventional Proton Pump Inhibitor Drugs For treatment of gastric acid disturbances and maintenance therapy it is possible to target the gastric proton pump of the parietal cell. The gastric proton pump has a long half life of perhaps about 2 days, and there is slow turnover of new protein, with an activity half life of every 15 hours, possibly reflecting slow transcription and translation rates.

Omeprazole inhibits the alpha catalytic subunit by binding to it covalently. After oral administration the onset of the effect in human occurs within 1 hour, with the maximum effect occurring within 2 hours. At 24 hours because of new pump synthesis it is 50% of maximum and an effect is detectable up to 72 hours. This is because there is prolonged binding of the target enzyme. The inhibitory effect increases with repeated once-daily dosing reaching a plateau after 4 days. The antisecretory effect of the drug reflects its short plasma half life of approximately 60 minutes, the number of active pumps during that time and the recovery of pump activity following biosynthesis and reversal of inhibition (Sachs et al Ann Rev. Pharmacol Toxicol, 1995m 35:277-305.) When discontinued the secretory activity returns gradually, and is back to normal at 3 to 5 days via new pump synthesis.

Action of Oligonucleotide Drugs to the Proton Pump—a Lower Frequency of Dosing

Oligonucleotide drugs as shown herein in Example 1 experiments 1-3 and 6, have the potential to substantially interfere or modulate the production of acid in the treatment or prophylaxis of gastric acid disturbances when dosing at a frequency of about once a day, about once every 4 days to a week, or less often. The preliminary data shows an effect in the rat for 1 day and up to at least four days after oral administration. The long 4 day effect in the rat is not observed using 3.45 mg/kg omeprazole dosed once via the intraperitoneal route (Example 1 experiment 7). The acid reducing effect at day 4 with the antisense drug ARISA is similar to that produced with the drug omeprazole at 3.45 and 1.725 mg/kg when dosed 5 times over the same 4 days.

The antisense drug ARISA 1 is expected to show an acid reducing effect in the rat at even longer time points, perhaps when using the same and/or slightly higher doses yet to be tested. Longer effect in the rat is also expected to be achievable with variants of the ARISA 1 oligonucleotide drugs that are more stabilized and/or formulations that are more stabilized with agents used in the art.

A longer 4 days to a week effect, and longer than 1 week effect in humans is also expected. Metabolic rate differences between the human and rat, mean the acid reducing effect of drugs in the human are expected to be longer and occur at lower doses.

The present rat studies have shown for the first time the potential for a lower frequency of dosing in acid reduction to what is known in the prior art. The potential for such effective lower frequency of dosing in acid reduction was not previously known to be possible in the treatment and/or prophylaxis of gastric reflux, gastritis, dyspepsia and stomach and duodenal ulcers, and other gastric acid secretion disturbances. It will be understood by those skilled in the art that what is meant by a lower frequency of dosing to that used in the prior art depends on the disease-condition and severity of the disease-condition and the route of administration. It will also be understood that such a lower frequency of dosing in acid reduction may be achieved using oligonucleotide agents according to the different aspects of the present invention, or via other means such as formulation or delivery. The particularly long half life of parietal cells contributes to this expectation of a longer action been possible by a variety of means.

Longer Action and Lower Doses on a Per kg Basis of Omeprazole and Antisense Drugs in Humans Compared to the Rat As is generally known small animal species require higher doses of drugs and more frequent administration than larger species mostly because of metabolic rate differences. When adjusted for metabolic rate differences in the rat compared to the human the 1.725 mg/kg dose of omeprazole in the rat probably equates to just over the usual daily oral therapeutic dose of 20 mg/~70 kg adult human i.e. 0.28 mg/kg. Thus, lower doses are needed on a per kg basis in the human compared to the rat.

Omeprazole, even after maximal inhibition in the rat has a detectable but not substantial acid reducing effect for about a day in rats, and for about 3 days in the human and dog. The longer action detectable in the human compared to the rat is thought to be because of the metabolic rate differences. The effect at about day 3 in the dog and human is not substantial and the acid reducing effect is not therapeutic.

The lack of substantial acid reducing capacity or therapeutic acid reducing capacity, is because conventional acid reducing drugs, even ones that target the proton pump protein such as omeprazole have a short elimination half life of about 1 hr (Howden et al Clin Pharmacokinet 1991 January 20(1) 38-49). A longer detectable effect occurs because the antagonists covalently bonds the proton pump protein and there is slow turnover of protein (every 2 days in the rat) Gedda et al Gastroenterol 1995 October 109(4); 1134-41. Activity is returned with a half life of about 8-15 hours in the rat due to new protein production and loss of drug bound to the existing proteins.

In the human, an oligonucleotide antisense or like drug is expected to show an even longer acid reducing effect on a single dose than in the rat, and with a lower dose on a per kg basis than in the rat because of the metabolic rate differences between the rat and human. Our experiments when taking into account the metabolic rate differences between the rat and human, teach that a drug equivalent to ARISA 1 to the human proton pump alpha chain will have an effect for about 4 days to a week or more, based on the current 4 day substantial acid reducing effect observed in the rat. An even longer effect is expected to be achievable with variants of the humanized ARISA 1 oligonucleotide drugs that are more stabilized and more stabilized formulations. The particularly long half life of parietal cells that express the target proteins contributes to this expectation of a longer action been possible.

Action of Histamine H2 Receptor Oligonucleotide Drugs Can Also be Long

Other inhibitors of gastric acid production and secretion including the histamine H2 receptor antagonists have a short duration of action just like the proton pump protein inhibitor drugs. Infact they often need to be taken more frequently at about 3 times a day. Oligonucleotide drugs that target the histamine H2 receptor are expected to work with a similar low frequency of dosing as the proton pump inhibitor drugs.

Administration Alone, in Admixture, or in the Form of a Conjugate

The oligonucleotide and/or antagonists of the present invention may be administered by the same or different routes, either alone or together at substantially the same time or at different times to get the required improvement in acid reduction and biological response. Administration will depend on the pharmacokinetics of the drugs used and the formulation. Beginning acid reducing treatment, preferably there is an immediate effect (minutes to hours) and a short term effect (day-week) effect for reducing acid secretion. Also preferably there is a medium term effect (week-month) and if necessary a longer term effect (months and years) in maintenance treatment.

It is expected that deoxynucleoside phosphorothioate antisense drugs to the proton pump formulated correctly may be best administered about once a day or every other day in the human. The self stabilized deoxynucleoside phosphorothioates and/or the 2' Omethyl oligoribonucleotide phosphorothioate modified drugs such as those with four or more modified groups on either end, have a longer effect which is likely to extrapolate to 4 days to a week or more in humans as discussed above. The duration of effects are however dose dependent as shown in the Examples 1. Thus these drugs may be administered once a day, once a week, or less often depending on the dose and formulation.

It is noted that the doses given initially as used in the present experiments, and the doses given in maintenance therapy may differ, with the latter likely being lower.

Potential Benefits of Oligonucleotide Drugs and Long Acting Drugs Used in Therapy and Maintenance Treatment of Gastric Acid Disturbances The oligonucleotides of the present invention provide a number of benefits. Some of these benefits are associated with the longer half life of the drug and longer acid reducing action in vivo as shown herein, which benefits include improved efficacy, safety, and convenience, and perhaps reduced cost. Other benefits not necessarily associated with longer half life and long action may be in overcoming adverse effects associated with current pharmaceutical acid reducing drugs and unwanted interaction with cytochrome P450 that can occur with current acid reducing drugs. Also the oligonucleotide drugs may treat refractory conditions because they work at a different level or by a different mechanism of action. Other benefits depend on using these antisense or like acid reducing drugs in mixtures with conventional antagonists-inhibitor and agonists.

Long Acting Antisense or Like Acid Reducing Drug

A long acid reducing action of about four days to a week, or more, as is expected to be achievable in humans, may provide significant advantages in efficacy to reduce relapse rates over existing leading proton pump inhibitor technology, such as omeprazole, lansoprazole, pantoprazole, and rabeprazole. It may also improve safety, increase convenience and thus compliance and desirability, and reduce costs of treatment.

Gastric Reflux

In reflux treatment in humans it is preferable to maintain oesophageal pH above 4 for at least 96% of the 24 hour period (Howden et al Scan J Gastroenterol Suppl 1994; 201; 79-82); Hunt, Aliment Pharmacol Ther 1995; Suppl 1:3-7).

Using a single standard safe dose of 20 mg for current leading drugs the average achieved is 68.5% (25-100) of the day in normal volunteers (Mohiuddin et al Dig Dis Sci 1997 April 42(4); 715-719). In most patients it is the next standard dose the day after that increases the pH above 4. About 15-40% of people take standard doses twice a day but nocturnal acid levels are still not appropriate. This lack of efficacy in some part of the day or night can cause relapse, particularly in patients that forget to take their medicine or those that self medicate when symptoms appear.

With current acid reducing drugs about 40% self medicate when symptoms appear while another 24% take drugs regularly on a daily basis (Schindlebeck Fortschre Med 1996 January 20; 114(1-2) 31-34). Those that take the proton pump inhibitor drugs daily do not suffer many relapses while those that take drugs less regularly do. If gastric reflux maintenance therapy is provided according to the present invention, wherein there is low frequency dosing of once every about 4 days to a week, or less often, those that self medicate when symptoms appear are likely to suffer fewer relapses in any one year because of the fewer intervals between efficacious acid reduction.

Because the long acting acid reducing drug of the present invention may be taken less frequently, its use will be more convenient than current drugs taken daily. Similarly it will be more convenient and easier to comply with than using multiple daily doses in the case of refractory diseases.

Studies of patients refractory to standard doses of omeprazole and famotidine (the most effective histamine H2 receptor antagonist) show that these patients miss maintaining oesophageal pH above 4 for ~12%-35% of the day (Yamashita et al Nippon Shokakibyo Gakkai Zasshi 1994 December 91(12) 2166-2173). They need to be given double or triple standard doses once a day (Klinkenberg-Knol Dirgestion 1992; 51 Suppl 1: 44-40) or doses more frequency (Leite et al Am J Gastroenterol 1996 August 91 (8) 1527-1531.

However, doses of 40 mg/day cause a high pH, which high pH causes slight increases in gastrin levels in the human and related ECL hyperplasia which is of concern to many gastroenterologists. Creutzfeldt (Drug Safety 1994 January 10(1) 66-82) observes moderate hypergastrinaemia especially with 40 mg/day of omeprazole. Similarly when using 40 mg/day a significant increase in gastrin release occurs during omeprazole treatment and results in increase ECL mass (Waldrum et al Gut 1996 November 39:5 649-53). A 40 mg omeprazole daily dose for treatment of gastric reflux causes rises in gastrin levels, while 20 mg doses for up to a year in maintenance causes no further alterations in gastrin levels (Lind et al Scand J Gastrenterol 1991 June 26(6) 620-626). Similarly Dent et al (Gut 1994 May 35(5) 590-598 has shown that with 20 mg daily doses of omeprazole, median gastrin levels increase slightly during the healing phase but remain within the normal range and do not change during maintenance treatment. No significant pathological findings were noted in the gastric ECL cells (Hetzel (Digestion 1992 51 Suppl 1 35-42).

In animals gastrin increase is detectable in 5 days after acid reduction (Poynter Mut Res 1991 June 248 (2) 303-319 and gastrin infusion causes ECL hyperplasia after about 4 days (Hakanson et al Digestion S5 Suppl 3 338-45).

It is expected that dosing with a longer acting acid reducing antisense or like drug will be safer. For instance a dose may be used that has a maximum effect at day 4 but maintains therapy and prevents relapse for the week. If used at 1 week regular intervals, because of the slow loss of acid reducing effect at the end of each week, acid levels will have had a chance to gradually and slightly increase every week before the next dose. The slight recovery of acid levels means gastrin may not have had a chance to increase at day 5 and the hyperplasia occurring later will therefore be restricted or reduced.

Peptic Ulcer Disease

A long acting acid reducing drug may improve efficacy of treatment of peptic ulcer caused by NSAID treatment with fewer relapses on a single standard safe dose, and with improved convenience of use.

The majority of ulcers not caused by the bacterium *H. pylori* are caused by the use of NSAIDs (non steroid anti inflammatory drugs). Preferably in treating NSAID caused ulcer disease is to maintain gastric pH above 4 (Dent Am J Med 1998 Mar. 30 104 (3A) 52 S-55 S). This may require a single standard dose or for patients more refractory to acid reduction, a single double dose or two standard doses each day. Thus the statements made above in item 1, 2, and 3 with regard to improved efficacy with fewer relapses, increased convenience, and for patients on larger doses improved safety, may apply to these NSAID patients.

Much simpler treatment afforded by the use of an acid reducing agent taken once a week will be particularly important for the elderly and sick. Kirchner (J Am Osteophat Assoc 1994 94(4) 300-304) indicates that drugs that are administered once daily are important for the elderly in treatments of NSAIDS. A drug administered just once a week in the treatment of peptic ulcers would presumably be even more convenient for the elderly.

Improving Efficacy of Treatment of Peptic Ulcers Caused by *H. pylori*

Over 90% of duodenal ulcers and 70% of gastric ulcers, that is peptic ulcers, are thought to be caused by *H. pylori* (O'Connor Scan J Gastroenterol Suppl 1994 201; 11-15). Many patients are being put on eradication therapy, whilst others are not.

In cases where the bacterium is not eradicated, treatments using a long acting acid reducing drug may become more effective and more convenient.

Many patients with *H. pylori* infections do not use eradication therapy for various reasons. For peptic ulcer disease between 22-24% tend to self medicate when symptoms arise whilst the rest take their medication daily as required (Lee et al West Indian Med J 1995 June 44(2) 58-59, and Ryder et al BMJ mar 26 308 6932 827-830). Patterns of use differ to what is recommended (Leufkins Aliment Pharmacol Ther 1997 October 11(5) 887-897).

Using a longer acting antisense or like drug with an effect for about four days to one week, or longer means that those that self medicate when symptoms appear are likely to suffer fewer relapses in any one year because of the fewer intervals between efficacious acid reduction.

Treatments using a long acting acid reducing drug may also become more effective and simpler in peptic ulcer *H. pylori* eradication therapy.

Current treatments are carried out over a week or two weeks and are complex. They require one or two antibiotics each taken two to three times a day, and acid reducing agents often taken two times a day (Bigard et al Aliment Pharmacol Ther 1998 12(4) 383-388); (Reed, Biomed Pharmaocother 1997; 51(1) 13-21); (Lee et al Yonsei Med J 1996 August 37(4) 270-277); Seelis Dtsch Med Worchenshhr 1998 January 30; 123(5) 103-108); Chey et al Am J Gastroenterol 1997 September 92(9) 1483-1486); This Alimentary Pharmacol Aliment Ther 1997 April 11(2) 305-309.

A long acting acid reducing agent may be taken once for the first week and/or second week with the antibiotics treatment and make treatment simpler and more effective; The acid reducing drug omeprazole are often taken at 20-40 mg twice a day in *Helicobacter* eradication to ensure pH is maintained high starting from day 1 and throughout the day because the high pH ensures acid sensitive antibiotics work and have an antibacterial effect. The long acting acid reducing drugs of the type described herein may be taken with omeprazole at day 1 and achieve this high pH protection beginning immediately. It may also be sustainable over a week without further doses. Thus the treatment is likely to provide a simpler dosing regimen which because of higher compliance rates, ensures higher pH throughout the week, which will have improved efficacy.

An even bigger increase in pH (reduction in acid secretion) may be achieved with mixtures leading to increased efficacy in eradication therapy. About 10%-15% of patients are refractory to the conventional 1-2 week acid reducing and antibiotic treatment for eradication of the bacterium, often because of adverse effects and compliance rates but also because there are limitations in the increase in pH and its duration that can be achieved with current drugs. Using a combination of the acid reducing antisense or like drug, and the antagonist to a proton pump such as omeprazole, should produce the necessary high pH, and improve the bacterial eradication rates.

Lower Frequency of Dosing Used with Current Drugs—Increased Compliance and Desirability Using a less frequent dosing regimen of once a week, may be more desirable and provide better compliance rates.

Hattlebakk Clin Pharmacokinetic 1996 November 31 (5) 386-406 suggests an ideal treatment is to have duration of action allowing once daily administration. Others have generally considered this as being optimal with conventional therapeutics. This is based on studies where multiple dosings a day were compared to single daily doses.

Peptic ulcer patients in maintenance therapy may use once a day dosing but often dose once every second day with 20 mg omeprazole. Di Mario F et al (Minerva Gastroenterol Deitol 1993 June; 39(2) 83-7, reported than once every other day of omeprazole afforded better compliance rates and efficacy than daily doses of ranitidine (a histamine H2 receptor antagonist); omeprazole every other day was however found less efficacious than daily omeprazole (this is not always the case).

Other studies have also tried to reduce frequency of dosing in gastric reflux and ulcer treatment and maintenance therapy because it was considered desirable.

Early acid reducing studies tried 20 mg omeprazole on Friday, Saturday, and Sunday as maintenance therapy in duodenal ulcers but this was not as effective as 10 mg/day Walan Digestion 1990 47 Suppl 1:54-58; a dose of 10 mg of omeprazole is known today not to be sufficient for most treatments and provides variable results.

Similarly Hetzel (Digestion 1992 51 Suppl 1 35-42) and then Dent et al (Gut 1994 May 35(5) 590-598) used the 20 mg omeprazole on Friday, Saturday, and Sunday, to prevent relapse in reflux oesophagitis; but this also was less than half as effective as daily omeprazole and thus did not catch on.

Intermittent dosing with omeprazole 3 time a week, in maintenance therapy with erosive oesophagitis was tried by Sontag et al (Aliment Pharmacol Ther 1997 April 11(2) 373-380. However, this was less than half as good as every day dosing and again did not catch on.

In summary, although it is desirable to decrease frequency of dosing in the treatment of acid disturbances, lack of long effective action when using omeprazole is a limitation. Omeprazole may have an effect for more than one day, but its short action of about 50% at the end of each day (See Merck Index) means the available acid reducing effect is not sufficient and not recommended in maintenance treatment of erosive oesophagitis.

Lower frequency than once a day dosing is currently used in maintenance treatment of less severe forms of the gastric reflux disease, which includes 60-85% of patients. It is also used in some duodenal and gastric ulcer treatments. The use of even low frequency of dosing of once every 4 days to a week or less often with an oligonucleotide drug is likely to be more desirable for less severe forms of disease and in particular chronic sufferers.

Lower Total Costs of Treatment

The long acting antisense and like acid reducing technology, which requires dosing of once every 4 days to a week or less often has potential advantages in total costs of treatment. Lower costs of treatment would occur in situations where the hospital or carers time is taken into account, and saved because of the lower frequency of dosing.

Other Advantages of Oligonucleotide Drug(s) Acting at a Different Level Treating Refractory Conditions Drugs that work at a different level such as the nucleotide level, may be useful in the treatment of the about 6-8% of reflux and 5-15% of ulcer sufferers that are refractory to current treatments using proton pump inhibitor drugs.

Individual Variation May be Less and Treatment and Maintenance Therapy May be More Predictable Wide individual variation occurs at the level of gastric proton pump protein activity and a lot of time is spent working out the individual patients requirements, using standard doses of proton pump inhibitors which work at the level of the active protein. This is particularly so for patients refractory to standard doses. Inability to find appropriate does leads to greater relapse rates (Klinkenberg Knol 1992 Supra and Leite et al 1996 Supra).

One of the studies in the rat described herein using lower frequency of dosing suggests that changes in acid levels are less variable when using antisense drugs compared to daily doses of omeprazole. Treatment is expected to be even less variable at the level of the gene perhaps because there is only one gene while there are a number of messages. The new antisense and antigene drugs and ability to transfect parietal cells in vivo allow studies to be performed at the level of the message and/or gene. If individual variation is less at the level of the message and/or gene practitioners could prescribe standard doses of an antisense or antigene acid reducing drug therapy with more confidence that there will be efficacy in the majority of patients and patients with fewer relapse rates.

Mixtures and Conjugates-Combinations

Mixtures of antisense to the proton pump and antagonists to the proton pump may be used to increase pH and increase the rate of pH increase from the time of administration, above what can be achieved with either agent alone. Using such mixtures, there is increased likelihood that eradication therapy will work better, as the antibiotics are acid sensitive and *H. pylori* bacteria that cause the acid disturbances are sensitive to high pH.

The mixture and conjugate technology may also improve therapy via the histamine H2 receptor, compared to current antagonist to histamine H2 receptors, because the optimal acid reducing effect would be obtained via this route. This may make therapy via the histamine H2 receptor antagonists as efficacious as proton pump antagonists in some instances. It may also increase the speed of acid reduction.

Another likely advantage of an antisense drug to the proton pump used in combinations with omeprazole is to produce a more acute and/or complete effect which is important in hypersecretory conditions requiring much higher doses of proton pump inhibitors, and refractory conditions some of which require surgery (Fass et al Am Fam Physician 1997 January 55(1) 205-212) and Freston et al Eur J Gastroenterol Hepatol 1995 June 7(6) 577-586).

Improved Safety in Multiple Therapy

It is also likely the antisense and antigene or like acid reducing drugs will be safer in certain multiple therapies because such drugs do not significantly affect cytochrome P450. Morpholino phosphorodiamidates are particularly good in this regard.

Proton pump inhibitors are metabolized mainly in the liver via the cytochrome P450 system and interactions are possible with drugs metabolized in the same way e.g. cyclosporine, disulfiram and benzodiazepine (See Merck Index). Omeprazole prolongs the elimination of diazepam, warfarin and phenyloin, thus omeprazole should be used with caution when administering these medicines because of the multiple effects on cytochrome P450 (Howden Clin Pharmacokinet 1991 January 20 (1) 38-49; also Merck Index). Histamine H2 receptor antagonists also interfere with the absorption, metabolism and elimination of these drugs and thus the same cautions usually exist.

This capacity for improved safety in multiple therapies is particularly important for the elderly who are on multiple medications including cyclosporine, disulfiram and benzodiazepine, diazepam, warfarin and phenyloin (Koop Z Gerontol 1992 September 25(5) 304-308).

An antisense or like acid reducing drug that has lower binding to the cytochrome P450 and allows multiple drugs to be used in therapy would be preferred when using cyclosporine, disulfiram and benzodiazepine, diazepam, warfarin and phenyloin.

Adverse Effects; Disadvantages in Current Acid Reducing Technology that may be Overcome Other problems with current proton pump inhibitor technology, omeprazole, lansoprazole, pantoprazole and other acid reducing technology such as misoprostol, include adverse effects which lead to lower compliance rates. Adverse effects include nausea, dizziness, and diarrhea, headaches, skin alterations, giddiness, dizziness, fatigue and constipation The antisense or like acid reducing drugs may overcome some of these adverse effects and thereby increase patient compliance and increase drug efficacy.

Antisense and Like Therapy is also Potentially Reversible.

Using an antidote oligonucleotide that binds to part or all of the therapeutic antisense, ribozyme, oligozyme, or antigene or like drug, acid secretion may be normalized or fine tuned if necessary. Thus overdoses with oligonucleotide drugs are controllable. This contrasts with omeprazole therapy whose effects cannot be directly reversed.

For healing of ulcers one may be attempting to achieve acid production of 20% of the constitutive levels, and thus inhibition of about 80% of constitutive acid production. One may produce too much decrease in acidity when targeting the proton pump, through which all other pathways feed. Virtual inacidity with the use of too much omeprazole is a problem. If using an antisense or antigene agent to the proton pump then it is possible to administer an antidote oligonucleotide agent partly or completely complementary and capable of duplex or triplex formation with the antisense, ribozyme, oligozyme or antigene or like agent, that recognizes the antisense and antigene agent and interferes or modulates its action. In this way it is relatively easy to control levels of acidity in a drug specific manner.

An antidote agent may be a smaller molecule than the acid reducing drug. It may form a duplex and lead to cleaving of the target therapeutic antisense and antigene agent and/or act via triplex formation or any other mechanism.

An alternative antidote agent may interfere with a pathway known to decrease acid production and thereby bring up acid levels.

BRIEF DESCRIPTION OF THE DRAWINGS

The invention will now be further described by way of reference to the accompanying drawings, in which.

Figure 1:
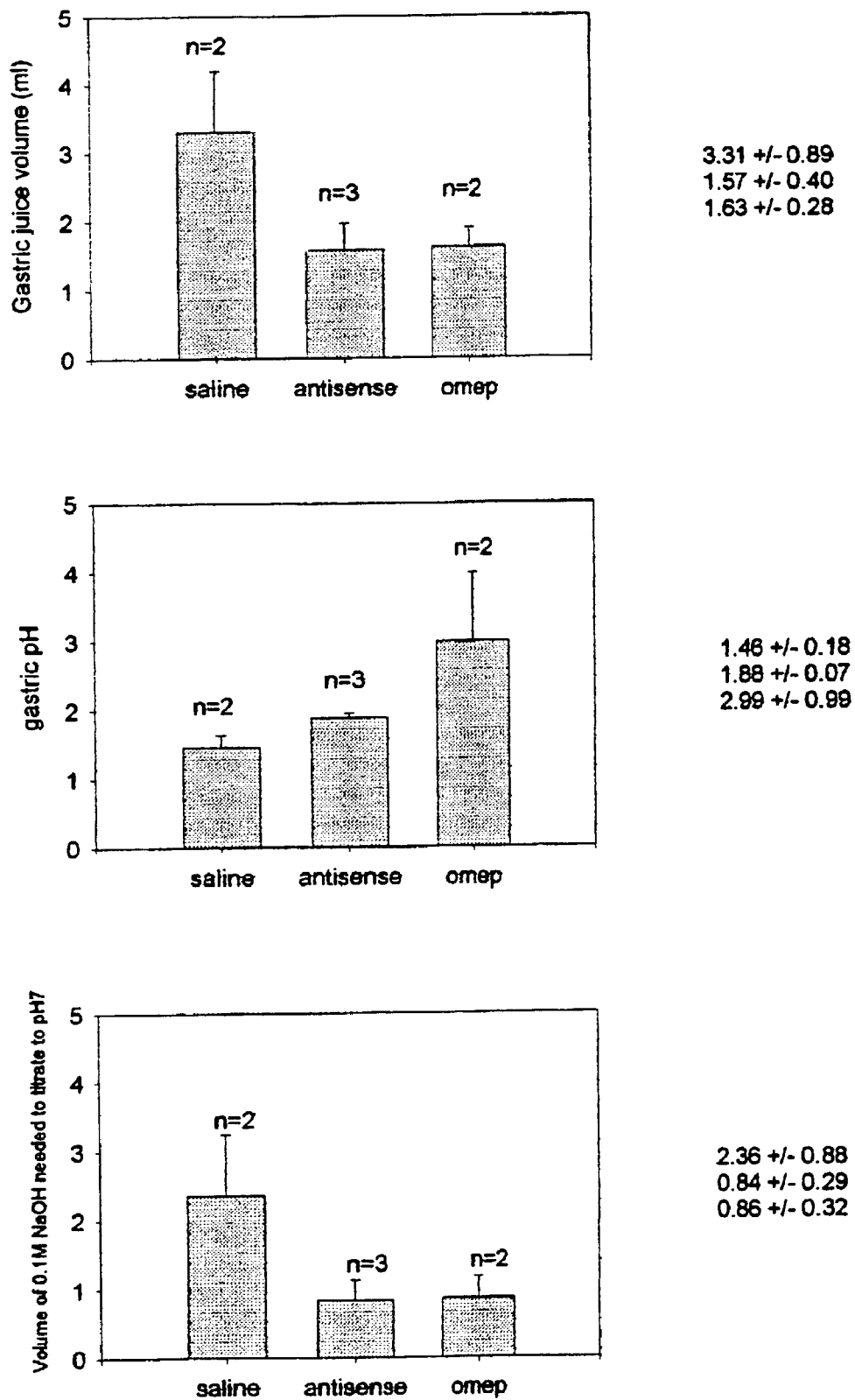
FIG. 1 shows bar charts for saline, antisense and omep in respect of gastric juice volume (ml), gastric pH and volume of 0.1 MnaOH needed to titrate to pH 7.

The invention will now be described by way of reference only to the following non-limiting Examples.

EXAMPLE 1

Testing Prototype Designed Drugs for Activity

EXPERIMENT 1

Manufacture of the First Prototype Antisense Drug to the Rat Gastric Proton Pump—ARISA 1

7 mg of HPLC purified 23 nm er AAUUCA TAA TTC TCC TTC CCCAU SEQ ID NO:1 (designated ARISA 1) directed to the initiation codon of the rat gastric proton pump was made by Integrated DNA Technologies (1710 Commercial Park Coralville, 1A, 52241 United States) and shipped suspended in sterile normal saline. The underlined bases are 2' O methyl oligoribonucleoside phosphorothioates and the other bases are deoxynucleoside phosphorothioates.

Storage and Handling and Preparations of the Antisense Drug

The reagent was transported at room temperature ~25 degrees celsius for 7 days, stored at 4 degrees celsius for 11 days, and stored at −20 degrees celsius for 5 weeks before use. The reagent was thawed and bought to room temperature. A stock solution of 3.2 mg/ml was made in Dulbecco's phosphate buffered saline (PBS). This stock was diluted a further 2 fold for Experiment 1. The remaining stock was stored at −20 degrees celsius for use in later Experiments 2 and 5.

Animal Testing For Effect Via Oral Administration and Long Action

Animal work for testing the drugs was contracted to Dr G. A. Cook, Dr A. S. Giraud and Prof N.D. Yeomans of the Department of Medicine, Western Hospital, The University of Melbourne, Gordon Street Footscray, 3011, Victoria Australia. They set up a pyloric ligation rat animal model. The animals used were male adult Long Evans strain rats originally derived from *Rattus Norvegicus* of about 150-200 g.

The rats were provided with a conventional diet and water ad libitum before transport, were without food or water during transport to the laboratory from about 9 am to 2 pm, and were with food and water for 1 hr while in the laboratory before administration with antisense drug, the first dose of positive control omeprazole solution, and the negative control saline.

0.5 ml (0.8 mg) of antisense drug in PBS was given by gavage to each of three rats (160 mg) on Monday afternoon at about 3 pm (time zero). This corresponded to a dose of 5 mg/kg.

The three negative control rats received 500 ul (microlitres) of PBS by gavage at the same time.

Two other rats received a dose of 3.45 mg/kg of freshly made omeprazole-PBS solution intraperitoneally at about the same time.

The rats were then provided with a conventional diet and water ad libitum.

These omeprazole treated rats also received, four more daily injections meaning they were dosed Monday through to Friday.

On the Thursday afternoon (5 pm), being the day before pyloric ligation, the animals were placed without food in special metabolic cages to minimize caprophagy. Thus the animals did not have food in their stomach on the Friday morning, being the time of pyloric ligation.

The two omeprazole positive control animals were injected intraperitoneally with omeprazole solution one hour before pyloric ligation on the Friday morning. The animals were then allowed to recover, and roam around freely, before being lightly anaesthetized and having their pylorus ligated.

The other animals that had gavage administration, were also lightly anaesthetized and had their pylorus ligated.

The animals with their pylorus ligated were allowed to recover, and then two hours later, anaesthetized and their gastric contents recovered before humanely euthanizing.

About 92 hours had passed from the initial gavage and ip administrations to the time the gastric contents were recovered.

Data from the First Prototype Drug Testing

The volume of gastric acid, the pH of the gastric acid, and the volume of 0.1M NaOH needed to titrate the gastric contents to pH7 was determined.

The data is shown in FIG. 1. The data shown is the mean +/− the standard error of the mean.

One of the three control saline rats had blood in the stomach following pyloric ligation. Blood in the stomach has a buffering effect and thus the data for it was excluded from the results.

The volume of gastric juice in the saline controls was 3.31 ml+/−0.89 ml standard deviation. The single dose of antisense drug and 5 daily doses of omeprazole reduced the volume of gastric juice to 1.57+/−0.4 and 1.63+/−0.28 respectively.

The gastric pH in the saline control was 1.46+/−0.18. The single dose of antisense drug and 5 daily doses of omeprazole increased pH to 1.88+/−0.07 and 2.99+/−0.99 respectively.

The volume of 0.1 M NaOH needed to titrate the gastric contents to pH7 for the saline control was 2.36+/−0.88. The volume of 0.1 M NaOH needed to titrate the gastric contents to pH7 for the antisense and omeprazole was 0.84+/−0.29 and 0.86+/−0.32 ml respectively.

This data shows that the antisense drug given by gavage once at 5 mg/kg works at 92 hours post dosing. It works as well as five single 3.45 mg/kg daily intraperitoneal doses of omeprazole in reducing total H+ ions in the stomach.

The data was more variable for the omeprazole compared to the antisense drug. The significance of differences between the saline, and the test drug, and saline and omeprazole was analyzed using the Student-Newman-Keuls method (t-test analysis).

t-test analysis shows that for the volume of gastric juice studies the p=0.13 and 0.21 for the antisense and omeprazole relative to the saline control.

For the gastric pH the t-test gave p=0.08 and 0.27 for antisense and omeprazole respectively.

For the volume of 0.1M NaOH needed to titrate to pH7, the t-test analysis gave p=0.14 and 0.25 for antisense and omeprazole relative to the saline control.

It is noted that about 20-50 ul of the 500 ul antisense drug and saline negative control is lost during the gavage process. This corresponds to about 4-10% of the dose. In contrast very little of the omeprazole drug is lost during intraperitoneal injections. The dose of omeprazole is about 10-fold the usual 20 mg per day human therapeutic dose on a per kg basis.

Also noted is the good stability of the drug. The reagent was transported at room temperature ~25 degrees celsius for 7 days, stored at 4 degrees celsius for 11 days, and stored at −20 degrees celsius for 5 weeks before use. This suggests antisense drugs made using this chemistry are appropriate reagents for handling by the public.

EXPERIMENT 2

Repeat of the Above Experiment with ARISA 1

The above experiments in 1 were repeated. The stock antisense drug which had been stored for a further week at −20 degrees was thawed, bought to room temperature, and given to 3 animals as described above in Experiment 1.

Control saline was given by gavage to three animals, and omeprazole solution was given to three animals as also outlined in Experiment 1.

The volume of gastric acid, the pH of the gastric acid, and the volume of 0.1M NaOH needed to titrate the gastric contents to pH7 was determined.

Figure 2:
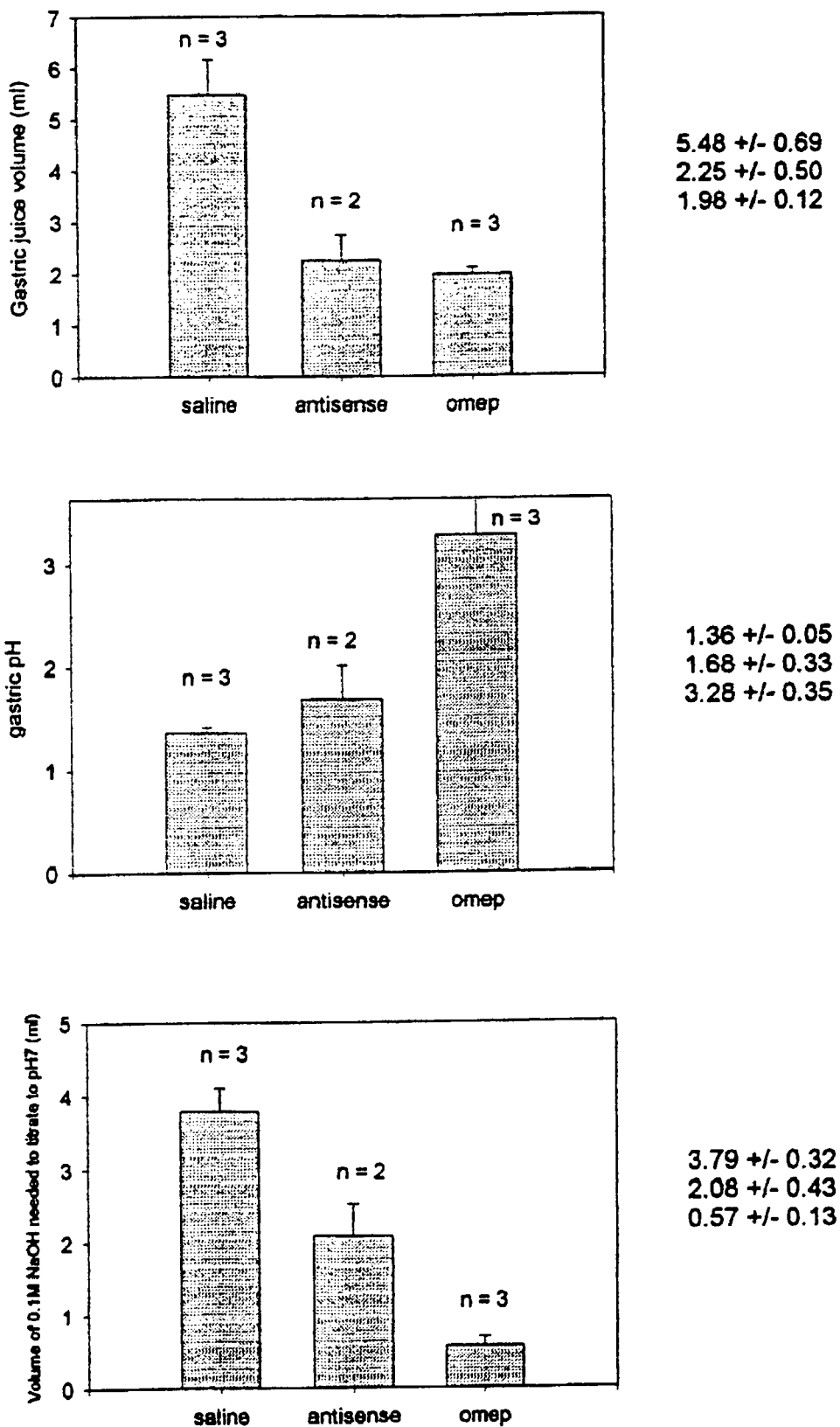
FIG. 2 shows bar charts for results for Experiment 2 obtained when the Experiment 1 shown in FIG. 1 were repeated and the stock antisense which had been stored for a further week at −20° was thawed brought to room temperature and given to three animals as described in Experiment 1.

The data is shown in FIG. 2. The data shown is the mean +/− the standard error of the mean.

One of the three antisense treated rats had blood in the stomach following pyloric ligation. Blood in the stomach has a buffering effect and thus the data for it was excluded from the results.

The volume of gastric juice in the saline controls was 5.48 ml+/−0.69 ml standard deviation. The single dose of antisense drug and 5 daily doses of omeprazole reduced the volume of gastric juice to 2.25+/−0.50 and 1.98+/−0.12 respectively.

The gastric pH in the saline control was 1.36+/−0.05. The single dose of antisense drug and 5 daily doses of omeprazole increased pH to 1.68+/−0.33 and 3.28+/−0.35 respectively.

The volume of 0.1 M NaOH needed to titrate the gastric contents to pH7 for the saline control was 3.79+/−0.32. The volume of 0.1 M NaOH needed to titrate the gastric contents to pH7 for the antisense and omeprazole was 2.08+/−0.43 and 0.57+/−0.13 ml respectively.

The data from Experiment 2 shows the antisense drug works at 92 hours post dosing about as well as a single 1.725 mg/kg intraperitoneal dose of omeprazole in reducing total H+ ions in the stomach (refer to the data in Experiment 3). It was not as effective as five daily 3.45 mg/kg doses of omeprazole as observed for the same drug and dose in Experiment 1.

One difference between Experiment 1 and 2 was that the antisense drug had been freeze thawed a second time. The drug had been stored at room temperature −25 degrees celsius for 7 days, stored at 4 degrees celsius for 11 days, and stored at −20 degrees celsius for 5 weeks before thawing and use in Experiment 1, freezing at −20 degrees celsius another week, and then thawing before being given by gavage once at 5 mg/kg in Experiment 2. Comparing the data from Experiment 1 and 2 suggests that the antisense drug may be negatively affected by the second freeze thawing before use. It is equally likely however, that the differences reflect the variability of acid reducing data in long time course experiments. The data in Experiment 2 was in itself also more variable for the antisense drug compared to the omeprazole, in contrast to what was observed in Experiment 1. The data from Experiments 1 and 2 were pooled.

Pooling of Data from Expt 1 and 2 and Another Omeprazole Experiment*

Figure 3:
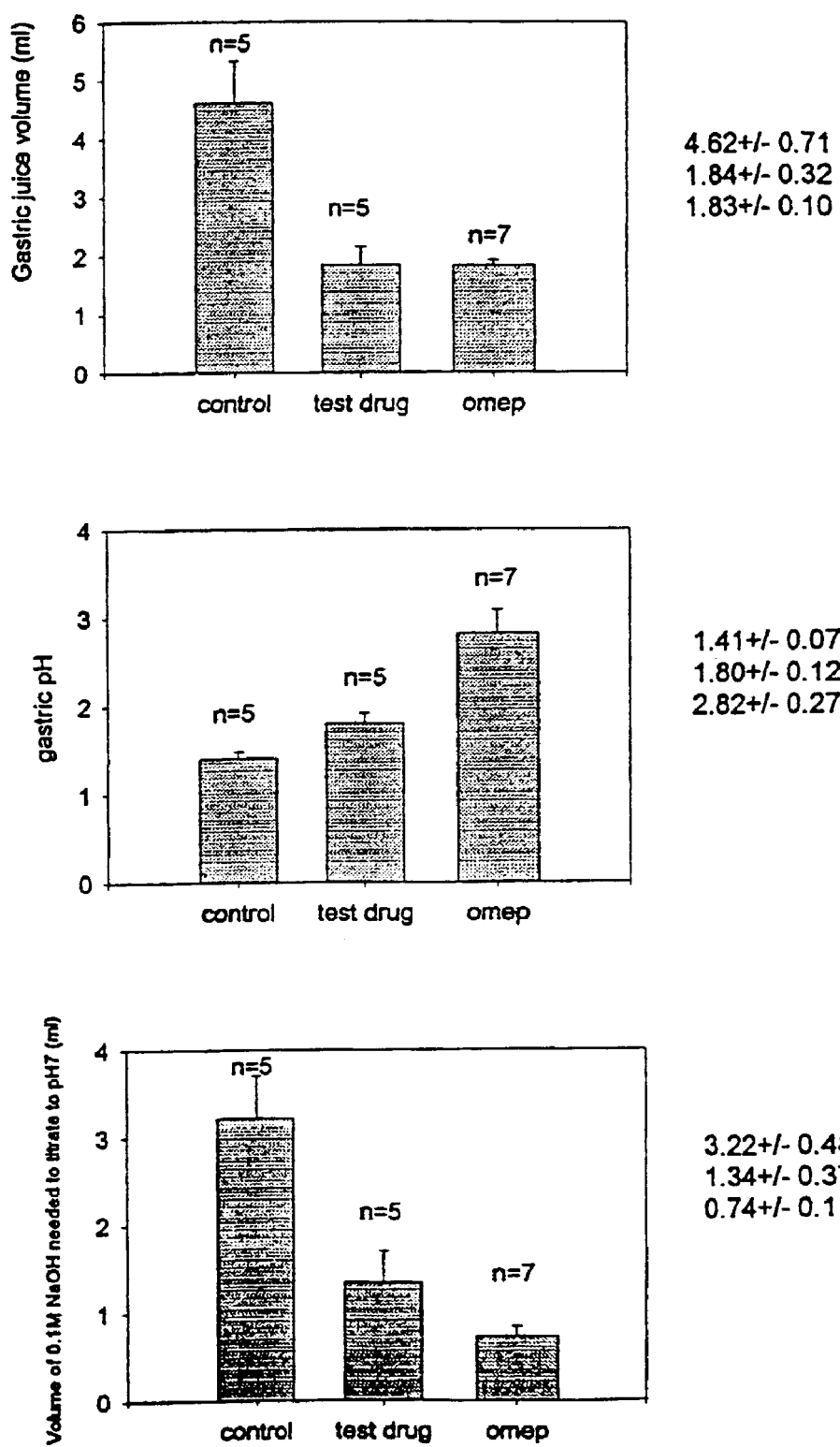
FIG. 3 shows bar charts of pooled data obtained from data from Experiments 1 and 2 pooled with data from another two rats dosed with 3.45 mg/kg omeprazole from a previous omeprozole dose response study and t-tests performed.

The data from Experiments 1 and 2 were pooled with data from another 2 rats dosed with 3.45 mg/kg omeprazole from a previous omeprazole dose response study* (data not shown separately) and t-tests done. The significance of differences between the saline, and the test drug, and saline and omeprazole was analyzed using the Student-Newman-Keuls method. The pooled data is shown in FIG. 3. The data shown is the mean +/− the standard error of the mean.

The volume of gastric juice in the saline controls was 4.62 ml+/−0.71 ml. The single dose of antisense drug and 5 daily doses of omeprazole reduced the volume of gastric juice to 1.84+/−0.32 and 1.83+/−0.10 respectively.

The gastric pH in the saline control was 1.41+/−0.07. The single dose of antisense drug and 5 daily doses of omeprazole increased pH to 1.80+/−0.12 and 2.82+/−0.27 respectively.

The volume of 0.1 M NaOH needed to titrate the gastric contents to pH7 for the saline control was 3.22+/−0.48. The volume of 0.1 M NaOH needed to titrate the gastric contents to pH7 for the antisense and omeprazole was 1.34+/−0.37 and 0.74+/−0.11 ml respectively.

This pooled data suggests that the antisense drug given by gavage once at 5 mg/kg works at 92 hours post dosing. It works as well as a single 1.725 mg/kg intraperitoneal dose of omeprazole in reducing total H+ ions in the stomach (see Expt 3). The 1.725 mg/kg dose of omeprazole is about 5-fold the usual 20 mg per day human therapeutic dose on a per kg basis.

The pooled data was also more variable for the antisense drug compared to omeprazole. This is because a larger number of animals were tested using the omeprazole (n=7) compared to antisense drug and saline (n=5), and perhaps also because of the dual freeze thawing of the antisense drug in Expt 2.

t-test analysis shows that for the volume of gastric juice studies the p=0.007 and 0.0009 for the antisense and omeprazole relative to the saline control.

For the gastric pH the t-test gave p=0.024 and 0.0016 for antisense and omeprazole respectively.

For the volume of 0.1M NaOH needed to titrate to pH7, the t-test analysis gave p=0.015 and 0.0001 for antisense and omeprazole relative to the saline control.

Thus, the results obtained using the antisense drug are significant.

EXPERIMENT 3

1 Administration of 1.725 mg/kg Omeprazole—Analysis of Gastric Contents Obtained at Between 1-3 Hours Post Dosing—Half the Dose Used in Expt 1 &2 and Only One Dosing Three Long Evans rats were injected intraperitoneally once with 1.725 mg/kg of omeprazole solution one hour before pyloric ligation. The animals were then allowed to recover, and roam around freely, before being lightly anaesthetized and having their pylorus ligated. The animals were allowed to recover, and then two hours later, anaesthetized and their gastric contents recovered before humanely euthanizing.

The volume of gastric acid, the pH of the gastric acid, and the volume of 0.1M NaOH needed to titrate the gastric contents to pH7 was determined.

The data is reported below. The data expressed is the mean +/− the standard error of the mean.

The volume of gastric juice following the single dose of omeprazole produced a volume of gastric juice of 1.73+/−0.20 ml.

The gastric pH with the single dose of omeprazole produced pH 1.78+/−0.20.

The volume of 0.1 M NaOH needed to titrate the gastric contents to pH7 for the single dose of omeprazole was 0.94+/−0.22 ml.

It should be noted that after a single dose of omeprazole, maximum reduction of acid secretion occurs between about 1-3 hours post dosing. Thus, the maximal effect is being observed in this study.

Comparing this data obtained at 1-3 hours post a 1.725 mg/kg ip dose of omeprazole with the saline control data in Experiments 1 and 2, where the animals were given saline orally 92-94 hours before analysis, shows a reduced volume of gastric juice, and increased pH as expected.

A single 1.725 mg dose of omeprazole drug does not lead to the same reduction of acid levels as five consecutive daily doses of 3.45 mg/kg over 92 hours (Expt 1 and 2). This observation is consistent with what is known in the prior art, namely that maximal acid reduction levels are achieved after about 4 daily doses, and acid reducing capacity is dose dependent up to a certain maximal dose.

It should be noted that the dose used in Expt 3 is about 5 times the human dose on a per kg basis whereas the dose used in Expts 1 and 2 is about 10 times the human dose on a per kg basis. When taking into account interspecies variation in metabolic rates, the doses used are just about equivalent to the usual recommended therapeutic daily doses of 20 and 40 mg omeprazole in humans.

EXPERIMENT 4

A Negative Control Antisense Drug to ARISA 4 mg of HPLC purified 23 nm er UACC CC TTC CTC TTA ATA CUUAA (SEQ ID NO:22) was made by Integrated DNA Technologies (1710 Commercial Park Coralville, 1A, 52241 United States) and shipped suspended in sterile normal saline. The underlined bases are 2' O methyl oligoribonucleoside phosphorothioates and the other bases are deoxynucleoside phosphorothioates.

This sequence is the reverse sequence of the test antisense drug ARISA 1 used in Experiments 1 and 2. The reverse sequence keeps the identical base composition and nearest neighbour bases the same as ARISA 1. It thereby functions as the most appropriate negative control.

The negative control reagent was transported at room temperature ~20 degrees C. for 4 days and was then used immediately.

The animal experiments were as described for the test antisense drug in Expts 1 and 2. Briefly, each of 4 animals received a 0.5 ml dose (5 mg/kg) of the negative control antisense drug on Monday. About 5 pm on Thursday, they were placed in metabolic cages, and on Friday were lightly anaesthetized and had their pylorus ligated. The animals were allowed to recover and then 2 hours later anaesthetized and their gastric contents recovered before humanely euthanizing.

The volume of gastric acid, the pH of the gastric acid, and the volume of 0.1M NaOH needed to titrate the gastric contents to pH7 was determined.

The data is described below. The data is the mean +/the standard error of the mean.

The volume of gastric juice in the negative antisense controls was 4.60+/−1.12 ml; this is the same as the volume of the saline negative control data 4.62 ml+/−0.71 ml standard error of the mean when pooling the data from Expt 1 and 2. The single dose of the test antisense drug ARISA 1 and 5 daily doses of omeprazole reduced the volume of gastric juice to 1.84+/−0.32 and 1.83+/−0.10 respectively.

The gastric pH in the negative control antisense was 1.47+/−0.24; this is about the same as the saline control data of 1.41+/−0.07 when pooling the data from Expt 1 and 2. The single dose of antisense drug ARISA 1 and 5 daily doses of omeprazole increased pH to 1.80+/−0.12 and 2.82+a 0.27 respectively.

The volume of 0.1 M NaOH needed to titrate the gastric contents to pH7 for the negative control antisense drug was 3.90+/−1.00; this is just above the saline control data of 3.22+/−0.48 when pooling the data from Expt 1 and 2. The volume of 0.1 M NaOH needed to titrate the gastric contents to pH7 for the test antisense drug ARISA 1 and omeprazole was 1.34+/−0.37 and 0.74+/−0.11 ml respectively.

This data shows that a fresh batch of negative control antisense drug given by gavage once at 5 mg/kg produces at 92 hours post dosing, an effect similar to a negative control saline at 92 hours post dosing. Thus the reduction in acid secretion produced with the oral 5 mg/kg dose of test antisense drug ARISA 1 at 92 hours post dosing is likely due to a specific effect on the proton pump alpha chain message.

EXPERIMENT 5

Lower Dose of ARISA 1

The antisense drug ARISA 1 had been stored at room temperature ~25 degrees celsius for 7 days, stored at 4 degrees celsius for 11 days, and stored at −20 degrees celsius for 5 weeks before thawing and use in Expt 1, freezing at −20 degrees celsius another two weeks, and then thawing before being given by gavage once at 1.6 mg/kg in this Experiment 5. The antisense drug was stored for a further week at −20 degrees compared to Experiment 2 but had been freeze thawed the same number of times.

On Monday, five animals were given a lower doses of the prototype antisense drug (1.6 mg/kg) prepared in 250 ul of phosphate buffered saline (i.e. half the volume used in Expt 1 and 2 and 3) and administered at time zero by gavage. Other than this all animal experiments were as described for the same antisense drug in Experiments 1 and 2.

These five animals had their pylorus ligated on Friday and allowed to recover, and then 2 hours later anaesthetized and their gastric contents recovered before humanely euthanizing.

The volume of gastric acid, the pH of the gastric acid, and the volume of 0.1M NaOH needed to titrate the gastric contents to pH7 was determined.

The data is described below. The data is the mean +/− the standard error of the mean.

The single dose of antisense drug produced a volume of gastric juice of 4.16+/−0.81, which is only slightly reduced relative to the saline (4.62 ml+/−0.71 from expts 1 and 2) and antisense negative control 4.60+/−1.12(5 mg/kg-Expt 5).

The single dose of antisense drug produced a pH of 1.31+/−0.03 which is about the same as the saline (1.41+/−0.07 from expts 1 and 2) and antisense negative control 1.47+/−0.24 (5 mg/kg-Expt 5).

The volume of 0.1 M NaOH needed to titrate the gastric contents to pH7 for the single dose of antisense drug was 3.46+/−0.59 which is about the same relative to the saline (3.22+/−0.48 from expts 1 and 2) and antisense negative control 3.90+/−1.00(5 mg/kg-Expt 5).

This data shows that the antisense drug freeze thawed twice, and stored as outlined in expt 1, given by gavage once at 1.6 mg/kg does not work at 92 hours post dosing to reduce total H+ ions in the stomach. It is not clear whether a fresh batch of the drug at 1.6 mg/kg would have worked in reducing acid production at 92 hours. However, it would appear from this study and the effects of the drug at 5 mg/kg (Expts 1 and 2) also at 92 hours post dosing, that the effect of the test drug ARISA is dose dependent.

It is possible that an effect would have been observed at this dose of 1.6 mg/kg at a shorter time interval say at day 1 or 2 as observed with the second test drug ARAL 201 (see Expt. 6).

EXPERIMENT 6

Data from the Second Prototype Drug Testing ARAL 201

A 23 nmer antisense drug <u>GUGATA</u> TAG AT<u>A</u> AGG TAG GG<u>UGU</u> SEQ ID NO:6 which is specific to the rat gastric proton pump alpha chain loop 201 was made by Integrated DNA Technologies. This is a rat equivalent to one preferred prototype antisense drug to the human gastric proton pump alpha chain loop 195. The bold-underlined A's in the rat antisense drug differ in the human; in the human these A's would be G's. The underlined bases are 2' O methyl oligoribonucleoside phosphorothioates and the other bases are deoxynucleoside phosphorothioates.

The reagent was shipped as a powder and suspended in sterile normal saline at 5 mg/ml and used fresh.

The animal experiments were as described for the test antisense drug ARISA 1 in Experiments 1 and 2, except that 4 mg/kg of drug was used and different times looked at. Thirteen animals ranging in size from 155-175 mg received a 4 mg/kg oral dose by gavage (500 ul) on Tuesday. Five of the thirteen animals had their pylorus ligated on Friday i.e. at 68 hours or about 3 days. The remaining eight animals had their pylorus ligated on the following Tuesday i.e. about 7 days later. Another two animals received a 4 mg/kg oral dose by gavage (500 ul) on Monday and had their pylorus ligated 18 hours later on Tuesday. Acid collection was for 2 hours after pyloric ligation.

The volume of gastric acid, the pH of the gastric acid, and the volume of 0.1M NaOH needed to titrate the gastric contents to pH7 was determined.

The data for the antisense drug after 18 hours, 3 days and 7 days is reported below. The data is the mean +/− the standard error of the mean.

18 hour study—Gastric contents collection from 18-20 hours post dosing: The single dose of antisense drug after 18 hours produced a volume of gastric juice of 1.10 ml in one rat*. This is a much lower volume than that produced using a single dose of saline at 92 hours post gavage (4.62 ml+/−0.71 from expts 1 and 2) or single dose of antisense negative control 4.60+/−1.12 (5 mg/kg-Expt 5). This volume was also lower than the omeprazole volume data of 1.73+/−0.20 (Expt 3) and 1.83+/−0.10 ml (Expts 1 and 2) after one 1.725 mg/kg dose and five 3.45 mg/kg daily doses (92 hours post initial administration) respectively.

The single dose of antisense drug after 18 hours produced a pH of 5.6 in one rat* which is much higher than the single dose of saline at 92 hours post gavage (1.41+/−0.07 from expts 1 and 2) or single dose of antisense negative control 1.47+/−0.24 (5 mg/kg-Expt 5). This pH was higher than the pH obtained with omeprazole namely 1.78+/−0.20 (Expt 3) and 2.82+/−0.27 (Expts 1 and 2) after one 1.725 mg/kg dose and five 3.45 mg/kg daily doses (92 hours post initial administration) respectively.

The volume of 0.1 M NaOH needed to titrate the gastric contents to pH7 for the single dose of antisense drug after 18 hours was 0.15 ml in one rat*. This is much less compared to the single dose of saline at 92 hours post gavage (3.22+/−0.48 from expts 1 and 2) or single dose of antisense negative control 3.90+/−1.00(5 mg/kg-Expt 5). This volume is lower than the omeprazole data of 0.94+/−0.22 (Expt 3) and 0.74+/−0.11(Expts 1 and 2) after one 1.725 mg/kg dose and five 3.45 mg/kg daily doses (92 hours post initial administration) respectively.

3 day study—Gastric contents collection from 68-70 hours post dosing:

The single dose of antisense drug after 3 days produced a volume of gastric juice of 3.38+/−0.25 ml, which is reduced relative to the saline (4.62 ml+/−0.71 from expts 1 and 2) and antisense negative control 4.60+/−1.12(5 mg/kg-Expt 5). This is not as low as 1.73 and 1.83 ml obtained with omeprazole with one 1.725 mg/kg dose and 5 daily 3.45 mg/kg doses respectively.

The single dose of antisense drug after 3 days produced a pH of 1.36+/−0.11 which is the same as the saline (1.41+/−0.07 from expts 1 and 2) and antisense negative control 1.47+/−0.24 (5 mg/kg-Expt 5). This compares to the omeprazole pH data of 1.78 and 2.82 after one 1.725 mg/kg dose and 5 daily 3.45 mg/kg doses respectively.

The volume of 0.1 M NaOH needed to titrate the gastric contents to pH7 for the single dose of antisense drug after 3 days was 3.35+/−0.37 ml which is the same as the saline (3.22+/−0.48 from expts 1 and 2) and antisense negative control 3.90+/−1.00(5 mg/kg-Expt 5). This compares to the omeprazole data 0.94 and 0.74 ml after one 1.725 mg/kg 3.45 mg/kg dose and 5 daily doses respectively. 7 day study: The single dose of antisense drug after 7 days produced a volume of gastric juice of 4.76+/−0.35 ml, which is about the same relative to the saline (4.62 ml+/−0.71 from expts 1 and 2) and antisense negative control 4.60+/−1.12(5 mg/kg-Expt 5). This is not as low as 1.73 and 1.83 ml obtained with omeprazole with one 1.725 mg/kg dose and 5 daily 3.45 mg/kg doses respectively.

The single dose of antisense drug after 7 days produced a pH of 1.19+/−0.05 which is slightly reduced relative to the saline (1.41+/−0.07 from expts 1 and 2) and antisense negative control 1.47+/−0.24 (5 mg/kg-Expt 5). This compares to the omeprazole pH data of 1.78 and 2.82 after one 1.725 mg/kg dose and 5 daily 3.45 mg/kg doses respectively.

The volume of 0.1 M NaOH needed to titrate the gastric contents to pH7 for the single dose of antisense drug after 7 days was 4.74+/−0.54 which is slightly raised relative to the saline (3.22+/−0.48 from expts 1 and 2) and antisense negative control 3.90+/−1.00(5 mg/kg-Expt 5). This compares to the omeprazole data 0.94 and 0.74 ml after one 1.725 mg/kg dose and 5 daily 3.45 mg/kg doses respectively.

Summary: This data suggests that this test antisense drug ARAL 201 at 4 mg/kg can have a strong acid reducing effect at 18 hours (although one of the rats unexpectedly produced a result similar to saline*). ARAL at 4 mg/kg had only a slight effect at day 3 as observed by its capacity to reduce the volume of acid secretion but without significant effect on pH or the volume of NaOH needed to titrate the gastric acid to pH7. ARAL 201 had no observable effect on day 7 at 4 mg/kg.

The data with ARAL 201 suggests a time dependent effect at a 4 mg/kg dose. The action of ARAL at 4 mg/kg was not as prolonged as the action of ARISA at 5 mg/kg which had an effect at 92 hours post dosing (Expts 1 and 2). This data shows that not all the designed antisense drugs will work equally well on a per kg basis in reducing acid output, as is to be expected. Some may not work at all.

EXPERIMENT 7

A Single 3.45 mg/kg administration Of Omeprazole—Observations at Day 4

The animal experiments were as described for the test antisense drug ARISA 1 in Experiments 1 and 2, except that 3.45 mg/kg of omeprazole was given once intraperitoneally, and the effect on gastric contents looked at 92 hours post dosing. Briefly, five Long Evans rats were injected intraperitoneally once with 3.45 mg/kg of omeprazole solution on Monday. These rats did not receive any more daily injections. On the Thursday afternoon (5 pm), being the day before pyloric ligation, the animals were placed without food in special metabolic cages to minimize caprophagy. Thus the animals did not have food in their stomach on the Friday morning, being the time of pyloric ligation.

The animals were lightly anaesthetized and had their pylorus ligated on Friday. All the animals were allowed to recover, and then two hours later, anaesthetized and their gastric contents recovered before humanely euthanizing.

About 92 hours had passed from the initial ip administrations to the time the gastric contents were recovered.

Data from the Omeprazole Drug Testing

The volume of gastric acid, the pH of the gastric acid, and the volume of 0.1M NaOH needed to titrate the gastric contents to pH7 was determined.

The data is reported below. The data shown is the mean +/− the standard error of the mean.

One of the five rats had blood in the stomach following pyloric ligation. Blood in the stomach has a buffering effect and thus the data for it was excluded from the results.

The volume of gastric juice with a single 3.45 mg/kg ip omeprazole dose 92 hours prior to taking data was 5.27+/−0.43. This is the same as the 92 hour saline controls being 4.62 ml+/−0.71 ml standard deviation (from expts 1 and 2). The volume of gastric juice was reduced to 1.84+/−0.1 with a single dose of antisense drug ARISA, 92 hours post initial administration (Expts 1 and 2).

The gastric pH with a single 3.45 mg/kg ip omeprazole dose 92 hours prior to taking data was 1.27+/−0.05. This is the about the same as the 92 hour saline control which was 1.41+/−0.07 (Expts 1 and 2). The single dose of antisense drug ARISA increased pH to 1.80+/−0.12, at 92 hours post dosing (Expts 1 and 2).

The volume of 0.1 M NaOH needed to titrate the gastric contents to pH7 for the animals receiving a single 3.45 mg/kg ip omeprazole dose 92 hours prior to taking data was 4.46+/−0.40. This is slightly higher than the 92 hour saline control which was 3.22+/−0.48 (Expts 1 and 2). The volume of 0.1 M NaOH needed to titrate the gastric contents to pH7 for ARISA, the antisense drug at 92 hours post dosing was 1.34+/−0.37 (Expts 1 and 2).

This data shows that 3.45 mg/kg of omeprazole given once via ip, does not have any significant effect at 92 hours post dosing in the rat. Omeprazole has an effect at 1-3 hours post dosing at 1.725 mg/kg and at 92 hours after 5 daily 3.45 mg/kg doses where the last dose is given 1-3 hours before contents are taken**. In contrast the antisense drug ARISA given by gavage once at 5 mg/kg works well at 92 hours post dosing. The antisense drug works as well as five single 3.45 mg/kg daily intraperitoneal doses of omeprazole in reducing total H+ ions in the stomach in Experiment 1 or as well as one 1.725 mg/kg dose in Experiment 2.

**With omeprazole the volume of the gastric contents was 1.73+1-0.20 two hours after a single 1.725 mg/kg dosing (Expt 3) and 1.83+/−0.10 ml (Expts 1 and 2) after 5 daily 3.45 mg/kg doses (92 hours post initial administration) with the last dose being 2 hours before data was taken.

With omeprazole the pH was 1.78+/−0.2 two hours after a single 1.725 mg/kg dosing (Expt 3) and 2.82+/−0.27 (Expts 1 and 2) after 5 daily 3.45 mg/kg doses (92 hours post initial administration) with the last dose being 2 hours before data was taken. With omeprazole the volume of NaOH needed to neutralize the contents to pH 7 was 0.94+/−0.22 ml, when data was taken two hours after a single 1.725 mg/kg omeprazole dosing (Expt 3) and 0.74+/−O. 11 ml after 5 daily 3.45 mg/kg doses (92 hours post initial administration) with the last dose being 2 hours before data was taken.

The observation that omeprazole does not work in the rat 4 days (92 hours) post a single 3.45 mg/kg ip dosing is consistent with other reported data. In one study it was shown that following a dose of omeprazole that produces a maximal inhibition of acid secretion the effect lasts for about 13 hours in the rat (Larsson et al Gastroenterology 1983 October 85(4); 900-7). Others report effects observable at 24 hours post maximal dosing in the rat. The effect of maximal doses of omeprazole in rats is nevertheless significantly shorter than in other animals such as dogs where an effect is still observable for 3-4 days (supra) and in humans where an effect is observable for 3 days (Merck Index).

Extrapolating from the prior art experiences with interspecies variation on the length of action with a single dose of omeprazole described above, the rat data with 5 mg/kg ARISA 1 in Experiments 1 and 2, that shows an effect at 4 days, is expected to equate to a much longer effect in larger animals such as dogs and in humans, perhaps for about 1 week or more. Also the effects in the human and dog are likely to occur at a lower dose on a per kg basis than the rat because of metabolic rate difference.

A humanized antisense drug to the proton pump, such as one to the initiation site, is thus expected to work longer in humans than in the rat and at a lower dose on a per kg basis than in the rat.

It is noted the effect in the rat is also expected to be longer for the antisense drug ARISA at about 5 mg/kg and at higher doses; only one time point at 92 hours post dosing was investigated in Experiments 1 and 2. The strong 1(18 hour) and week 3 day effect in the rat is also expected to be longer for the antisense drug ARAL 201 at above 4 mg/kg doses.

EXAMPLE 2

Further Testing & Modifications of Lead Molecules Testing Alpha Stabilized Derivatives of Lead (Prototype) Drugs ARISA 1 for Long Action of a Week at Lower Doses Increased resistance may be obtained via alpha-oligonucleotides. Stabilization factors up to 200 fold can be achieved for alpha-oligonucleotides over beta-oligonucleotides via making the last two residues . . . T-C, . . . A-C, or . . . C-C, and intermediate stabilization is found via . . . G-A, . . . T-A, or T-T terminal sequences. The 23 nm er rat oligo ARISA 1 can be made a 21 nm er AAT TCA TAA TTC TCC TTC CCC (SEQ ID NO:23), an 18 nm er AAT TCA TAA TTC TCC TTC (SEQ ID NO:24) or a 15 nm er AAT TCA TAA TTC TCC (SEQ ID NO:25)

which finish with a C-C or T-C and made from alpha oligonucleotides.

The whole sequence may be alpha anomers such as deoxynucleoside phosphorothioates or 2'Omethyl oligoribonucleoside phosphorothioates alpha anomers or methyl phosphonate alpha anomers. Preferably there are at least four 2'Omethyl oligoribonucleoside phosphorothioates on either end as used herein Example 1 to reduce acid secretion with the last two on the 3' end being alpha anomers. Alpha anomers, like 2'Omethyl do not support Rnase H. A mixed strand alpha/beta type oligo can thus be made wherein there is at least about 4/5 beta type deoxynucleoside phosphorothioates to retain Rnase H activity. It will be understood that Rnase H activity may not be needed for an antisense to the initiation codon and may in fact not be wanted in some cases if there is non specificity associated with its action.

Self Stabilized Derivatives of Lead Drug ARISA 1 for Possible Long Action of a Week at Lower Doses Increased stability may be obtained via self stabilized derivatives by adding 3' loops to increase drug half life as described for instance by Tang et al Nucleic Acids Research 1993, vol 21 No 11, p 2729-2735.

The lead (prototype) antisense drug(s) ARISA can be self stabilized at the 3' end with a 4 nucleotide loop or preferably at least a 5-7 nucleotide loop and a stabilized stem of at least 6, or preferably 10 or more nucleotides. An 18 nm er of ARISA 1+8 base 3'extension that is self stabilized with a four base loop from bases 14-18 i.e. CTTC, and then an 8 base pair stem with base pairing will be as follows AAT TCA TAA TTC TCC TTC GAGAATTA (SEQ ID NO:26). The 8 base pair stem will be as follows

```
TAA TTC TC
ATTAAGAG
```

Self Stabilized Derivatives of Lead (Prototype) Drug ARAL 201 for Possible Long Action of a Week at Lower Doses A self stabilized prototype molecule such as ARAL 201 can be self stabilized at the 3' end with a 4 nucleotide loop or preferably at least a 5-7 nucleotide loop and a stabilized stem of at least 6, or preferably 10 or more nucleotides.

A prototype molecule made to the human alpha chain proton pump may be self stabilized in the following manner by making a 31 nm er GUG ATA TAG ATA AGG TAG GG UGU CCTACCTT (SEQ ID NO:27). In this molecule there is a four base loop from bases 19 to 23, GUGU, which is the 2' Omethyl oligoribonucleotide bases, and then an 8 base pair stem with base pairing as follows:

```
AAGGTAGG
TTCCATCC.
```

The latter bases may also be 2' Ol methyl oligoribonucleotide phosphorothioates.

Specificity Improvements

If any non specific interactions of the antisense drug to target messages of similar sequence occur, a self stabilized loop region can be made so that at least the loop region of the drug is unique and capable of binding but the stem contains any offending sequences that cause non specificity because of similarity to other target messages. Putting them in a stem means they are not as available for binding non specifically.

For antisense to the initiation codon, if non specificity is due to Rnase H then the deoxynucleotides phosphorothioates may be decreased to less than about 3 or all the molecules may be made 2'O methyl oligoribonucleotides. Alpha anomeric ribose can also be used when Rnase H is not essential for activity. Similarly methylphosphonate alpha type oligonucleotides could be used which do not support Rnase H. These methylphosphonates may also increase the safety profile of the drug and the therapeutic window. Alternatively the lead drug ARISA 1 or smaller versions can be made with morpholino phosphorodiamidates which do not require RNase H for activity.

Other Lead Drug Design

In examples 3 other lead drug design modifications are provided.

$K^+$ and Antisense Conjugates $K^+$ may be attached to the sugar at the 5' OH group and/or to the 3' OH group. Conditions can be chosen so that the OH groups at these sites become O− and then $K^+$ attached to them.

$K^+$ may also be attached to the phosphate backbone of the antisense. At each of the phosphorothioate bonds there will then be a potassium phosphorothioate bond.

These are all ionic-ionic interactions so that bonding should be strong enough to stay together. Attachment of $K^+$ to the phosphate backbone will also make the antisense molecule neutral as a whole.

Administering such an antisense drug will make gastric $K^+$ high which can directly influence acid levels. $Na^+$ (MW 11) which is smaller and has a greater charge density than $K^{+(MW\ 19)}$ may displace some of the $K^+$. Low salt diet could be used at the time of administration to minimize this.

Ethanol and Antisense Conjugates may Form Upon Mixing

Ethanol $CH_3\ CH_2\ OH$ is a week acid and can attach to the antisense drug via hydrogen bonding. It can attach to the sugar 5' OH and to the 3' end OH. It can also attach to the NH2 of the bases G and A which occur only in the keto form under physiological conditions. It will also attach to the OH of the enol form of the bases T and G at high. It will also attach to the OH of the phosphate backbone.

If 10% ethanol is given in admixture with the antisense drug it may have a direct effect on acid levels. When in the acidic environment it may attach to the T, G, of the antisense, and increase absorption of the antisense via the stomach. At physiological pH of the cell the ethanol may then come off, allowing the bases to operate in the usual base pairing or triples. The fact that ethanol denatures DNA should be taken into account when choosing an antisense or antigene drug.

Ranitidine and Antisense Conjugates

Ranitidine has a positively charged N+, which can be strongly bonded to the O– of the phosphate backbone. Ranitidine can thus be preferentially attached to the backbone via ionic bonds and not to the bases of the antisense drug to which there may be some hydrogen bonds. Thus conjugates should be able to find their complementary sequence.

EXAMPLE 3

Oligonucleotide Design (i) Antisense, Ribozyme, and Antigene Drugs to Human H+,K(+)-ATPase Alpha Chain Target H+,K(+)-ATPase Protein—Gene Expression H+,(K+)-ATPase is a constitutively expressed dimeric enzyme composed of an alpha and beta chain which chains are constitutively expressed by parietal cells. A 5' Sp1 binding site on the alpha gene promoter maintains basal transcriptional activity and is thought to control up to 80% of the transcription rate (Muraoka et al Am, J Physiol, December 271: 6 Pt 1 G1104-13). The alpha and beta chain message levels are coordinately expressed. The alpha chain protein is unique to the gastric proton pump, while the beta chain is shared by other proton potassium pumps and also the proton sodium pump. Thus, it is preferred for acid reduction to make a drug that targets the alpha chain, but depending on the pharmacokinetics a drug can be made to the beta chain of the gastric proton pump. For other treatments such as pernicious anaemia, it may be preferred to target the beta chain and or both alpha and beta chains.

The Nucleotide Sequences

An antisense, ribozyme, or antigene drug can be designed to the human H+,K(+)-ATPase alpha or beta gene or messages using the sequences available inter alia in the scientific literature, the four major public databases described on page 5. Also SWISS-PROT file 20648 has the alpha chain and File 51164 the beta chain protein sequences. Various publications and databases that refer to the same protein, message and the gene sequences have been sourced to confirm conservation of target sequences.

Specificity for the Alpha Chain

As described above a target site was chosen which is unique to the alpha chain mRNA as determined by similarity analysis.

The potential for similarity of the target nucleotide sequence to other ATPases was considered. The fact that the alpha chain contains the amino acid sequence around phosphorylated aspartate which is perfectly conserved in all ATPases and the consensus sequence is D-K-T-G-T-[L1]-T1 where D is phosphorylated was taken into account. This may be a region of high nucleotide sequence similarity with ATPase proteins whose sequence is known or has yet to be determined.

An antisense drug was made to the alpha sequence that minimized and preferably avoided binding to the non-gastric colonic and renal H+, (K+)-ATPase messages, which codes for related proteins that are important for absorption of K+ from the gastro-intestinal tract or urinary tract (Jaisser F Nephrologie 1996, 17:7 401-8). They are encoded by a different alpha chain and share the beta chain. The antisense drug to the gastric proton pump alpha chain was chosen to minimize and preferably not bind to any similar parts of the Na+/K(+)-ATPase which has a different alpha chain but shares the beta chain. The alpha chain of the colonic and renal H+, (K+)-ATPase and the Na+/K(+)-ATPase sequences are sufficiently different at the nucleotide sequence to enable most antisense drugs to be made specific to the gastric proton pump alpha chain using techniques known in the art.

Most antisense drugs are best made to a region of RNA that has high probability of being physically accessible to the antisense as determined for instance by knowhow, and/or secondary structure determinations as determined by using various computer software programs such as those described by Zucker and Stiegler 1981 NAR 9 133-148 and Zuker 1989 Science 244, 48-52 and more recent publications).

Knowhow derived from the experiments in the present invention teaches that the initiation site is one particularly preferred site in the human message. As shown in Example 1, an antisense drug to the initiation site of the gastric proton pump in the rat works to reduce acid secretion. The initiation site in the human gastric proton pump alpha chain is thus also likely to be a suitable site as it has high probability of being physically accessible.

Computer software programs used for mRNA secondary structure determinations often have default settings for various parameters that can be Adjusted. Changing the default settings alters the secondary structure determinations. A finite number of different alternative structures can be determined for the one message using known alternative settings in the art and/or by submitting the sequence to the mfold server. This can be used to determine which regions of the mRNA are best targeted when secondary structure of the mRNA is important to the effectiveness of the antisense. This is done in the next section below.

Some antisense drugs such as the ones made of morpholino phoshorodiamidates are known in the art to act best by blocking translation of the targeted mRNA by binding near the start codon and/or by interfering with exon-intron processing by binding to exon-intron boundaries. The secondary structure of the mRNA target site may be less important using antisense drugs made from these nucleotides. At least a very small single stranded region is preferable for nucleation pairing by the antisense.

Antisense sequences to the target human mRNA alpha chain proton pump generated using one group of settings and to the initiation codon. The secondary structure of the whole human alpha chain proton pump mRNA was determined according to RNA draw software program based on Zuker secondary structure analysis developed by Ole Matzura (Dept Medical Biophysics Karolinska Inst S-171 77 Solna Sweden) as an example only. When the default settings were used the human alpha chain molecule had 263 loops (hairpin, internal and bulge types) wherein loop 1-4 are in the short 30 base 5' untranslated region, loops 5 to 227 are in the coding region, and the remaining loops are in the 3' untranslated regions. These above identified loops are used herein as a reference point for distinguishing the different target sites for antisense drugs to the human message and comparing them to loops in the rat message.

Using information generated from the secondary structure determinations of the human mRNA using the one group of default settings, a list of candidate antisense drugs was made that satisfied antisense design criteria such as no or low intermolecular and intramolecular bonding.

Other drugs were also chosen based on knowhow from the present experiments in Example 1 that the initiation site is likely to be a good target site. The list of designed antisense drug sequences is provided in Table 1 below.

It will be understood however that this is not a comprehensive list of drugs likely to work, because intermolecular and intramolecular bonding can be minimized by for example putting self stabilizing loops, and/or by circularizing antisense. Also other drug sequences can be chosen based on other different default settings and/or using probabilities that a particular site is free as determined using the mfold server or knowhow.

It will also be understood by those skilled in the art from practical experience, that not all antisense drugs designed will work despite designing to optimize the probability of working. There may be about a 12-80% chance of working or less depending on the skills of the designer and of the ones that work about a third may work more optimally and a third will work at an intermediate level.

Agents that are directed to the initiation site, loop 195, and to the 3'untranslated region may be trialed first or another order of trialing can be chosen, based on the antisense not forming any intermolecular or intramolecular bonding, or that the targeted sequences are conserved across species such as in the dog or rat.

It will be understood that T and U are interchangeable depending on whether DNA or RNA is used e.g. deoxynucleotide phosphorothioate (T) or oligoribonucleotide phosphorothioate (U) respectively.

TABLE 1

ANTISENSE DRUGS RATIONALLY DESIGNED TO THE HUMAN PROTON PUMP ALPHA CHAIN MESSAGE

| Loop number(s) | Nucleotides | Antisense size | Comments |
|---|---|---|---|
| (a) 6, 7, and 8<br>CAT AGT TCT C GGC CTT CCC CAT<br>(SEQ ID NO:17) | 1-22 | 22 mner | initiation site |
| CAT AGT TCT CGG CCT TCC CC<br>(SEQ ID NO:18) | | 20 mner | +/- alpha anomer end |
| CAT AGT TCT CGG CCT TCC<br>(SEQ ID NO:19) | | 18 mner | +/- alpha anomer end |
| CAT AGT TCT CGG CCT<br>(SEQ ID NO:20) | | 15 mner | +/- 14 mner if alpha anomer end |
| (b) 195<br>GGT GAT GTA GAT GAG GTA GGG<br>(SEQ ID NO:28) | 2398-2418 | 21 mner | conserved across species in the dog and rabbit; directed to coding region |
| (c) 1 91 + part of 90<br>UCU UCU CGU UUU CCA CCC CC<br>(SEQ ID NO:29) | 858-877<br>858-880 | 20 mner | directed to coding region |
| GTG UCU UCU CGU UUU CCA CCC CC<br>(SEQ ID NO:30) | 856-877 | 23 mner | |
| UCU UCU CGU UUU CCA CCC CC GA<br>(SEQ ID NO:31) | 856-880 | 22 mner | |
| GTG UCU UCU CGU UUU CCA CCC CC GA<br>(SEQ ID NO:32) | | 25 mner | |
| (d) 204 + pt 203<br>CAG GGA CAC AGA UGG GAA A<br>(SEQ ID NO:33) | 2481 to 2499 | 19 mner | directed to coding region |
| (e) 204<br>AGA UGG GAA AAU GUC AGU<br>(SEQ ID NO:34) | | 18 mner | directed to coding region |
| (f) 248<br>UAA GUU CAG AAA CAC CC<br>(SEQ ID NO:35) | 3407-3423 | 17 mner | 3' untranslated region |
| (g) 184<br>CAU UUU UGG CAG CAU CUC<br>(SEQ ID NO:36) | 2249 to 2266 | 18 mner | directed to coding region |
| (h) 189<br>CAA AGU UGU CAU CCA<br>(SEQ ID NO:37) | | 15 mner | directed to coding region |
| CAA AGU UGU CAU CCA G<br>(SEQ ID NO:38) | | 16 mner | |

TABLE 1-continued

ANTISENSE DRUGS RATIONALLY DESIGNED TO THE HUMAN
PROTON PUMP ALPHA CHAIN MESSAGE

| Loop number(s) | Nucleotides | Antisense size | Comments |
|---|---|---|---|
| (i) 227<br>CTA AUA GUA GAG UUC C<br>(SEQ ID NO:39) | 3141 to 3156 | 16 mner | directed to coding region<br>targets termination codon |
| (j) 213<br>TGA AGT AGT CAG TGA AGC<br>(SEQ ID NO:40) | 2627-2645 | 18 mner | directed to coding region<br>16 mner |
| A AGT AGT CAG TGA AGC<br>(SEQ ID NO:41) | | 16 mner | |
| (k) 66<br>TGG CGA TGA TGT TGG T<br>(SEQ ID NO:42) | 496 to 511 | 16 mner | conserved in the rat<br>directed to coding region |
| (l) 150<br>GCT AGA TGG AAA CTT C<br>(SEQ ID NO:43) | 1818 to 1836 | 16 mner | directed to coding region |
| AGGCC GCT AGA TGG AAA GTT C<br>(SEQ ID NO:44) | 1818 to 1841 | 21 mner | |
| (m) 155<br>CAC AGC AUG AGG GAC<br>(SEQ ID NO:45) | 1888 to 1902 | 15 mner | directed to coding region |
| (n) 162 and 163<br>GGG CAC ACG GAG GCG G<br>(SEQ ID NO:46) | | 16 mner | directed to coding region |
| (o) 186<br>CGA UGC GCC CAA UGA U<br>(SEQ ID NO:47) | | 16 mner | directed to coding region |
| (p) 92 + 43<br>AUA AAA AAU GUG GCA CCG<br>(SEQ ID NO:48) | | 19 mner | directed to coding region |
| (q) 93<br>CAC AUG GCC ACA AUA AAA AAU<br>(SEQ ID NO:49) | | 21 mner | directed to coding region |
| (r) 112<br>GUG GUG UCA GCU GUG U<br>(SEQ ID NO:50) | | 16 mner | |
| (s) 151<br>UGA UGG GGU GGU C<br>(SEQ ID NO:51) | | 13 mner | directed to coding region |
| (t) 210<br>CUU GUA GGU GGU GGU CC<br>(SEQ ID NO:52) | | 17 mner | directed to coding region |
| (u) 228<br>UUG AAG GCA GUC GUC CC<br>(SEQ ID NO:53) | 3110-3126 | 17 mner | after the stop codon, in<br>the 3' untranslated region. |
| (v)<br>TT GCT CAG ATA TCA<br>(SEQ ID NO:54) | | 14 mner | |

Table 1 lists a number of antisense drugs designed to the Human gastric proton pump initiation site. Some of the best antisense drugs are designed around the initiation site to interfere with ribosome attachment and/or translation initiation. These do not need to incorporate the ATG initiation methionine codon and may be just downstream or upstream of this site. If there are any non specificity problems associated with Rnase H activity then 2' O methyl bases may be used throughout or for all but 1-3 bases over the problem region.

It is expected from the rat experiments that the initiation site will be accessible to the ribosome and thus also the antisense drugs. Also preceding the AUG site at −1, −2 and −3 on the mRNA, there is a potential loop, which may allow for some better access to the site for drugs that interfere with ribosome attachment.

An antisense drug to the initiation site comprising at least some of the first about 12-13 nucleotides from the 3' end to reaches the first exon-intron boundary splice site and may provide the possibility of affecting processing of the pre-mRNA.

Other drug(s) to the 30 base 5' UT region and including the cap site may be good targets. Antisense drugs to the initiation and 5'UT region may work even though they are not optimal with regard to low intermolecular and intramolecular binding.

A small antisense sequence e.g. 15 nm er may work well when directed to the initiation sites or perhaps a 5' or 3' untranslated region. Smaller and longer versions of these drugs will also work; preferably longer versions do not impact significantly on intermolecular and/or intramolecular binding. Antisense drugs bigger than about 17-20 nm ers may also be long enough to provide another mechanism of action, namely blocking ribosome translocation in the coding region and thus mRNA translation.

One preferred type of antisense drug has four 2'O methyl ribonucleoside phosphorothioates on either end and the inner bases are deoxynucleoside phosphorothioates, so that it supports Rnase H degradation of the message.

The above identified antisense drug sequences and chemistry should provide favourable pharmacokinetics, general stability to nucleases, some stability via the oral route of administration, efficacy in some cases, and potentially long action as shown in Example 1 for the rat drug.

When designing smaller versions of long antisense drugs or small antisense drugs, it is possible to make the following modifications in order to increase affinity to the target site:

(i) change the deoxynucleoside phosphorothioates to more 2' O methyls (but keeping at least about 4-5 if necessary or preferred to keep Rnase H activity), (ii) use all 2' O methyl if the drug does not need to work via Rnase H (iii) use high affinity C and/or T propynyl bases or methylcytosine instead of the natural nucleobases; or (iv) extend the length of the antisense drug incorporating (most of) the chosen sequence and a few other nucleotides e.g. an additional 6 nucleosides; preferably the latter added nucleotides do not impact significantly on intermolecular and/or intramolecular binding.

Part or all of the antisense drug may be used as one half of two overlapping 9 mners. This may be appropriate for some of the smaller antisense drugs e.g. the 13 nm er-16 nm ers.

Humanized Antisense Drugs Corresponding to Rat Antisense Drug Sequences (Table 4) Generated Using the Same One Group of Settings The secondary structure of the rat proton pump alpha chain was determined using the default settings used for the human proton pump mRNA from which the list of designed antisense drugs in Table 1 were derived. Rat antisense drugs were then designed as outlined above for the human proton pump alpha chain, with low intermolecular and intramolecular binding among other parameters being assessed. These rationally designed rat antisense drug sequences are listed in Table 4.

The humanized versions of some of these rat antisense drugs that are considered appropriate candidates for testing are in Table 2 below; Unless otherwise stated the regions targeted are to coding sequences.

TABLE 2

| | |
|---|---|
| CAT CTC CTT CTT CAT GTT CTC (SEQ ID NO:55) | to base 129 etc (same 21 mner as the antisense to rat) |
| TAG TCC TTC TCA TTC AGG TAG A (SEQ ID NO:56) | to base 1706 etc (same 22 mner as the antisense to rat) |
| TGG AA<u>G</u> TAG GA<u>G</u> TA<u>G</u> GCA (SEQ ID NO:57) | to base 2683 etc (18 mner) (four bases differ from rat as shown) |
| <u>GAG</u> AGA <u>CGC</u> TGA GGA <u>CAG</u> T (SEQ ID NO:58) | to the 3' untranslated region of the human (19 mner) (9 bases differ from rat) |

The above identified humanized antisense drug sequences are good candidate antisense drugs for trialing. Although the secondary structure of the human mRNA at the regions referred to above was not as optimal as the human sequences targeted by the antisense drug in Table 1, this is thought to not be as critical as the actual sequence of the antisense and whether it forms significant intermolecular or intramolecular structures. Thus the above identified humanized antisense drugs are also good candidate antisense drugs for testing in vitro and in humans. The first two drugs may be trialed in the rat animal model because they are the same. The drugs are best trialed in human parietal cell cultures or using a human embryonic stomach model described below.

The above is not a comprehensive list, but is merely used to show another means of designing. Other humanized antisense versions of the rat sequences referred to in Table 4 will also be suitable for testing.

Antisense Sequences to the Target Human mRNA Alpha Chain Proton Pump Generated Using Many Alternative Settings It is possible to determine the likelihood of secondary structure at any particular base in the human gastric proton pump alpha chain by submitting the human alpha chain proton pump mRNA sequence to the mfold server. Because the human gastric proton pump sequence is longer than 3000 bases, the maximum one may submit at any time, it is necessary to crate a 3000 base region beginning at each of the 5' and 3' ends which will have overlapping regions. Suitable regions with low probability of secondary structure can be determined as done for an reported for the corresponding rat sequence below. Then human gastric proton pump antisense sequences made to these same target regions according to the preference for no or low intermolecular and intramolecular bonds and certain preferred size oligonucleotide drugs depending on the mechanism of action.

The availability of this more detailed secondary structure information for each base can also be used to improve the antisense drugs such as increase the size of some of the smaller antisense drugs referred to above in Table 1 when they target the coding region.

Other Humanized Antisense Drugs Corresponding to Rat Antisense Drugs Generated Using the Many Alternative Settings The secondary structure of the rat proton pump alpha chain was determined by submitting the first 3000 bases of the rat sequence to the mfold server at http:mfoldi.wustl.edu/-mfold/rna/formi.cgi. The ATG initiation codon is at base 207-209. The human gastric proton pump sequence is longer than 3000 bases, and starts at nucleotides −30 i.e. equivalent to base 177 in the rat.

The likelihood of secondary structure at any particular base in the rat gastric proton pump alpha chain was used as a basis to make a list of target regions in the rat message. Antisense can be made to some of these regions, with the preferred ones having low intermolecular and low intramolecular binding.

Suitable human antisense drugs could be made equivalent to these rat antisense; optimized for no or low intramolecular and intermolecular binding according to the human specific sequence. It will be understood that other means exist to also limit unwanted intermolecular and intramolecular bonding, such as self stabilization and circularization, which makes other target sites on the message suitable for binding oligonucleotide and modulating acid secretion.

Other Designed Antisense Drugs

Alpha Stabilized Derivatives of the Antisense Drug to the Initiation Codon for Potentially Longer Action.

Increased resistance may be obtained via alpha-oligonucleotides. Stabilization factors up to 200 fold can be achieved for alpha-oligonucleotides over beta-oligonucleotides via making the last two residues . . . T-C, . . . A-C, or . . . C-C, and intermediate stabilization is found via . . . G-A, . . . T-A, or T-T terminal sequences. The antisense drug to about the initiation codon may be a 20 nm er CAT AGT TCT CGG CCT TCC CC (SEQ ID NO:18) or 18 nm er CAT AGT TCT CGG CCT TCC (SEQ ID NO:19) or 14 nm er CAT AGT TCT CGG CC (SEQ ID NO:21) each of which finish with a C-C.

The whole sequence may be alpha anomers such as deoxynucleoside phosphorothioates or 2'Omethyl oligoribonucleoside phosphorothioates alpha anomers or methyl phosphonate alpha anomers. Preferably there are at least four 2'Omethyl oligoribonucleoside phosphorothioates on either end as used herein in Example 1 to reduce acid secretion with the last two on the 3' end being alpha anomers. Alpha anomers, like 2'Omethyl do not support Rnase H. A mixed strand alpha/beta type oligo can thus be made wherein there is at least about 4/5 beta type deoxynucleoside phosphorothioates to retain Rnase H activity. It will be understood that Rnase H activity may not be needed for an antisense to the initiation codon and may infact not be wanted in some cases where there is the possibility of non specificity associated with its action.

Exon-Intron Boundary

One particularly preferred antisense drug targets the first exon-intron boundary which is 13 bases 3' of the initiation codon in the gene. The sequence of this boundary is as follows.

. . . ATG GGG AAG GCC-GTGAGT GG. (SEQ ID NO:59)

The base pairs shown in bold are in exon 1 with the ATG start of translation site in italix. The other bases are intron 1 and the hyphen (−) shows the splice site. The underlined part of intron 1 is the 5' donor junction of the intron. An antisense drug may be made complementary to part of the above sequence. It may be complementary to sequences near the boundary, up to and including the boundary or overlapping those boundary sequences. Preferably the antisense sequence comprises part of the 20 mner listed below which drug has appropriate low intermolecular and intramolecular bonding.

CC ACT CA C G* GC CTT CCC CAT (SEQ ID NO:60)

* shows that the corresponding rat antisense sequence has a T instead of a G* (SEQ ID NO:61).

This drug may also be extended a few bases to interfere with ribosome attachment and/or ribosome translocation and may also act by Rnase H degradation of the (pre)message if it is made of similar materials as used for the rat drugs that have been shown herein to work in acid reduction in Example 1. It should be noted that the above sequence shares the first thirteen 3' bases with the antisense drug(s) to the initiation codon shown below with the underlined bases being conserved between the two:

CAT AGT TCT C GGC CTT CCC CAT (SEQ ID NO:12)

Cap Site Drug and 5' UT Region

Other antisense drugs can be made to the known cap site present or the 30 base 5'Untranslated region, as is known to work in the art to interfere with ribosome attachment, and processing of the message. This 5' Untranslated sequence is:

TGT TGG GTG GGA GCA CAG GCA CCG GGC ACC (SEQ ID NO:62)

Preferably, an antisense drug to the cap site will have low or no intramolecular and intermolecular binding. Thus one preferred antisense is the 25 nm er: CCC GGU GCC UGU GCU CCC ACC CAA CA (SEQ ID NO:63) directed to the first 25 bases of the 5'Untranslated sequence.

A Self Stabilized Antisense Drug Directed to the Human Alpha Chain Proton Pump Loop 195—is Shown as an Example of Another Way to Increase Stability The antisense drugs can be self stabilized by adding 3' loops to increase its half life as described for instance by Tang et al Nucleic Acids Research 1993, vol 21 No 11, p 2729-2735. A few self stabilized derivatives further self stabilized at the 3' end with a loop can be made and tested. A self stabilized prototype molecule may have a 4 nucleotide loop or preferably at least a 5-7 nucleotide loop and a stabilized stem of at least 6, or preferably 10 or more nucleotides.

A prototype molecule GGT GAT GTA GAT GAG GTA GGG (SEQ ID NO:28) made to the loop 195 of the human alpha chain proton pump may be self stabilized in the following manner by making a 29 nm er GGT GAT GTA GAT GAG GTA GGG ACCTCATC (SEQ ID NO:64). In this molecule there is a four base loop from bases 17 to 21, AGGG, and then an 8 base pair stem with base pairing as follows:

```
GAT GAG GT
CTA CTC CA.
```

Rational Design of Morpholino Phoshorodiamidates to Human Gastric Proton Pump Alpha Chain mRNA Some criteria for selecting antisense sequences using morpholinos phosphorodiamidates are described in the Gene Tools web site the contents of which are incorporated by this reference. Other criteria are described elsewhere in the scientific and patent literature and/or can be gleaned from in this document.

The morpholino phosphorodiamidates are known in the art to act best by blocking binding of ribosomes, translation of the targeted mRNA and/or to work at exon-intron boundaries. When rationally designing, the secondary structure of the mRNA target site may be less important using antisense drugs made from these nucleotides although it may be preferable to have a small single stranded region for nucleation pairing by the antisense. The intramolecular and intermolecular bonds of the antisense drug itself is however usually important for best effect. Preferably the antisense should form no more than 4 contiguous intrastrand base pairs although 4 contigous base-pairs may be undesirable if all four are G:C pairs. The antisense drug may be a 23 nm er or a 25 nm er. Preferably the uracils are switched to thymines. Preferably the oligonucleotide does not contain over about 36% guanines or more than 3 contiguous guanines.

Regions from the 5' Cap to about 25 bases 3' to the AUG translation start site of the human gastric proton pump are likely to work when targeted with morpholino antisense with some antisense working well.

In the 5' Cap region the above identified 25 nm er antisense, made from morpholino phosphorodiamidates, namely CCC GGU GCC UGU GCU CCC ACC CAA CA (SEQ ID NO:63)meets these criteria. Preferably the uracils are switched to thymines at thus the antisense is CCC GGT GCC TGT GCT CCC ACC CAA CA (SEQ ID NO:65).

A morpholino version of the above identified antisense drugs directed to the human initiation codon preferably also incorporating the first exon-intron region are expected to work particularly well.

The 22 nm er antisense drug CAT AGT TCT C GGC CTT CCC CAT (SEQ ID NO:12) is to the initiation site comprising at least some of the first about 12-13 nucleotides from the 3' end to reach the first exon-intron boundary splice site. In this latter way it may provide the possibility of affecting processing of the pre-mRNA which is a mechanism of action of morpholino drugs.

A 23 nm er, 24 nm er and 25 nm er further comprising G (SEQ ID NO:13),

GG (SEQ ID NO:14), or GGT(SEQ ID NO:15) respectively are expected to be work effectively. The 23, 24 and 25 nm er CAT AGT TCT CGG CCT TCC CCA TGG T (SEQ ID NO:15) should work despite not being as optimal as the 22 nm er with regard to intermolecular and intramolecular binding.

It is expected from the rat experiments that the initiation site will be accessible to the ribosome and thus also the antisense drugs. Also preceding the AUG site at −1, −2 and −3 on the mRNA, there is a potential loop, which may allow for some better access to the site. The preferred antisense oligonucleotide may be smaller than that described as optimal at the Gene—Tools web site. Preferably the antisense oligonucleotide is also modified at either one or both of the 5' and 3' end to provide for improved long action.

Targeting Exon_Intron Regions

Forty two other morpholino antisense drugs can also be made to overlap the exon intron boundaries of the pre-mRNA. There are 22 known exons, with the sixth exon not been separated by an intron, and thus 41 exon-intron boundaries on the pre-mRNA of the human gastric proton pump alpha chain gene and another two boundaries between exons and 5' and 3' gene regions. Possible advantages of a morpholino phosphorodiamidate are as follow. Since the morpholino phosphorodiamidate does not work via an RNase H mechanism of action it is expected to cause fewer non specific effects in interfering with the proton pump. It should also have a better safety profile.

Other advantages include that the morpholino agents may work at lower doses and they may not be easily degraded once inside the cell. Thus the particularly long half life of the parietal cell may allow for a particularly long action, of a week, fortnight, or month, or even a few months using morpholino phosphorodiamidate.

Shotgun Design of Antisense Drugs to the Human Gastric Proton Pump Alpha Chain mRNA An alternative to rational design is shotgun designed drugs. Oligonucleotide synthesizers can synthesize 150 nucleotides at a time. The human proton pump sequence alpha chain available is 3759 bases. Thus 150 antisense each about 25 nucleotides long can be made to cover the whole human proton pump alpha chain sequence end to end.

They can be made with four 2' O methyl ribonucleotide phosphorothioates on each end and an inner core of deoxynucleotide phosphorothioates which chemistry as shown in Example 1 work to reduce acid secretion. These drugs will work interalia via Rnase H and at 25 nucleotides are also long enough for a high enough melting temperature to be able to interfere with ribosome translocation under monovalent cation conditions of parietal cells.

Forty two other antisense drugs can also be made to overlap the exon intron boundaries of the pre-mRNA. There are 22 known exons, with the sixth exon not been separated by an intron, and thus 41 exon-intron boundaries on the pre-mRNA of the human gastric proton pump alpha chain gene and another two boundaries between exons and 5' and 3' gene regions.

These about 200 oligonucleotides may be made and tested in cell cultures of human parietal cells or other cells transfected with the human proton pump alpha chain gene or cDNA or in (transgenic) animals in pyloric ligation models as described in Example 1 for the rat. Moreover, they may be tested in "nude" animal models wherein a human embryonic gastric xenograft is present as described in Infect Immunol 1999 April 67(4): 1798-805 and Antimicrob Agents Chemother 1999 August: 43(8):1909-13.

For ones that work in in vitro and/or in vivo systems, shorter and longer versions of the effective ones can be made to optimize the effect. These shorter and longer versions can be made by rational designing the antisense drug as described above or randomly as described herein to determine the best sequence. The chemistry may also be modified to include 2'-O methoxyethyl sugars with methyl cytosine bases. A significant number of the ones that work in vitro are also expected to work in vivo in humans.

Ribozyme Drugs to the Human Alpha Chain mRNA

Ribozymes may be made to the human alpha chain mRNA. As described below they may be stabilized using a chemistry similar to the antisense oligonucleotides shown to work in Example 1 by modifying the arms that recognize the target mRNA sequence, and even changing parts of the catalytic unit, provided in the latter they are not essential for catalytic activity. Such ribozymes may act quicker than antisense drugs in degrading the target sequence and/or may provide savings in dose if appropriately stabilized and formulated or delivered specifically to the parietal target cells for instance by transfection directly or using a vector for expression in the cell.

The catalytic unit: There are a number of different catalytic units and each may recognize the same or different base sequences. The hammerhead catalytic unit may be the 22 base sequence CUGAUGAGUCCGUGAGGACGAA (SEQ ID NO:66) of the Haseloff-Gerlach ribozyme or a variant as described in WO95/06764 or a variant of the consensus CUGANGAGNCN*NGNCGAAAC (SEQ ID NO:67) where * forms a loop.

The catalytic sequence may be the hairpin unit identified by Hampel e.g. AUGGUCCAUUAUAUGGUGUUGCACA-CAAAGAGACCA (SEQ ID NO:68) or a smaller hairpin (Hampel et al NAR 18 299-304) or other ribozymes that work optimally at physiological temperatures where the conserved sequences are those surrounding the hairpin structure.

A hammerhead catalytic unit may cleaves GUU, GUC, and GUA on the mRNA, the cut being after the 3' U, C, or A respectively in the mRNA. A typical site is GUC.

A Hampel catalytic unit may cleave similar sites such as GUC where the cut is before the 5'G.

Recognition and specificity to the mRNA: A hammerhead type cleaving unit which cuts after the 3° C., A, or T base can be used with a 6 base or preferably bigger about 8 base mRNA recognition sequence on either side of the cleaving unit. Preferably the ribozyme has a binding site on the message which together with the GUU, GUC, GUA, cleavage site is specific to the alpha chain. Preferably the GUU, or C or A cleavage sites in the alpha message and the surrounding region of at least 6 to 8 bases chosen, is conserved in humans as determined by conservation cross species in related alpha chains.

Rational Ribozyme Design

A hampel type cleaving unit may have the recognition unit more 3' to the catalytic unit, wherein the recognition unit is on either side of the cleavage site on the substrate.

mRNA target site—secondary structure: A region of RNA may be chosen that is physically accessible to the ribozyme as determined for instance by secondary structure considerations (Zucker and Stiegler 1981 NAR 9 133-148 and Zuker 1989 Science 244, 48-52) as applied using various computer software programs. However, this may be predictive of in vitro activity rather than in vivo activity and thus other sites are expected need testing as described in the shotgun approach below. The 3' Untranslated region may be targeted generally by a shotgun approach or the whole molecule may be targeted this way.

The ribozyme—intermolecular and intramolecular binding: It is important for there to be low intramolecular binding of the recognition sequence to the hammerhead catalytic sequence so that the hammerhead catalytic unit forms. Similarly the recognition sequence preferably has low intramolecular and intermolecular binding to other ribozymes.

The ribozyme-mRNA binding: If the ribozyme is greater than 30 nucleotides then fast association kinetics is preferred although, this is usually more predictive of in vitro activity The chemistry: Ribozymes may be made using any of the known chemistries known in the art. Preferably, as indicated above for antisense drugs that have worked in acid reduction, however, one may make a fully RNA ribozymes more nuclease and perhaps also acid resistant and capable of reaching the parietal cell by using deoxynucleotide phosphorothioate ends or preferably 2' modified oligoribonucleotide phosphorothioate ends. One may use at least two and perhaps four or more 2'-O-methyloligoribonucleotide phosphorothioates at both the 3'end and the 5' end where these ends are in the hybridizing arms. One may also add 2' propyl or other 2' modifications to the 5'and 3' ends keeping the central bases RNA.

One may increase the nuclease and perhaps acid resistance by also modifying the catalytic unit to comprise deoxynucleoside phosphorothioates or 2'Omethyl or other 2'modifications provided the nucleotides changes are in regions non essential for ribozyme activity. For a hammerhead ribozyme, all but about 4-6 non-contiguous nucleotide positions in the catalytic unit may be changed as is known in the art. One may also use 2' Omethyl oligoribonucleotide phosphorothioates but preferably not in the 4-6 base catalytic region essential for ribozyme activity.

Other efficacy improvements may be provided by using a 3' nucleotide cap or inverted thymidine as disclosed in the prior art J. Biol Chem 1995 Oct. 27; 270(43); 25702-8.

Affinity and nuclease resistance and efficacy may be improved by any one or more of the alternative known improvements in chemistry or via other facilitators of activity. Some other improvements are described in WO95/06764 the contents of which are incorporated by this reference.

Two Prototype hammerhead ribozyme sequences: Two prototype ribozymes to the 3'Untranslated sequence of the proton pump with hammerhead catalytic units have been designed as examples only.

The 42 nm er AGUCCUAAGcugaugaguccgugaggac-gaaCAGAAACACCC (SEQ ID NO:69) binds to base 3468 in the human sequence which corresponds to the base 300 in the 3' untranslated region.

The 35 nm er GGCTGGcugaugaguccgugaggac-gaaCTCTTGG (SEQ ID NO:70) binds to base 96 to 110 in the 3' untranslated region which corresponds to base 3262 to 78.

Preferably at least four of the 5' end and 3' end nucleotides will be 2'-O-methyloligoribonucleotide phosphorothioates and the other bases in the recognition arms shown in capitals will be similarly modified oligoribonucleotide phosphorothioates or deoxynucleoside phosphorothioates. The catalytic unit may also be deoxynucleoside phosphorothioate and/or 2'Omethyl oligoribonucleoside phosphorothioate except where the bases must be RNA to remain active as is known in the prior art.

As well as or instead of using these nucleotide modifications, formulations may also be used to stabilize the ribozymes for administration as is known in the art.

Once a lead ribozyme molecule is identified mutational selection can be used to improve the catalytic efficiency of the ribozyme under physiological conditions according to U.S. Pat. No. 5,616,459 or as is known in the art.

Shotgun approach to making Ribozymes to the proton pump: In one shotgun approach a hammerhead catalytic unit can be made to cut any one of the approximately fifty GUU, GUC, or GUA target cleavage sites present in the coding region of the alpha message or similar sequences in the 5' or 3' untranslated region of the transcript.

Ribozymes may be made with 6 base and preferably 8 base recognition units to recognize any of these cleavable sequences present in the proton pump alpha chain message and trialed in vitro and/or in appropriate animal models such as described above for antisense drugs. Depending on the catalytic unit some ribozymes work in vivo when they do not work in vitro and vise versa.

Miscellaneous: Neomycin and perhaps other aminoglycoside antibiotics are observed to interfere with some ribozymes (Stage et al, RNA 1995 March, 1:1, 95-101). Ribozymes may be tested for the catalytic activity in the presence and absence of antibiotics likely to be used in *H. pylori* eradication therapy. Ribozymes should preferably also be tested for long term storage stability beyond six months.

Once a lead ribozyme molecule is identified mutational selection can be used to improve the catalytic efficiency of the ribozyme under physiological conditions according to U.S. Pat. No. 5,616,459.

Antigene Drugs to the Human Alpha Chain Gene

Antigene oligonucleotide drugs can be made to work via the duplex or triplex method or by the sense approach.

The ones that work via the duplex or triplex method will potentially be usable at even lower doses than antisense or ribozyme drugs to the message, because there is only one gene per cell whereas there may be 15, 300, 1000, or more messages per cell depending on the abundance of the message. For the parietal cell proton pump mRNA, there are likely to be about 1000 mRNA/cell. For a duplex or triplex agent, it is usually only necessary to make the antigene sequence bind two bases needed for a transcription factor or other factor to interfere with binding and gene expression.

For the antigene drugs that work via the sense approach the amount of drug needed may depend on the abundance of the transcription factor in the target cell.

Target sites—Sp1 binding site(s): More than about eighty percent of the gastric proton pump basal transcription levels and thus possibly acidity, is controlled through Sp1 binding to the alpha gene promoter. Sp1 is a ubiquitous factor which increases transcription by RNA pol II, 10-50 fold from promoters that contain one or more hexanucleotide sequence, 5' GGGCGG 3', or its complementary sequence, 5' CCGCCC 3', called GC boxes. It may be easy for treating or preventing some acid related conditions to completely interfere with this increased transcription. In the human gene there is one Sp1 binding site at bases −73 to −68 which has the sequence CCGCCC and the other is at bases −89 to −94 which has the sequence GGGCGG.

Sp1 and the sense approach and possibly duplex approach: The Sp1 binding can be interfered with using the single stranded oligonucleotide 5' GGGCGG 3' which is recognized by Sp1 and may thereby decrease Sp1 binding to these bases by the so called "sense" approach and by binding unwound DNA in duplex formation and also partly interfere with Sp1 binding in this way.

However, Sp1 is ubiquitous and may be interfered with in its other important functions. To minimize this the oligonucleotide may preferably be targeted to the parietal cell using one of the methods described in the conjugate section for delivery of agents or using liposomes which have appropriate cell recognition systems. Alternatively, it may be made longer as described below.

Preferably, to provide it with the appropriate stability in the stomach acid, and for oral administration, and targeting to the parietal cell, the antigene "sense" agent is made using at least two to four 2' O methyl oligoribonucleotides on either end or completely with 2' Omethyl oligoribonucleotides. This should also provide it with a possibility of a very long action. Under these conditions, and using low frequency of administration of say once about every four days to a week, it is likely to have less effect on most other cells which have a relatively short half life of 2 days compared to parietal cells which have a particularly long half life of 50-160 days.

Sp1 and a double stranded duplex approach: A 6 nm er antigene double stranded oligonucleotide GGGCGG: CCGCCC which is complementary to the above identified bases of the gene, should bind to Sp1 by the so called sense approach and may also bind when the proton pump gene becomes single stranded in this region when transcription occurs. The double stranded sequence may be made as a single strand where the two strands are joined with a dinucleotide or other dinucleotide abasic linker.

The Sp1 binding site on the gene is ubiquitous, and Sp1 binding may be interfered with in its other important functions. To minimize this the oligonucleotide may be targeted to the parietal cell using one of the methods described in the conjugate section for delivery of agents or using liposomes which have appropriate cell recognition systems.

Longer oligonucleotide to the Sp1 binding site for duplex action: The above identified duplex approach can also be made more specific than the sense approach by also targeting a few more nucleotides specific for the proton pump gene. Preferably a 12 nm er is made with bases chosen depending on how they assist in providing specificity for the target parietal cell proton pump alpha chain gene without compromising on self ligation or the formation of internucleotide bonds. The antigene sequence to target the Sp1 binding site furthest the initiation codon and the TATA box for RNA polymerase II, is GTC GGG CGG TTC (SEQ ID NO:71) or its complementary sequence GAACCGCCCGAC (SEQ ID NO:72). The latter is preferred because it does not form significant intermolecular or intramolecular binding. The antigene sequences to target the Sp1 binding site closest the initiation codon and the TATA box for RNA polymerase II is CAC CCG CCC TCC (SEQ ID NO:73) or GGA GGG CGG GTG (SEQ ID NO:74). Both of these are preferred as they do not form significant intermolecular or intramolecular binding.

Preferably, to provide it with the appropriate stability in the stomach acid, and for oral administration, and targeting to the parietal cell the antigene duplex agent is made using at least two to four 2' O methyl oligoribonucleotides on either end or completely with 2'O methyl oligoribonucleotides. These modifications can provide it with a very long action. Under these conditions, and using low frequency of administration of say once about every four days to a week, it is likely to have even less effect on most other cells which have a relatively short half life of 2 days compared to parietal cells which have a particularly long half life of 50-160 days The above identified oligonucleotides or parts of them can however, be given a further about 3-6 base recognition sequence on either one or both ends of the gene Sp1 binding site to make it more gene specific. The preferred modifications will not cause self ligation or internucleotide bonding. The size of the oligonucleotide should preferably not be too large to enable it to bind to the duplex as it opens up.

Sp1 target site and triplex binding: The Sp1 binding site at −73 to −68 on the gene which is closest to the TATA box at −59 to −53 may also be interfered with by triplex bonding to the pyrimidine: purine rich site at −83 to −63. The pyrimidines are in the sense DNA strand and the purines are predominantly in the antisense strand as follows 5' AGG GAG GGC* GGT*GGG GT*G GAG 3' (SEQ ID NO:75). The asterix * indicate where there is pyrimidine bases amongst the otherwise purine rich region, for which modifications in the choice of bases are needed for triplex binding. The underlined part shows some of bases to where Sp1 binding may occur. It is noted that this sequence also contains a CACCC box (i.e. GGGTG).

Triplex forming antigene oligonucleotide may bind to this region when it is double stranded or single stranded and may have an effect on interfering with Sp1 binding to this purine rich region.

A triplex forming compound may be made from either CT, or GT, or GA rich oligonucleotides that bind to the purine rich region and modifications where there are C, T's as is known in the art.

GA oligonucleotides: In one embodiment a GA triplex forming compound is made antiparallel compared to the purine rich sequence double stranded DNA. This may be made to include all or some of bases selected from the following 21 base sequence, GAG G A/C G GGG C/A GG G/T GGG AGG GA (SEQ ID NO:76) such as an 11mner GG G/T GGG AGG GA (SEQ ID NO:77). Neither the 21 nm er or 11 nm er appear to form significant Watson Crick intermolecular or intramolecular bonding, but there may be intramolecular bonding of other types. To decrease this the 11 nm er GA triplex forming oligo can be made to include about 3 or more bases TCC at the 3' end and about 6 bases CCA CCC at the 5' end for controlled fold back, in which case the oligo may be CCA CCC GGT GGT GGG AGG GA TCC (SEQ ID NO:78). For a preferred 21 nm er about 4 bases TCCC at the 3' end and about 4 bases CTCC at the 5' end can be added for controlled fold back. Acrydine may be also be added to the 5' end and/or cholesterol added to the 3' end of these oligos. Preferably phosphorothioates, and more preferably 2'Omethyl oligoribonucleotides are used on the ends or throughout as shown herein to be useful for acid reduction. Additionally or alternatively, spermine or related molecules may be used on the C's, and/or methylphosphonates, or 7 deaza bases may be used. The double asterix ** indicates where there is pyrimidine bases amongst the otherwise purine rich region oligo, for which modifications in the choice of base may be made as shown by the backslash /. The asterixed bases may be modified with A, C or G or T or an inosine or abasic linker or other base or chemical known in the art to be suitable for assisting triplex bonding to the corresponding T and C base in the otherwise rich purine antisense strand.

When this target Sp1 region is single stranded a double stranded triplex forming compound may be made comprising about 11 bases selected from the following bases GAG G A/C G GGG C/A CG G/T GGG AGG GA (SEQ ID NO:76). One such compound is an 11 mner GG GT GGG AGG GA (SEQ ID NO:77) and its complementary strand wherein the two strands are joined with a dinucleotide or other linker. The asterixed bases may be modified with A, C or G or T or an inosine or abasic linker or other base or chemical known in the art to be suitable for assisting triplex bonding to the corresponding T and C base in the otherwise rich purine antisense strand.

GT oligos: In a preferred embodiment a GT triplex forming compound is made either parallel or antiparallel compared to the purine rich sequence double stranded DNA is made. When antiparallel this may be made from all or some of bases selected from the following 22 base sequence, namely GTG GA/C G GGG A/C GG T/G GGG TGG GT (SEQ ID NO:79) such as an 11 mner GG T GGG TGG GT(SEQ ID NO:80). The parallel sequences are merely the above identified sequences in reverse but with a preference for the AAT bases respectively where asterixed. The 21 nm er or 11 nm er sequences do not form significant intermolecular or intramolecular. The 21 inner and 11 nm er GT triplex forming oligo can be made with acrydine attached to the 5' end and/or cholesterol added to the 3' end. Preferably phosphorothioates, and more preferably 2'Omethyl oligoribonucleotides are used on the ends or throughout as shown herein to be useful for acid reduction. Additionally or alternatively, spermine or related molecules may be used on the C's, if they are present in the sequence, and/or methylphosphonates, or 7 deaza bases may be used. The asterixed bases may be modified with A, C or G or T or an inosine or abasic linker or other base or chemical known in the art to be suitable for assisting triplex bonding to the corresponding T and C base in the otherwise rich purine antisense strand.

CT oligos: In another preferred embodiment a CT triplex forming compound is made preferably parallel compared to the purine rich sequence double stranded DNA. When parallel this may be made from all or some of bases selected from the following 21 base sequence, namely TCC CTC CCT/G CCC/A  CCC CC/A CCTC (SEQ ID NO:81) such as an 11mner TCC CTC CCT CC (SEQ ID NO:82). The 11 nm er CT triplex forming oligo can be made with acrydine attached to the 5' end and/or cholesterol added to the 3' end. Preferably the cytosines are methylated or spermine derivatives or similarly modified derivatives, and the phosphorothioates are Rp or Sp version, and more preferably 2'Omethyl oligoribonucleotides are used on the ends or throughout as shown herein to be useful for acid reduction. Alpha nucleotides CT may be used on the 3' end to increase stability as described previously. Additionally or alternatively, spermine or related molecules may be used on the C's, and/or methylphosphonates, or 7 deaza bases may be used. The asterixed bases may be modified with A, C or G or T or an inosine or abasic linker or other base or chemical known in the art to be suitable for assisting triplex bonding to the corresponding T and C base in the otherwise rich purine antisense strand.

It will be understood above that where RNA is used in the oligonucleotide the T is substituted for a U.

Tissue Specific Expression as the target site: To decrease the gene expression, including the induced expression, target sequence important in tissue specific expression in parietal cells may be targeted. The sense approach, or duplex or triplex antigene oligonucleotides approach can be used. Any of the methods described above for increasing the specificity of the agents to interfere with Sp1 binding may be implemented. For instance the oligonucleotide may be targeted to the parietal cell using one of the methods described in the conjugate section for delivery of agents or using liposomes which have appropriate cell recognition systems. Alternatively, using low frequency of administration of say once about every four days to a week, it is likely to have less effect on most other cells which have a relatively short half life of 2 days compared to parietal cells which have a particularly long half life of 50-160 days.

The oligonucleotide that works via duplex system or triplex may be made to target the [(G/C) Pu Pu(G/C)NGAT(A/T)PuPy] (SEQ ID NO:83) in the 5' upstream region of the beta and alpha genes in the human and rat which allow tissue specific expression (Maeda et al Yakugaku Azasshi 1996 February 116:2, 91-105).

TATA Box as the target site: The human TATA box TATATCA at bases −59 to −53 of the gastric proton pump alpha chain gene is a site for RNA pol II binding and transcription, and is an appropriate site for modulating the expression of the target gene. The 14 nm er sequence in the sense strand CTGGG TATATCA GG (SEQ ID NO:84) is conserved between the rat and human.

The sense approach, or duplex or triplex antigene oligonucleotides approach can be used. If a duplex approach is used the oligo sequence may be chosen from all or some of the bases above namely CTGGG TATATCA GG (SEQ ID NO:85) or the following complementary bases CCT GAT ATA CCC AG (SEQ ID NO:86). A duplex approach may also be used in which a double stranded oligo with a dinucleotide or other linker is used. Preferably the oligonucleotide is the 12 nm er or a smaller sequence chosen from the following sequence TGA TAT ACC CAG (SEQ ID NO:87) which does not produce significant intermolecular or intramolecular bonding. Preferably it is made using deoxynucleoside phosphorothioates and at least four 2'Omethyloligoribonucleotides phosphorothioates on either end as shown to work for acid reduction in Example 1, or completely with 2'Omethyloligoribonucleotides phosphorothioates.

Any of the methods described above for increasing the specificity of the agents to interfere with Sp1 binding may be implemented. For instance the oligonucleotide may preferably be targeted to the parietal cell using one of the methods described in the conjugate section for delivery of agents or using liposomes which have appropriate cell recognition systems. Alternatively, using low frequency of administration of say once about every four days to a week, it is likely to have less effect on most other cells which have a relatively short half life of 2 days compared to parietal cells which have a particularly long half life of 50-160 days.

Antigene-triplex bonding to purine rich regions in the DNA strand: An antigene triplex forming agent can also be designed to interfere specifically with any of the many other purine rich parts of the H+,K(+)-ATPase gene. A list of some of these regions is provided in Table 3 below.

Some of these purine rich regions are interrupted with some T's or C's to which appropriate triplex bonding is possible using the many modifications known in nucleotides or other means such as abasic linkers or inosine or chemicals substitutes to ensure triplex formation.

The antigenes may be made as CT, GT, or GA rich oligomers. Preferably when GT rich they are about 11 mner nucleotides, when CT rich they are about 15mners and when made GA rich they are made about 20 nm ers. That is not to say that smaller and larger versions of each will not work. To make the above antigene agents acid resistant and capable of oral administration, they may be made with deoxynucleoside phosphorothioates with at least four 2'-O-methyloligoribonucleotide phosphorothioates at both the 3' end and the 5' end as is shown herein in Example 1 to work in acid reduction. Importantly this also provides for a potentially long acting acid reducing drug which may be longer acting because triplex bonds may have long kinetics of action of perhaps a few days.

Of the above listed regions the preferred regions are those with at least about 11 nucleotides and with a similar proportion of G's and A's or C and T's or A's and T's, those purine rich regions that are not significantly interrupted with T or C, those purine rich regions which are specific to the human gene sequence, and perhaps about 16 nucleotides long, those conserved across species, and most preferably ones to which a protein factor that regulates transcription binds. Also the triplex forming oligonucleotide will preferably not have a run of four G's.

It is noted that the binding sites in the human gene for factors are well known and can be found inter alia in Maeda et al U Biol Chem Vol 265 p 9027-9032) and in the gene sequences provided by the databases referred to at page 5.

The antigene agents may be tested in vitro and/or in vivo in models described above. The in vitro culture may be of human parietal cells or another cell type transfected with the human proton pump gene, and one could look at decrease in message levels and/or protein, or change in the acidic contents of the culture. In vivo one may test for acid reduction as performed in Example 1 or in the ex vivo human fetal stomach model described above.

TABLE 3

The purine rich regions on the sense DNA strand suitable for antigene triplex formation include the following from the portion 5' of the initiation codon; the list begins with those furthest away from the initiation codon at about 2000 base pairs upstream. There may be more target regions further away.

AGG AAA AGG A (SEQ ID NO:88)

GGAAGAAGA (SEQ ID NO:89)

TAA AAA AAA AAA AAA (SEQ ID NO:90)

TABLE 3-continued

The purine rich regions on the sense DNA strand suitable for antigene triplex formation include the following from the portion 5' of the initiation codon; the list begins with those furthest away from the initiation codon at about 2000 base pairs upstream. There may be more target regions further away.

GGA TAA AGG GGA (SEQ ID NO:91)

AAA CAA ATA AAA AGA AAA (SEQ ID NO:92)

AAATAAA AAG AAA A (SEQ ID NO:93)

GGA GTA GGA GG (SEQ ID NO:94)

AAA GGA ACA GAA CACAG (SEQ ID NO:95)

GAA AGA GGT GAG AAA G (SEQ ID NO:96)

AAG GAA GGG GG (SEQ ID NO:97)

GAG TGG GAA GGG AAG G (SEQ ID NO:98)

GAG GGA TGA GGA GGG AG (SEQ ID NO:99)

GGG GAA TGG TTG AGA G (SEQ ID NO:100)

AAG AAG AGA ATA (SEQ ID NO:101)

GGG AGG CGG AGG (SEQ ID NO:102)

AAA AAA AAA AAG AAA AAA AAA AAG AG (SEQ ID NO:103)

AGG GGA GGG GGG GG (SEQ ID NO:104)

GGA GGG AAT G (SEQ ID NO:105)

The pyrimidine rich regions on the sense DNA strand, would have corresponding purine rich regions on the antisense strand for antigene triplex formation and include the following.

Corresponding Purine Rich Strand

TTT CCC CCT CT            AAG AGG GGG AAA
(SEQ ID NO:106)           (SEQ ID NO:109)

TTT GCT CTT CTT           AAG AAG AGC AAA
(SEQ ID NO:107)           (SEQ ID NO:110)

CTC CAC CCC ACC GCC       AGG GAG GGC GGT GGG
CTC CCT (SEQ ID NO:108)   GTG GAG (SEQ ID NO:111)

(the Sp1 binding site for which agents were made above)

Alternatively the purine rich regions may be partly on one strand and partly on the other such as the following, wherein the underlined pyrimidines are modified to purines.

TTTTTA GTA GAG ACA GGG (SEQ ID NO:112)

AAA GGG TCTTGTCCCCTC (SEQ ID NO:113) (the underlined part could have been included in the pyrimidine list above)

Also AT rich regions may be targeted as is known in the art, which sequences include the following.

TATTTTTTTTTTTTTTTTTTTT (SEQ ID NO:114).

AAAAATTTAAAAAATT (SEQ ID NO:115).

(ii) Antisense, Ribozyme, and Antigene Drugs Designed to Rat H+,K(+)-ATPase Alpha Chain The nucleotide sequences: An antisense, ribozyme, or antigene drug can be designed to the rat H+,K(+)-ATPase alpha or beta gene or messages using the sequences available inter alia in the scientific literature, the four major public databases described on page 5. Also SWISS-PROT has the alpha chain and the beta chain protein sequences. Various publications and databases that refer to the same protein, message and the gene sequences have been sourced to confirm conservation of target sequences. In the databases a ~200 base open reading frame sequence reported by Shull et al and (J. Biol Chem 261, 36 16788) in the rat 5' untranslated region of the cDNA sequences appears to be an artefact as it is not found in the genomic sequence (Ko-Ichi Oshiman et al Febs Vol 281, #1, 2, 250-254). However, in the latter the first intron site may begin and finish two bases earlier than shown to line up with the coding sequence. Comparing these two cDNA and gene sequences also suggests there may only be about a 25 base 5'Untranslated region.

Antisense sequences to the target rat mRNA alpha chain proton pump generated using one group of settings and to the initiation codon: The secondary structure of the whole human alpha chain proton pump mRNA was determined according to RNA draw sofware program based on Zuker secondary structure analysis developed by Ole Matzura (Dept Medical Biophysics Karolinska Inst S-171 77 Solna Sweden) as an example only. The default settings used were as for the human alpha chain molecule and a number of (hairpin, internal and bulge types) as identified below are used herein as a suitable reference point for distinguishing the different target sites for antisense drugs and for comparing to the human.

Using information generated from the secondary structure determinations of the rat mRNA using the one group of default settings, a list of candidate antisense drugs was made that satisfied antisense design criteria such as no or low intermolecular and intramolecular bonding.

Other drugs were also chosen based on knowhow that the initiation site is a good target site as determined from the present experiments in Example 1.

The list of designed antisense drug sequences is provided in Table 4 below.

It will be understood however that this is not a comprehensive list of drugs likely to work, because intermolecular and intramolecular bonding can be minimized by for example putting self stabilizing loops, and or by circularizing antisense. Also other drug sequences can be chosen based on other different default settings and/or using probabilities that a particular site is free as determined using the mfold server or knowhow.

It will also be understood by those skilled in the art from practical experience, that not all antisense drugs designed will work despite designing to optimize the probability of working. There is about a 12-80% chance of working and perhaps less depending on the skill of the designer, and of the ones that work about a third may work more optimally and a third will work at an intermediate level.

Agents that are directed to the initiation site, loop 201, and to the 3'untranslated region may be trialed first or another order of trialing can be chosen, based on the antisense not forming any intermolecular or intramolecular bonding, or that the targeted sequences are conserved across species such as in the dog or rat.

It will be understood that T and U are interchangeable depending on whether DNA or RNA is used e.g. deoxynucleotide phosphorothioate (T) or oligoribonucleotide phosphorothioate (U) respectively.

TABLE 4

ANTISENSE DRUGS RATIONALLY DESIGNED TO THE RAT PROTON PUMP ALPHA CHAIN MESSAGE

| Loop number(s) | Nucleolides | Antisense size | Comments |
| --- | --- | --- | --- |
| (a) 17, 18, 19, and 20<br>AAT TCA TAA TTC TCC TTC CCC AT<br>(SEQ ID NO:116) | 1-23 | 23 mner* | To initiation site*<br>The ATG site at base<br>207-209 |
| AAT TCA TAA TTC TCC TTC CCC<br>(SEQ ID NO:23) | | 21 mner | +/- alpha anomer end |
| AAT TCA TAA TTC TCC TTC<br>(SEQ ID NO:24) | | 18 mner | +/- alpha anomer end |
| AAT TCA TAA TTC TCC<br>(SEQ ID NO:25) | | 15 mner | +/- alpha anomer end |
| (b) 201<br>GUG AUA TAG ATA AGG TAG GG UGU<br>(SEQ ID NO:117) | 2595-2617 | 23 mner* | **loop 201 is equivalent to human loop 195 but is not as optimal in the rat |
| 201<br>GUG ATA TAG ATA AGG TAG GG<br>(SEQ ID NO:118) | 2392-2411 (2598-2617) | 20 mner | The underlined bases are G's in the human antisense drug<br># brackets begin from 5'UT |
| (c) 145<br>tag tcc ttc tca ttc agg tag a<br>(SEQ ID NO:56) | 1699- | 22 mner | directed to the coding region |
| (d) 196 + 197<br>tga aaa tag gaa taa gca<br>(SEQ ID NO:119) | 2577- | 21 mner | directed to the coding region |
| (e) 34<br>cat ctc ctt ctc cat gtt ctc<br>(SEQ ID NO:55) | 123 | 21 mner | directed to the coding region |

TABLE 4-continued

ANTISENSE DRUGS RATIONALLY DESIGNED TO THE RAT
PROTON PUMP ALPHA CHAIN MESSAGE

| Loop number(s) | Nucleolides | Antisense size | Comments |
|---|---|---|---|
| (f)   245 + 246<br>agc aga aca tga gga att<br>(SEQ ID NO:120) | 3568- | 19 mner | directed to 3' untranslated region<br>(the last base is 3615) |

*one of the antisense drugs ARISA 1 that works in Example 1 was an antisense drug designed to the Rat gastric proton pump initiation site. Although not wishing to be restricted to any particular mechanism, this drug may work by one or more of the following means, including blocking ribosome attachment, blocking translation initiation, Rnase H degradation of the message, interfering with ribosome translocation, or interfering with processing of the pre-mRNA because it overlaps the exon-intron boundary, or any other means
**one of the antisense ARAL 201 that works in Example 1 was an antisense drug designed to the rat gastric proton pump loop 201. Although not wishing to be restricted to any particular mechanism this drug may work via Enase H degradation of the message or interfering with ribosome translocation or by any other means.

Some of the best antisense drugs are designed around the initiation site to interfere with ribosome attachment and/or translation initiation. These do not need to incorporate the ATG initiation methionine codon and may be just downstream or upstream of this site. If there are any non specificity problems associated with Rnase H activity then 2' O methyl bases may be used throughout or for all but 1-3 bases over the problem region. Preferably the antisense drugs to this site also have some of the first 10-12 bases of coding region to reach the first intron boundary splice site and thus provide the possibility of affecting processing of the pre-mRNA.

Moreover some of the following other drugs may be made to the 5'Untranslated region and the initiation site: A 24 nm er to bases 1-24; A 21 nm er to nucleotides 5-26;

A 26 nm er antisense to the 5' untranslated region up to –25 relative to the initiation codon.

The drug to the 5' UT region and to the cap site should interefere with ribosome attachment and processing. Antisense drugs to the initiation and 5'UT and cap region may work even though they are not optimal with regard to low intermolecular and intramolecular binding.

One preferred type of antisense drug has four 2'O methyl ribonucleoside phosphorothioates on either end and the inner bases are deoxynucleoside phosphorothioates, so that it supports Rnase H degradation of the message.

The above identified antisense drug sequences and chemistrie should provide favourable pharmacokinetics, general stability to nucleases, stability via the oral route of administration, efficacy in some cases, and potentially long action as shown in Example 1 for the rat drug.

A small antisense sequence e.g. 15 nm er works well when directed to the initiation sites or perhaps a 5' or 3' untranslated region. Smaller and longer versions of these drugs will also work; preferably longer versions do not impact significantly on intermolecular and/or intramolecular binding. Antisense drugs bigger than about 17-20 nm ers may also be long enough to provide another mechanism of action, namely blocking ribosome translocation in the coding region and thus mRNA translation.

When using smaller versions of long antisense drugs or small antisense drugs, if necessary, one may do a number of things including one or more of the following to increase affinity to the target site:

(i) change the deoxynucleoside phosphorothioates to more 2' O methyls
(but keeping at least about 4-5 if necessary or preferred to keep Rnase H activity), (ii) use all 2' O methyl if the drug does not need to work via Rnase H (iii) using high affinity C and/or T propynyl bases such as C-5 propyne or methylcytosine the natural nucleobases; or (iv) make a longer drug incorporating (most of) this sequence and a few other nucleotides e.g. 6; preferably the latter added nucleotides do not impact significantly on intermolecular and/or intramolecular binding.

Part or all of the antisense drug may be used as one half of two overlapping 9 nm ers. This may be appropriate for some of the smaller antisense drugs e.g. the 13 nm er-16 nm ers ARAL 201 can be made into a 24 nm er by also targeting base 2594 with only a little impact on intermolecular binding.

A region immediately preceding this targeted region may also be an appropriate site although the intermolecular and intramolecular structures formed in antisense that targets this region appears not to be as optimal as that of the 23 nm er above.

TABLE 5

Some Rat equivalents to the earlier identified antisense sequences to the human proton pump alpha chain in table 1. The underlined bases show the few differences in the human and rat antisense sequence.

| Loop number(s) | Nucleotides | Antisense size | Comments (see table 4) |
|---|---|---|---|
| (a)<br>TCT TCT CGT<br>TTT CCA CAC CC<br>(SEQ ID NO:121) | 852<br>(1058-1077) | 20 mner | to human loop<br>91 |

The sequence GAG can be added to the 5' end of the antisense to make it a 23 nm er (targets 1078-80). These antisense sequences do not have any significant intermolecular or intramolecular binding as also occurs with the human equivalent. Although, the binding site on the rat message may not be as good as the binding in the corresponding human mRNA sequence, it is still considered a good site to target.

(b) A rat sequence equivalent to the human one directed to human loops 204 and 203 is the 19 nm er CAG GGA CAC AGA TGG AAA G (SEQ ID NO:122) which is directed to the rat sequence beginning at coding base 2475 (2681-2699). This sequence does not have any significant intermolecular or intramolecular binding as also occurs with the human equivalent. The binding site on the rat message may not be as good as the binding site in the corresponding human mRNA sequence throughout. To increase the melting temperature bases on either end may be targeted such as the 2 bases at 2679/80 and/or the 3 bases 2700-2. This does not significantly affect the intermolecular structures that can form, and no intramolecular structures form. TGC CAG GGA CAC AGA TGG AAA GAT (SEQ ID NO:123).

(c) A rat antisense sequence equivalent to the human one directed to human loop 184 is the 18 nm er CAT TTT TAG CAG CAT CGG (SEQ ID NO:124).

(d) A rat antisense sequence equivalent to the human one directed to human loop 189 is the 16 nm er CGA AGT TGT CAT CCA G (SEQ ID NO:125).

(e) A rat antisense sequence equivalent to the human one directed to human loop 227 is the 16 nm er CTA AUA GUA GAG UUC C (SEQ ID NO:126). This is the same as the human equivalent.

There are also other antisense equivalent to the human antisense sequences in table 1 that are worthwhile trying as can be determined using the rational design criteria described herein and known in the art.

Other Rat Antisense Drugs Corresponding to Rat Antisense Drugs Generated Using the Many Alternative Settings The secondary structure of the rat proton pump alpha chain was determined by submitting the first 3000 bases of the rat sequence to the mfold server. The ATG initiation codon is at base 207-209. The human gastric proton pump sequence is longer than 3000 bases, and starts at nucleotides −30 i.e. equivalent to base 177 in the rat.

The likelihood of secondary structure at any particular base in the rat gastric proton pump alpha chain was used as a basis to make a list of target regions in the rat message. Antisense can be made to some of these regions, with the preferred ones having low intermolecular and low intramolecular binding.

Some of the regions considered as appropriate sites for further analysis and for targeting are as follows:

(i) in the putative 5'UT region; the cap site, at 46-64, and at 101-122.

(ii) In the coding region (wherein base 207 is the initiation codon); bases 354-376, 402-425, 451-474, 618-639, 681-705, 715-737, 755-777, 967-997, 1021-1042, 1089-1109, 1161-1178, 1292-1314, 1346-13631375-1393, 1453-1474, 1531-1551, 1600(5)-1622, 1708-1730, 2010-2035, 2105-2126, 2172-2192, 2198-2227, 2373-2397, 2406-2422, 2836-2860, 2926-2948. Bases downstream of 3000 were not done using this program.

Other regions including bases 204-232*, 329-349, 1058-1083, 1904-1928, 2576-2618*, 2679-2702, 2783-2804 were previously identified as appropriate regions to target antisense, and antisense to these have been made and referred to in tables 4 and 5. The asterix shows two preferred regions, namely bases around the initiation codon and loop 201.

The availability of this more detailed secondary structure information for each base can also be used to improve the antisense drugs and size of some of the antisense drugs referred to above in Tables 4 and 5.

It should be noted also that suitable human antisense drugs could be made equivalent to any rat antisense drugs directed to these sites; optimized for no or low intramolecular and intermolecular binding according to the human specific sequence or via removing unwanted intermolecular and intramolecular bonding via other means such as by self stabilization and/or circularization.

Rational Design of Morpholino Phoshorodiamidates to Rat Gastric Proton Pump Alpha Chain mRNA As described for the human gastric proton pump alpha chain mRNA, morpholino phoshorodiamidates are known in the art to act best by blocking ribosome attachment, interfering with the cap site processing, interfering with translation initiation of the targeted mRNA and/or to work at exon-intron boundaries. When rationally designing, the secondary structure of the mRNA target site may be less important using antisense drugs made from these nucleotides although it may be preferable to have a small single stranded region for nucleation pairing by the antisense. The intramolecular and intermolecular bonds of the antisense drug itself is however usually important for best effect. Preferably the antisense should form no more than 4 contiguous intrastrand base pairs although 4 contiguous base-pairs may be undesirable if all four are G:C pairs. The antisense drug may be a 23 nm er or a 25 nm er. Preferably the uracils are switched to thymines. Preferably the oligonucleotide does not contain over about 36% guanines or more than 3 contiguous guanines.

Regions from the 59 Cap to about 25 bases 3' to the AUG translation start site of the rat gastric proton pump are likely to work when targeted with morpholino antisense with some antisense working well.

Morpholino versions of ARISA 1 the antisense drug identified to work well in the Example 1 directed to the rat initiation codon also incorporating the first exon-intron region are expected to work particularly well.

Morpholino phosphorodiamidate drugs that can be made to the initiation site include those corresponding to the 23 nm er* ARISA 1 as defined in Example 1 namely AAU UCA TAA TTC TCC TTC CCC AU (SEQ ID NO:5) wherein the underlined bases are 2' O Methyl modified phosphorothiates. Preferably with a morpholino phosphorodiamidate the Uracyls are replaced with Thymines as in the following sequence AAT TCA TAA TTC TCC TTC CCC AT (SEQ ID NO:116).

Moreover some of the following other morpholino drugs that may be made to this site include a 24 nm er made to bases 1-24 which requires a further C at the 5' Oligo end of the 23 nm er above. A 24 nm er still has favourable intramolecular and intermolecular bonding. Also a longer 25 nm er which includes a further AC at the 5'Oligo end of the 23 nm er and is directed to bases 1-25, also has favourable intramolecular and intermolecular bonding as is preferred.

A morpholino including any part or all of a 21 nm er TAC AAT TCA TAA TTC TCC TTC (SEQ ID NO:127) made directed to nucleotides 5-26 of the coding region, may work well because there may be sufficient single stranded region to allow nucleation. Preferably such an antisense drug is a 23-25 nm er with no or small intramolecular binding as required for morpholinos and low intramolecular binding. This requires that a CC, CCC, or CCCA is put on the 3' end of the 21 nm er.

The ATG site is at base 207-209. Thus there is significant 5'-untranslated region. A 23-25 nm er morpholino antisense selected from the following 27 nm er sequence GGT GGC TAG GTG CTC TGC CCT CTT TGA (SEQ ID NO:128) to the 5' untranslated region up to −27 relative to the initiation codon may work. This corresponds to base 180-206. Antisense drugs to the 5'UT region may work even though they are not optimal with regard to low intermolecular and intramolecular binding. Better ones may be 25 nm ers T GGC TAG GTG CTC TGC CCT CTT TGA (SEQ ID NO:129). Other regions from 149-172 can be targeted with a 24 nm er TTA CTG TGT GAA GCA GGC CAT GAA (SEQ ID NO:130) which may work based on sufficiently low intramolecular bonding and accessibility to the site. Also the 25 nucleotide region 98-122 may be targeted with TCT GCA CCC CTC GTC TCA TGT ACA T (SEQ ID NO:131) which has no intramolecular bonding but significant intermolecular bonding. The 23 nucleotide region 38-60, may be worthwhile targeting with a 23 nm er GTC GTG TGC ATG TAT CGA TTT CT (SEQ ID NO:132) which has no intramolecular bonding, although there is major intermolecular bonding, and the region 1-24 to the putative cap site may also be targeted with TGT ATG TAC CCC TTT ATT GCT CAG (SEQ ID NO:133) which has no intramolecular or intermolecular bonding.

The preferred antisense oligonucleotide may be smaller than that described as optimal at the Gene—Tools web site. Preferably the antisense oligonucleotide is also modified at either one or both of the 5' or 3' ends to improve the potential for long action.

Targeting Exon_Intron Regions

Forty two other morpholino antisense drugs can also be made to overlap the exon intron boundaries of the pre-mRNA. There are 22 known exons, with the sixth exon not been separated by an intron, and thus 41 exon-intron boundaries on the pre-mRNA of the rat gastric proton pump alpha chain gene and another two boundaries between exons and 5' and 3' gene regions.

Possible advantages are described above in the human sequence. These include improved specificity and nuclease resistance. Since the morpholino phosphorodiamidate does not work via an RNase H mechanism of action it is expected to cause fewer non specific effects in interfering with the proton pump. It should also have a better safety profile. Other advantages include that the morpholino agents may work at lower doses and they may not be easily degraded once inside the cell. Thus the particularly long half life of the parietal cell may allow for a particularly long action, of a week, fortnight, or month, or even a few months using morpholino phosphorodiamidate.

Antigene Drugs to the Rat Alpha Chain Gene

Antigene oligonucleotide drugs can be made to work via the duplex or triplex method or by the sense approach as outlined for the human gene.

TATA Box as the target site: The TATA box TATATCA of the rat gastric proton pump alpha chain gene is a site for RNA pol II binding and transcription, and is an appropriate site for modulating the expression of the target gene. The 14 nm er sequence in the sense strand CTGGG TATATCA GG (SEQ ID NO:84) is conserved between the rat and human (Ko-Ichi Oshiman et al Febs Vol 281, #1,2,250-254).

The sense approach, or duplex or triplex antigene oligonucleotides approach can be used.

If a duplex approach is used the oligo sequence may be chosen from all or some of the bases above namely CTGGG TATATCA GG (SEQ ID NO:85) or the following complementary bases CCT GAT ATA CCC AG (SEQ ID NO:86). A duplex approach may also be used in which a double stranded oligo with a dinucleotide or other linker is used. Preferably the oligonucleotide is the 12 nm er or a smaller sequence chosen from the following sequence TGA TAT ACC CAG (SEQ ID NO:87) which does not produce significant intermolecular or intramolecular bonding. Most preferably it is made using deoxynucleoside phosphorothioates with at least four 2'O methyl oligoribonucleotides phosphorothioates on both ends as shown for acid reduction in Example 1, and/or completely using 2'O methyl oligoribo phosphorothioates.

Any of the methods described above for increasing the specificity of the agents to interfere with Sp1 binding in the human may be implemented. For instance the oligonucleotide may preferably be targeted to the parietal cell using one of the methods described in the conjugate section for delivery of agents or using liposomes which have appropriate cell recognition systems. Alternatively, using low frequency of administration of say once about every four days to a week, it is likely to have less effect on most other cells which have a relatively short half life of 2 days compared to parietal cells which have a particularly long half life of 50-160 days.

The Sp1 site and Tissue Specific Expression as the target site: As described for the human drugs. One triplex forming oligo to both Sp1 sites in the rat is a 14 mner GGG AGT GGG AGG AG (SEQ ID NO:134). Antigene-triplex bonding to purine rich regions in the DNA strand.

An antigen triplex forming agent can also be designed to interfere specifically with any of the many other purine rich parts of the $H^+,K(+)$-ATPase gene (Ko-Ichi Oshiman et al Febs Vol 281, #1,2,250-254). These purine rich regions may be interrupted with some T's or C's to which appropriate triplex bonding is possible using the many modifications known in nucleotides or other means such as abasic linkers or inosine or chemicals substitutes to ensure triplex formation.

The antigenes may be made as CT, GT, or GA rich oligomers as described above for those targeting the human Sp1 binding site. Preferably when GT rich they are about 11mner nucleotides, when CT rich they are about 15 nm ers and when made GA rich they are made about 20 mners. That is not to say that smaller and larger versions of each will not work. To make the above antigene agents acid resistant and capable of oral administration, they may be made with deoxynucleoside phosphorothioates with at least four 2'-O-methyloligoribonucleotide phosphorothioates at both the 3' end and the 5' end as is shown herein in Example 1 to work in acid reduction. Importantly this also provides for a potentially long acting acid reducing drug which may be longer acting because triplex bonds may have long kinetics of action of perhaps a few days.

Of the purine rich regions the preferred regions are those with at least about 11 nucleotides and with a similar proportion of G's and A's or C and T's or A's and T's, those purine rich regions that are not significantly interrupted with T or C, those purine rich regions which are specific to the rat gene sequence, and perhaps about 16 nucleotides long, those conserved across species, and preferably ones to which a protein factor that regulates transcription binds e.g. −555 to −581 CACCC boxes.

(iii) Antisense, Ribozymes, Antigene Agents to Rat Histamine H2-Receptor

Antisense Drugs

Rat Histamine H2 receptor sequence: The rat histamine H2 receptor message sequences are found in the scientific literature and made available inter alia in Gen Bank. The protein sequences can be found at SWISS-PROT P25102 for the rat.

The rat histamine H-2 receptor gene sequences with the TATA box and sequences more 5' can be located interalia in Ruat et al Biochem Biophys Res Comm. 1991, 179:3 p1470-1478, and Nishi et al Biochem Biophys Res Commun 1995 May 16, 210:2, 616-23.

The mRNA target sites with potential for low secondary structure: The secondary structure of the whole rat alpha histamine H2 receptor mRNA molecule was determined according to RNA draw software program based on Zuker secondary structure analysis developed by Ole Matzura (Dept Medical Biophysics Karolinska Inst S-171 77 Solna Sweden).

The default settings were used and suitable sites were identified that had a good probability of low secondary structure. It will be understood by those skilled in the art that changing the default settings alters the secondary structure determinations as can be determined by submitting the base sequence to the mfold server.

Briefly sites were chosen where there was no or low secondary structure as described earlier for the proton pump studies to allow access to antisense drugs. Knowhow also suggests that there will be access to parts near the initiation codon sufficient for designing morpholino phoshorodiamidates. These drugs will also work at exon-intron boundaries. When rationally designing, the secondary structure of the mRNA target site may be less important using antisense drugs made from these nucleotides although it may be preferable to have a small single stranded region for nucleation pairing by the antisense.

Rat antisense drugs chosen for low intermolecular and intramolecular binding: Rat antisense drugs were designed based on having no or low intermolecular and intramolecular binding to the above identified sites. The following 5 antisense drugs listed in Table 6 are considered good candidates to test for antisense activity.

Other design principals were as described above for the gastric proton pump and as is known in the art. For instance the antisense are preferably made from deoxynucleoside phosphorothioates comprising four 2'-O-methyloligoribonucleotide phosphorothioates at each of the 3' end and the 5' end or any other appropriate modification some of which are referred to in the tables above.

TABLE 6

| | |
|---|---|
| TGT GCC ATT GGG CTC CAT (SEQ ID NO:135) | 18mner to the initiation codon There is less importance on secondary structure |
| TGA GGA AAA AAA GTG GAG GG (SEQ ID NO:136) | 20mner antisense to loop 2 in the 5' untranslated region (the first seven bases bind to a stem region on mRNA) |
| TAA AGG CAA GTT GGG GAA G (SEQ ID NO:137) | 19mner antisense to loop 45 in the 5' untranslated region (the rat mRNA also has no secondary structure) |
| GTG ATG AGG ATG AGC CGT GGT AAC C (SEQ ID NO:138) | 25mner to antisense to loop 62 and 61 of coding (bases 5-12 bind to a stem region on mRNA) |
| AAT GGC AGA GAA GGG CAG (SEQ ID NO:139) | 18mner antisense to loop 69 of coding region (the rat mRNA has no secondary structure-excellent) (same antisense sequence as the human) |
| CTA GGA ATG GTC TTA GCA (SEQ ID NO:140) | 18mner antisense to loop 118 of 3' untranslated region. |

Antisense, Ribozymes, Antigene Agents to Human Histamine H2 R.

Human Histamine H2 Receptor Sequence

The human histamine H2 receptor message sequences are found in the scientific literature and made available inter alia in Gen Bank. The protein sequences can be found at SWISS-PROT: P25021 for human.

The rat histamine H-2 receptor gene sequences with the TATA box and sequences more 5' can be located interalia in Nishi et al Biochem Biophys Res Commun 1995 May 16, 210:2, 616-23.

Antisense to the Human Histamine H2 Receptor mRNA Sequence

One preferred antisense sequence to the human Histamine H2 receptor message was made to a region which is completely conserved between rat and human.

The 18 nm er AAT GGC AGA GAA GGG CAG (SEQ ID NO:141) is the antisense to the human sequence equivalent to the antisense to the rat loop 69 of coding region (the rat mRNA has no secondary structure-excellent). This targets nucleotide 274 in the human coding region.

Since this sequence is completely conserved between rat and human the likelihood is that the sequence is conserved in different members of the human community.

Another antisense to the human sequence can be made to the initiation site of the human histamine H2 receptor message. Such an antisense may be the 18mner TGT GCC ATT GGG TGC CAT (SEQ ID NO:142). This has high similarity to the corresponding rat sequence and may work via a similar mechanism of interfering with ribosome attachment and translation initiation.

Other design principals are as described above for the gastric proton pump and as is known in the art. For instance the antisense are preferably made from deoxynucleoside phosphorothioates comprising four 2'-O-methyloligoribonucleotide phosphorothioates at each of the 3' end and the 5' end or any other appropriate modification some of which are referred to in the tables above.

Knowhow also suggests that there will be access to parts near the initiation codon sufficient for designing morpholino phoshorodiamidates. These drugs will also work at exon-intron boundaries. When rationally designing, the secondary structure of the mRNA target site may be less important using antisense drugs made from these nucleotides although it may be preferable to have a small single stranded region for nucleation pairing by the antisense.

Ribozyme to the Rat or Human

The statements made above in relation to design of ribozymes for the proton pump are relevant with regard to design of ribozymes to the histamine H2 receptors of the rat or human.

Antigene to the Rat or Human

The statements made above in relation to design of antigene duplexes and triplexes for the proton pump are relevant with regard to design of antigene to the histamine H2 receptors.

Nishi et al supra compares the rat and human sequences in the promoter region. An antigene oligonucleotide duplex or triplex agent may be rationally designed and used to interfere with transcription from the rat TATA sites or other sites referred to in Ruat paper such as those at around −360 to −373 or −505 to −520 which are purine or purine-pyrimidine rich. In the human gene Nishi describes upstream regions −610 and −278 that contain AP2 sites and GATA motifs some of which are also rich with purines and thus particularly good sites for triplex formation. A further upstream region −1202 to −611 bp also has positive regulator regions and thus suitable targets sites.

An antigene duplex or triplex forming agent can be designed to interfere specifically with any part of the histamine H2 receptor gene as described for the gastric proton pump gene. It is also noted the parietal cell expresses both the histamine H2 receptor and the proton pump, and thus the design principals relying on the chemistry of the agents and frequency of dosing should be much the same.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A method for decreasing production or secretion of gastric acid in a human subject in need thereof, which method comprises administering to the subject an effective amount of an oligonucleotide capable of reducing or inhibiting gastric acid production or secretion in the subject, wherein said oligonucleotide consists of from 12 to 30 nucleobases and is entirely complementary to a region of an RNA transcript encoding an alpha chain of the human gastric proton pump.

2. A method as claimed in claim 1 wherein the region is selected from the group consisting of:
   (a) a region involved in translation initiation;
   (b) a region involved in ribosome attachment to the transcript;
   (c) a 5' untranslated region;
   (d) a region encompassing an exon-intron boundary;
   (e) a coding region; and
   (f) a 3' untranslated region.

3. A method as claimed in claim 1 wherein the oligonucleotide comprises at least a seven nucleotide portion of
   (T/U) CA(T/U) AG(T/U) (T/U)C(T/U) CGG CC (T/U)(T/U)C CCC A(T/U) (SEQ ID NO:3).

4. A method as claimed in claim 1 wherein the oligonucleotide has a sequence selected from the group consisting of:
   AAU UCA TAA TTC TCC TTC CCC AU (SEQ ID NO:5);
   GUG ATA TAG ATA AGG TAG GG UGU (SEQ ID NO:6);
   U CAU AGT TCT CGG CC TTC CCC AU (SEQ ID NO:7);
   U CAU AGT TCT CGG CC UUC CCC AU (SEQ ID NO:8);
   U CAU AGU UCU CGG CC UUC CCC AU (SEQ ID NO:9);
   CAU AGU TCT CGG CCT TCC CCA U (SEQ ID NO:10);
   CAU AGT TCT CGG CCU UCC CCA U (SEQ ID NO:11);
   CAT AGT TCT CGG CCT TCC CCA T (SEQ ID NO:12);
   CAT AGT TCT CGG CCT TCC CCA TG (SEQ ID NO:13);
   CAT AGT TCT CGG CCT TCC CCA TGG (SEQ ID NO:14);
   CAT AGT TCT CGG CCT TCC CCA TGGT (SEQ ID NO:15);
   GUG AUG TAG ATG AGG UAG GG (SEQ ID NO:16);
   CA(T/U) AG(T/U) (T/U)C(T/U) C GGC C(T/U)(T/U) CCC CA(T/U) (SEQ ID NO:17);
   CA(T/U) AG(T/U) (T/U)C(T/U) C GGC C(T/U)(T/U) CCC C (SEQ ID NO:18);
   CA(T/U) AG(T/U) (T/U)C(T/U) C GGC C(T/U)(T/U) CC (SEQ ID NO:19);
   CA(T/U) AG(T/U) (T/U)C(T/U) C GGC C(T/U) (SEQ ID NO:20); and
   CA(T/U) AG(T/U) (T/U)C(T/U) C GGC C (SEQ ID NO:21).

5. A method as claimed in claim 1 wherein the oligonucleotide comprises at least one modified internucleoside linkage.

6. A method as claimed in claim 1 wherein the oligonucleotide comprises at least one modified sugar moiety.

7. A method as claimed in claim 6 wherein the modified sugar moiety is selected from the group consisting of a 2'-O-propyl sugar moiety, a 2'-O-alkyl sugar moiety, a 2'-O-aminopropyl sugar moiety, a 2'-O-methyl sugar moiety, a 2'-O-methoxyethyl sugar moiety or a 2'-allyl sugar moiety.

8. A method as claimed in claim 1 wherein the oligonucleotide comprises at least one modified nucleobase.

9. A method as claimed in claim 1 wherein the oligonucleotide is conjugated to a delivery agent.

10. A method as claimed in claim 9 wherein the delivery agent is selected from the group consisting of $K^+$ ions, gastric proton pump inhibitors and agents which bind to parietal cell surface receptors.

11. A method as claimed in claim 1 wherein the oligonucleotide is administered orally.

12. A method as claimed in claim 11 in which the effective amount is administered at a dosing frequency of once every 4 to 7 days.

13. A method as claimed in claim 1 wherein the oligonucleotide is administered in conjunction with a gastric acid neutralizing agent or an agent which interferes with the production or secretion of gastric acid.

* * * * *

SEQUENCE LISTING

<160> NUMBER OF SEQ ID NOS: 143

<210> SEQ ID NO 1
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic antisense oligonucleotide, can be
      RNA, DNA or chimera
<220> FEATURE:
<223> OTHER INFORMATION: Description of Artificial Sequence: Synthetic
      antisense oligonucleotide, can be RNA, DNA
      or chimera
<220> FEATURE:
<221> NAME/KEY: modified_base
<222> LOCATION: (3)..(4)
<223> OTHER INFORMATION: T or U
<220> FEATURE:
<221> NAME/KEY: modified_base
<222> LOCATION: (7)
<223> OTHER INFORMATION: T or U
<220> FEATURE:
<221> NAME/KEY: modified_base
<222> LOCATION: (10)..(11)
<223> OTHER INFORMATION: T or U
<220> FEATURE:
<221> NAME/KEY: modified_base
<222> LOCATION: (13)
<223> OTHER INFORMATION: T or U
<220> FEATURE:
<221> NAME/KEY: modified_base
<222> LOCATION: (16)..(17)
<223> OTHER INFORMATION: T or U
<220> FEATURE:
<221> NAME/KEY: modified_base
<222> LOCATION: (23)
<223> OTHER INFORMATION: T or U

<400> SEQUENCE: 1
aanncanaan ncnccnnccc can                                             23

<210> SEQ ID NO 2
<211> LENGTH: 24
<212> TYPE: DNA
<213> ORGANISM: Artificial Sequence
<220> FEATURE:
<223> OTHER INFORMATION: Description of Combined DNA/RNA Molecule:
      Synthetic antisense oligonucleotide, can be
      RNA, DNA or chimera
<220> FEATURE:
<223> OTHER INFORMATION: Description of Artificial Sequence: Synthetic
      antisense oligonucleotide, can be RNA, DNA
      or chimera
<220> FEATURE:
<221> NAME/KEY: modified_base
<222> LOCATION: (3)
<223> OTHER INFORMATION: T or U
<220> FEATURE:
<221> NAME/KEY: modified_base
<222> LOCATION: (6)
<223> OTHER INFORMATION: T or U
<220> FEATURE:
<221> NAME/KEY: modified_base
<222> LOCATION: (8)
<223> OTHER INFORMATION: T or U
<220> FEATURE:
<221> NAME/KEY: modified_base
<222> LOCATION: (12)
<223> OTHER INFORMATION: T or U
<220> FEATURE:
<221> NAME/KEY: modified_base
<222> LOCATION: (17)
<223> OTHER INFORMATION: T or U

```
<220> FEATURE:
<221> NAME/KEY: modified_base
<222> LOCATION: (22)
<223> OTHER INFORMATION: T or U
<220> FEATURE:
<221> NAME/KEY: modified_base
<222> LOCATION: (24)
<223> OTHER INFORMATION: T or U

<400> SEQUENCE: 2
agngananag anaaggnagg gngn                                              24

<210> SEQ ID NO 3
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic antisense oligonucleotide, can be
      RNA, DNA or chimera
<220> FEATURE:
<223> OTHER INFORMATION: Description of Artificial Sequence: Synthetic
      antisense oligonucleotide, can be RNA, DNA
      or chimera
<220> FEATURE:
<221> NAME/KEY: modified_base
<222> LOCATION: (1)
<223> OTHER INFORMATION: T or U
<220> FEATURE:
<221> NAME/KEY: modified_base
<222> LOCATION: (4)
<223> OTHER INFORMATION: T or U
<220> FEATURE:
<221> NAME/KEY: modified_base
<222> LOCATION: (7)..(8)
<223> OTHER INFORMATION: T or U
<220> FEATURE:
<221> NAME/KEY: modified_base
<222> LOCATION: (10)
<223> OTHER INFORMATION: T or U
<220> FEATURE:
<221> NAME/KEY: modified_base
<222> LOCATION: (16)..(17)
<223> OTHER INFORMATION: T or U
<220> FEATURE:
<221> NAME/KEY: modified_base
<222> LOCATION: (23)
<223> OTHER INFORMATION: T or U

<400> SEQUENCE: 3
ncanagnncn cggccnnccc can                                               23

<210> SEQ ID NO 4
<211> LENGTH: 24
<212> TYPE: DNA
<213> ORGANISM: Artificial Sequence
<220> FEATURE:
<223> OTHER INFORMATION: Description of Combined DNA/RNA Molecule:
      Synthetic antisense oligonucleotide, can be
      RNA, DNA or chimera
<220> FEATURE:
<223> OTHER INFORMATION: Description of Artificial Sequence: Synthetic
      antisense oligonucleotide, can be RNA, DNA
      or chimera
<220> FEATURE:
<221> NAME/KEY: modified_base
<222> LOCATION: (3)
<223> OTHER INFORMATION: T or U
<220> FEATURE:
<221> NAME/KEY: modified_base
<222> LOCATION: (6)
<223> OTHER INFORMATION: T or U
```

```
<220> FEATURE:
<221> NAME/KEY: modified_base
<222> LOCATION: (8)
<223> OTHER INFORMATION: T or U
<220> FEATURE:
<221> NAME/KEY: modified_base
<222> LOCATION: (12)
<223> OTHER INFORMATION: T or U
<220> FEATURE:
<221> NAME/KEY: modified_base
<222> LOCATION: (17)
<223> OTHER INFORMATION: T or U
<220> FEATURE:
<221> NAME/KEY: modified_base
<222> LOCATION: (22)
<223> OTHER INFORMATION: T or U
<220> FEATURE:
<221> NAME/KEY: modified_base
<222> LOCATION: (24)
<223> OTHER INFORMATION: T or U

<400> SEQUENCE: 4
ggngangnag angaggnagg gngn                                          24

<210> SEQ ID NO 5
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic antisense oligonucleotide, can be
      RNA, DNA or chimera
<220> FEATURE:
<223> OTHER INFORMATION: Description of Artificial Sequence: Synthetic
      antisense oligonucleotide, can be RNA, DNA
      or chimera

<400> SEQUENCE: 5
aauucataat tctccttccc cau                                           23

<210> SEQ ID NO 6
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic antisense oligonucleotide, can be
      RNA, DNA or chimera
<220> FEATURE:
<223> OTHER INFORMATION: Description of Artificial Sequence: Synthetic
      antisense oligonucleotide, can be RNA, DNA
      or chimera

<400> SEQUENCE: 6
gugatataga taaggtaggg ugu                                           23

<210> SEQ ID NO 7
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic antisense oligonucleotide, can be
      RNA, DNA or chimera
<220> FEATURE:
<223> OTHER INFORMATION: Description of Artificial Sequence: Synthetic
      antisense oligonucleotide, can be RNA, DNA
      or chimera

<400> SEQUENCE: 7
ucauagttct cggccttccc cau                                           23
```

```
<210> SEQ ID NO 8
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic antisense oligonucleotide, can be
      RNA, DNA or chimera
<220> FEATURE:
<223> OTHER INFORMATION: Description of Artificial Sequence: Synthetic
      antisense oligonucleotide, can be RNA, DNA
      or chimera

<400> SEQUENCE: 8
ucauagttct cggccuuccc cau                                               23

<210> SEQ ID NO 9
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic antisense oligonucleotide, can be
      RNA, DNA or chimera
<220> FEATURE:
<223> OTHER INFORMATION: Description of Artificial Sequence: Synthetic
      antisense oligonucleotide, can be RNA, DNA
      or chimera

<400> SEQUENCE: 9
ucauaguucu cggccuuccc cau                                               23

<210> SEQ ID NO 10
<211> LENGTH: 22
<212> TYPE: DNA
<213> ORGANISM: Artificial Sequence
<220> FEATURE:
<223> OTHER INFORMATION: Description of Combined DNA/RNA Molecule:
      Synthetic antisense oligonucleotide, can be
      RNA, DNA or chimera
<220> FEATURE:
<223> OTHER INFORMATION: Description of Artificial Sequence: Synthetic
      antisense oligonucleotide, can be RNA, DNA
      or chimera

<400> SEQUENCE: 10
cauagutctc ggccttcccc au                                                22

<210> SEQ ID NO 11
<211> LENGTH: 22
<212> TYPE: DNA
<213> ORGANISM: Artificial Sequence
<220> FEATURE:
<223> OTHER INFORMATION: Description of Combined DNA/RNA Molecule:
      Synthetic antisense oligonucleotide, can be
      RNA, DNA or chimera
<220> FEATURE:
<223> OTHER INFORMATION: Description of Artificial Sequence: Synthetic
      antisense oligonucleotide, can be RNA, DNA
      or chimera

<400> SEQUENCE: 11
cauagttctc ggccuucccc au                                                22

<210> SEQ ID NO 12
<211> LENGTH: 22
<212> TYPE: DNA
<213> ORGANISM: Artificial Sequence
```

```
<220> FEATURE:
<223> OTHER INFORMATION: Description of Combined DNA/RNA Molecule:
      Synthetic antisense oligonucleotide, can be
      RNA, DNA or chimera
<220> FEATURE:
<223> OTHER INFORMATION: Description of Artificial Sequence: Synthetic
      antisense oligonucleotide, can be RNA, DNA
      or chimera

<400> SEQUENCE: 12
catagttctc ggccttcccc at                                              22

<210> SEQ ID NO 13
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic antisense oligonucleotide, can be
      RNA, DNA or chimera
<220> FEATURE:
<223> OTHER INFORMATION: Description of Artificial Sequence: Synthetic
      antisense oligonucleotide, can be RNA, DNA
      or chimera

<400> SEQUENCE: 13
catagttctc ggccttcccc atg                                             23

<210> SEQ ID NO 14
<211> LENGTH: 24
<212> TYPE: DNA
<213> ORGANISM: Artificial Sequence
<220> FEATURE:
<223> OTHER INFORMATION: Description of Combined DNA/RNA Molecule:
      Synthetic antisense oligonucleotide, can be
      RNA, DNA or chimera
<220> FEATURE:
<223> OTHER INFORMATION: Description of Artificial Sequence: Synthetic
      antisense oligonucleotide, can be RNA, DNA
      or chimera

<400> SEQUENCE: 14
catagttctc ggccttcccc atgg                                            24

<210> SEQ ID NO 15
<211> LENGTH: 25
<212> TYPE: DNA
<213> ORGANISM: Artificial Sequence
<220> FEATURE:
<223> OTHER INFORMATION: Description of Combined DNA/RNA Molecule:
      Synthetic antisense oligonucleotide, can be
      RNA, DNA or chimera
<220> FEATURE:
<223> OTHER INFORMATION: Description of Artificial Sequence: Synthetic
      antisense oligonucleotide, can be RNA, DNA
      or chimera

<400> SEQUENCE: 15
catagttctc ggccttcccc atggt                                           25

<210> SEQ ID NO 16
<211> LENGTH: 20
<212> TYPE: DNA
<213> ORGANISM: Artificial Sequence
<220> FEATURE:
<223> OTHER INFORMATION: Description of Combined DNA/RNA Molecule:
      Synthetic antisense oligonucleotide, can be
      RNA, DNA or chimera
```

-continued

```
<220> FEATURE:
<223> OTHER INFORMATION: Description of Artificial Sequence: Synthetic
      antisense oligonucleotide, can be RNA, DNA
      or chimera

<400> SEQUENCE: 16
gugaugtaga tgagguaggg                                                    20

<210> SEQ ID NO 17
<211> LENGTH: 22
<212> TYPE: DNA
<213> ORGANISM: Artificial Sequence
<220> FEATURE:
<223> OTHER INFORMATION: Description of Combined DNA/RNA Molecule:
      Synthetic antisense oligonucleotide, can be
      RNA, DNA or chimera
<220> FEATURE:
<223> OTHER INFORMATION: Description of Artificial Sequence: Synthetic
      antisense oligonucleotide, can be RNA, DNA
      or chimera
<220> FEATURE:
<221> NAME/KEY: modified_base
<222> LOCATION: (3)
<223> OTHER INFORMATION: T or U
<220> FEATURE:
<221> NAME/KEY: modified_base
<222> LOCATION: (6)..(7)
<223> OTHER INFORMATION: T or U
<220> FEATURE:
<221> NAME/KEY: modified_base
<222> LOCATION: (9)
<223> OTHER INFORMATION: T or U
<220> FEATURE:
<221> NAME/KEY: modified_base
<222> LOCATION: (15)..(16)
<223> OTHER INFORMATION: T or U
<220> FEATURE:
<221> NAME/KEY: modified_base
<222> LOCATION: (22)
<223> OTHER INFORMATION: T or U

<400> SEQUENCE: 17
canagnncnc ggccnncccc an                                                 22

<210> SEQ ID NO 18
<211> LENGTH: 20
<212> TYPE: DNA
<213> ORGANISM: Artificial Sequence
<220> FEATURE:
<223> OTHER INFORMATION: Description of Combined DNA/RNA Molecule:
      Synthetic antisense oligonucleotide, can be
      RNA, DNA or chimera
<220> FEATURE:
<223> OTHER INFORMATION: Description of Artificial Sequence: Synthetic
      antisense oligonucleotide, can be RNA, DNA
      or chimera
<220> FEATURE:
<221> NAME/KEY: modified_base
<222> LOCATION: (3)
<223> OTHER INFORMATION: T or U
<220> FEATURE:
<221> NAME/KEY: modified_base
<222> LOCATION: (6)..(7)
<223> OTHER INFORMATION: T or U
<220> FEATURE:
<221> NAME/KEY: modified_base
<222> LOCATION: (9)
<223> OTHER INFORMATION: T or U
<220> FEATURE:
<221> NAME/KEY: modified_base
<222> LOCATION: (15)..(16)
<223> OTHER INFORMATION: T or U
```

-continued

```
<400> SEQUENCE: 18
canagnncnc ggccnncccc                                                    20

<210> SEQ ID NO 19
<211> LENGTH: 18
<212> TYPE: DNA
<213> ORGANISM: Artificial Sequence
<220> FEATURE:
<223> OTHER INFORMATION: Description of Combined DNA/RNA Molecule:
      Synthetic antisense oligonucleotide, can be
      RNA, DNA or chimera
<220> FEATURE:
<223> OTHER INFORMATION: Description of Artificial Sequence: Synthetic
      antisense oligonucleotide, can be RNA, DNA
      or chimera
<220> FEATURE:
<221> NAME/KEY: modified_base
<222> LOCATION: (3)
<223> OTHER INFORMATION: T or U
<220> FEATURE:
<221> NAME/KEY: modified_base
<222> LOCATION: (6)..(7)
<223> OTHER INFORMATION: T or U
<220> FEATURE:
<221> NAME/KEY: modified_base
<222> LOCATION: (9)
<223> OTHER INFORMATION: T or U
<220> FEATURE:
<221> NAME/KEY: modified_base
<222> LOCATION: (15)..(16)
<223> OTHER INFORMATION: T or U

<400> SEQUENCE: 19
canagnncnc ggccnncc                                                      18

<210> SEQ ID NO 20
<211> LENGTH: 15
<212> TYPE: DNA
<213> ORGANISM: Artificial Sequence
<220> FEATURE:
<223> OTHER INFORMATION: Description of Combined DNA/RNA Molecule:
      Synthetic antisense oligonucleotide, can be
      RNA, DNA or chimera
<220> FEATURE:
<223> OTHER INFORMATION: Description of Artificial Sequence: Synthetic
      antisense oligonucleotide, can be RNA, DNA
      or chimera
<220> FEATURE:
<221> NAME/KEY: modified_base
<222> LOCATION: (3)
<223> OTHER INFORMATION: T or U
<220> FEATURE:
<221> NAME/KEY: modified_base
<222> LOCATION: (6)..(7)
<223> OTHER INFORMATION: T or U
<220> FEATURE:
<221> NAME/KEY: modified_base
<222> LOCATION: (9)
<223> OTHER INFORMATION: T or U
<220> FEATURE:
<221> NAME/KEY: modified_base
<222> LOCATION: (15)
<223> OTHER INFORMATION: T or U

<400> SEQUENCE: 20
canagnncnc ggccn                                                         15

<210> SEQ ID NO 21
<211> LENGTH: 14
<212> TYPE: DNA
<213> ORGANISM: Artificial Sequence
```

```
<220> FEATURE:
<223> OTHER INFORMATION: Description of Combined DNA/RNA Molecule:
      Synthetic antisense oligonucleotide, can be
      RNA, DNA or chimera
<220> FEATURE:
<223> OTHER INFORMATION: Description of Artificial Sequence: Synthetic
      antisense oligonucleotide, can be RNA, DNA
      or chimera
<220> FEATURE:
<221> NAME/KEY: modified_base
<222> LOCATION: (3)
<223> OTHER INFORMATION: T or U
<220> FEATURE:
<221> NAME/KEY: modified_base
<222> LOCATION: (6)..(7)
<223> OTHER INFORMATION: T or U
<220> FEATURE:
<221> NAME/KEY: modified_base
<222> LOCATION: (9)
<223> OTHER INFORMATION: T or U

<400> SEQUENCE: 21
canagnncnc ggcc                                                       14

<210> SEQ ID NO 22
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic antisense oligonucleotide, can be
      RNA, DNA or chimera
<220> FEATURE:
<223> OTHER INFORMATION: Description of Artificial Sequence: Synthetic
      antisense oligonucleotide, can be RNA, DNA
      or chimera

<400> SEQUENCE: 22
uaccccttcc tcttaatacu uaa                                             23

<210> SEQ ID NO 23
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic antisense oligonucleotide, can be
      RNA, DNA or chimera
<220> FEATURE:
<223> OTHER INFORMATION: Description of Artificial Sequence: Synthetic
      antisense oligonucleotide, can be RNA, DNA
      or chimera

<400> SEQUENCE: 23
aattcataat tctccttccc c                                               21

<210> SEQ ID NO 24
<211> LENGTH: 18
<212> TYPE: DNA
<213> ORGANISM: Artificial Sequence
<220> FEATURE:
<223> OTHER INFORMATION: Description of Combined DNA/RNA Molecule:
      Synthetic antisense oligonucleotide, can be
      RNA, DNA or chimera
<220> FEATURE:
<223> OTHER INFORMATION: Description of Artificial Sequence: Synthetic
      antisense oligonucleotide, can be RNA, DNA
      or chimera

<400> SEQUENCE: 24
aattcataat tctccttc                                                   18
```

<210> SEQ ID NO 25
<211> LENGTH: 15
<212> TYPE: DNA
<213> ORGANISM: Artificial Sequence
<220> FEATURE:
<223> OTHER INFORMATION: Description of Combined DNA/RNA Molecule:
      Synthetic antisense oligonucleotide, can be
      RNA, DNA or chimera
<220> FEATURE:
<223> OTHER INFORMATION: Description of Artificial Sequence: Synthetic
      antisense oligonucleotide, can be RNA, DNA
      or chimera

<400> SEQUENCE: 25
aattcataat tctcc                                                         15

<210> SEQ ID NO 26
<211> LENGTH: 26
<212> TYPE: DNA
<213> ORGANISM: Artificial Sequence
<220> FEATURE:
<223> OTHER INFORMATION: Description of Combined DNA/RNA Molecule:
      Synthetic antisense oligonucleotide, can be
      RNA, DNA or chimera
<220> FEATURE:
<223> OTHER INFORMATION: Description of Artificial Sequence: Synthetic
      antisense oligonucleotide, can be RNA, DNA
      or chimera

<400> SEQUENCE: 26
aattcataat tctccttcga gaatta                                             26

<210> SEQ ID NO 27
<211> LENGTH: 31
<212> TYPE: DNA
<213> ORGANISM: Artificial Sequence
<220> FEATURE:
<223> OTHER INFORMATION: Description of Combined DNA/RNA Molecule:
      Synthetic antisense oligonucleotide, can be
      RNA, DNA or chimera
<220> FEATURE:
<223> OTHER INFORMATION: Description of Artificial Sequence: Synthetic
      antisense oligonucleotide, can be RNA, DNA
      or chimera

<400> SEQUENCE: 27
gugatataga taaggtaggg ugucctacct t                                       31

<210> SEQ ID NO 28
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic antisense oligonucleotide, can be
      RNA, DNA or chimera
<220> FEATURE:
<223> OTHER INFORMATION: Description of Artificial Sequence: Synthetic
      antisense oligonucleotide, can be RNA, DNA
      or chimera

<400> SEQUENCE: 28
ggtgatgtag atgaggtagg g                                                  21

<210> SEQ ID NO 29
<211> LENGTH: 20
<212> TYPE: RNA
<213> ORGANISM: Artificial Sequence

```
<220> FEATURE:
<223> OTHER INFORMATION: Description of Combined DNA/RNA Molecule:
      Synthetic antisense oligonucleotide, can be
      RNA, DNA or chimera
<220> FEATURE:
<223> OTHER INFORMATION: Description of Artificial Sequence: Synthetic
      antisense oligonucleotide, can be RNA, DNA
      or chimera

<400> SEQUENCE: 29
ucuucucguu uuccaccccc                                                      20

<210> SEQ ID NO 30
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic antisense oligonucleotide, can be
      RNA, DNA or chimera
<220> FEATURE:
<223> OTHER INFORMATION: Description of Artificial Sequence: Synthetic
      antisense oligonucleotide, can be RNA, DNA
      or chimera

<400> SEQUENCE: 30
gtgucuucuc guuuuccacc ccc                                                  23

<210> SEQ ID NO 31
<211> LENGTH: 22
<212> TYPE: RNA
<213> ORGANISM: Artificial Sequence
<220> FEATURE:
<223> OTHER INFORMATION: Description of Combined DNA/RNA Molecule:
      Synthetic antisense oligonucleotide, can be
      RNA, DNA or chimera
<220> FEATURE:
<223> OTHER INFORMATION: Description of Artificial Sequence: Synthetic
      antisense oligonucleotide, can be RNA, DNA
      or chimera

<400> SEQUENCE: 31
ucuucucguu uuccaccccc ga                                                   22

<210> SEQ ID NO 32
<211> LENGTH: 25
<212> TYPE: DNA
<213> ORGANISM: Artificial Sequence
<220> FEATURE:
<223> OTHER INFORMATION: Description of Combined DNA/RNA Molecule:
      Synthetic antisense oligonucleotide, can be
      RNA, DNA or chimera
<220> FEATURE:
<223> OTHER INFORMATION: Description of Artificial Sequence: Synthetic
      antisense oligonucleotide, can be RNA, DNA
      or chimera

<400> SEQUENCE: 32
gtgucuucuc guuuuccacc cccga                                                25

<210> SEQ ID NO 33
<211> LENGTH: 19
<212> TYPE: DNA
<213> ORGANISM: Artificial Sequence
<220> FEATURE:
<223> OTHER INFORMATION: Description of Combined DNA/RNA Molecule:
      Synthetic antisense oligonucleotide, can be
      RNA, DNA or chimera
```

```
<220> FEATURE:
<223> OTHER INFORMATION: Description of Artificial Sequence: Synthetic
      antisense oligonucleotide, can be RNA, DNA
      or chimera

<400> SEQUENCE: 33
cagggacaca gaugggaaa                                                    19

<210> SEQ ID NO 34
<211> LENGTH: 18
<212> TYPE: DNA
<213> ORGANISM: Artificial Sequence
<220> FEATURE:
<223> OTHER INFORMATION: Description of Combined DNA/RNA Molecule:
      Synthetic antisense oligonucleotide, can be
      RNA, DNA or chimera
<220> FEATURE:
<223> OTHER INFORMATION: Description of Artificial Sequence: Synthetic
      antisense oligonucleotide, can be RNA, DNA
      or chimera

<400> SEQUENCE: 34
agaugggaaa augucagu                                                     18

<210> SEQ ID NO 35
<211> LENGTH: 17
<212> TYPE: DNA
<213> ORGANISM: Artificial Sequence
<220> FEATURE:
<223> OTHER INFORMATION: Description of Combined DNA/RNA Molecule:
      Synthetic antisense oligonucleotide, can be
      RNA, DNA or chimera
<220> FEATURE:
<223> OTHER INFORMATION: Description of Artificial Sequence: Synthetic
      antisense oligonucleotide, can be RNA, DNA
      or chimera

<400> SEQUENCE: 35
uaaguucaga aacaccc                                                      17

<210> SEQ ID NO 36
<211> LENGTH: 18
<212> TYPE: DNA
<213> ORGANISM: Artificial Sequence
<220> FEATURE:
<223> OTHER INFORMATION: Description of Combined DNA/RNA Molecule:
      Synthetic antisense oligonucleotide, can be
      RNA, DNA or chimera
<220> FEATURE:
<223> OTHER INFORMATION: Description of Artificial Sequence: Synthetic
      antisense oligonucleotide, can be RNA, DNA
      or chimera

<400> SEQUENCE: 36 cauuuuggc agcaucuc                                                      18

<210> SEQ ID NO 37
<211> LENGTH: 15
<212> TYPE: DNA
<213> ORGANISM: Artificial Sequence
<220> FEATURE:
<223> OTHER INFORMATION: Description of Combined DNA/RNA Molecule:
      Synthetic antisense oligonucleotide, can be
      RNA, DNA or chimera
<220> FEATURE:
<223> OTHER INFORMATION: Description of Artificial Sequence: Synthetic
      antisense oligonucleotide, can be RNA, DNA
      or chimera
```

```
<400> SEQUENCE: 37
caaaguuguc aucca                                                    15

<210> SEQ ID NO 38
<211> LENGTH: 16
<212> TYPE: DNA
<213> ORGANISM: Artificial Sequence
<220> FEATURE:
<223> OTHER INFORMATION: Description of Combined DNA/RNA Molecule:
      Synthetic antisense oligonucleotide, can be
      RNA, DNA or chimera
<220> FEATURE:
<223> OTHER INFORMATION: Description of Artificial Sequence: Synthetic
      antisense oligonucleotide, can be RNA, DNA
      or chimera

<400> SEQUENCE: 38
caaaguuguc auccag                                                   16

<210> SEQ ID NO 39
<211> LENGTH: 16
<212> TYPE: DNA
<213> ORGANISM: Artificial Sequence
<220> FEATURE:
<223> OTHER INFORMATION: Description of Combined DNA/RNA Molecule:
      Synthetic antisense oligonucleotide, can be
      RNA, DNA or chimera
<220> FEATURE:
<223> OTHER INFORMATION: Description of Artificial Sequence: Synthetic
      antisense oligonucleotide, can be RNA, DNA
      or chimera

<400> SEQUENCE: 39
ctaauaguag aguucc                                                   16

<210> SEQ ID NO 40
<211> LENGTH: 18
<212> TYPE: DNA
<213> ORGANISM: Artificial Sequence
<220> FEATURE:
<223> OTHER INFORMATION: Description of Combined DNA/RNA Molecule:
      Synthetic antisense oligonucleotide, can be
      RNA, DNA or chimera
<220> FEATURE:
<223> OTHER INFORMATION: Description of Artificial Sequence: Synthetic
      antisense oligonucleotide, can be RNA, DNA
      or chimera

<400> SEQUENCE: 40
tgaagtagtc agtgaagc                                                 18

<210> SEQ ID NO 41
<211> LENGTH: 16
<212> TYPE: DNA
<213> ORGANISM: Artificial Sequence
<220> FEATURE:
<223> OTHER INFORMATION: Description of Combined DNA/RNA Molecule:
      Synthetic antisense oligonucleotide, can be
      RNA, DNA or chimera
<220> FEATURE:
<223> OTHER INFORMATION: Description of Artificial Sequence: Synthetic
      antisense oligonucleotide, can be RNA, DNA
      or chimera

<400> SEQUENCE: 41
aagtagtcag tgaagc                                                   16
```

```
<210> SEQ ID NO 42
<211> LENGTH: 16
<212> TYPE: DNA
<213> ORGANISM: Artificial Sequence
<220> FEATURE:
<223> OTHER INFORMATION: Description of Combined DNA/RNA Molecule:
      Synthetic antisense oligonucleotide, can be
      RNA, DNA or chimera
<220> FEATURE:
<223> OTHER INFORMATION: Description of Artificial Sequence: Synthetic
      antisense oligonucleotide, can be RNA, DNA
      or chimera

<400> SEQUENCE: 42
tggcgatgat gttggt                                                       16

<210> SEQ ID NO 43
<211> LENGTH: 16
<212> TYPE: DNA
<213> ORGANISM: Artificial Sequence
<220> FEATURE:
<223> OTHER INFORMATION: Description of Combined DNA/RNA Molecule:
      Synthetic antisense oligonucleotide, can be
      RNA, DNA or chimera
<220> FEATURE:
<223> OTHER INFORMATION: Description of Artificial Sequence: Synthetic
      antisense oligonucleotide, can be RNA, DNA
      or chimera

<400> SEQUENCE: 43
gctagatgga aagttc                                                       16

<210> SEQ ID NO 44
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic antisense oligonucleotide, can be
      RNA, DNA or chimera
<220> FEATURE:
<223> OTHER INFORMATION: Description of Artificial Sequence: Synthetic
      antisense oligonucleotide, can be RNA, DNA
      or chimera

<400> SEQUENCE: 44
aggccgctag atggaaagtt c                                                 21

<210> SEQ ID NO 45
<211> LENGTH: 15
<212> TYPE: DNA
<213> ORGANISM: Artificial Sequence
<220> FEATURE:
<223> OTHER INFORMATION: Description of Combined DNA/RNA Molecule:
      Synthetic antisense oligonucleotide, can be
      RNA, DNA or chimera
<220> FEATURE:
<223> OTHER INFORMATION: Description of Artificial Sequence: Synthetic
      antisense oligonucleotide, can be RNA, DNA
      or chimera

<400> SEQUENCE: 45
cacagcauca gggac                                                        15

<210> SEQ ID NO 46
<211> LENGTH: 16
<212> TYPE: DNA
<213> ORGANISM: Artificial Sequence
```

```
<220> FEATURE:
<223> OTHER INFORMATION: Description of Combined DNA/RNA Molecule:
      Synthetic antisense oligonucleotide, can be
      RNA, DNA or chimera
<220> FEATURE:
<223> OTHER INFORMATION: Description of Artificial Sequence: Synthetic
      antisense oligonucleotide, can be RNA, DNA
      or chimera

<400> SEQUENCE: 46
gggcacacgg aggcgg                                                    16

<210> SEQ ID NO 47
<211> LENGTH: 16
<212> TYPE: DNA
<213> ORGANISM: Artificial Sequence
<220> FEATURE:
<223> OTHER INFORMATION: Description of Combined DNA/RNA Molecule:
      Synthetic antisense oligonucleotide, can be
      RNA, DNA or chimera
<220> FEATURE:
<223> OTHER INFORMATION: Description of Artificial Sequence: Synthetic
      antisense oligonucleotide, can be RNA, DNA
      or chimera

<400> SEQUENCE: 47
cgaugcgccc aaugau                                                    16

<210> SEQ ID NO 48
<211> LENGTH: 18
<212> TYPE: DNA
<213> ORGANISM: Artificial Sequence
<220> FEATURE:
<223> OTHER INFORMATION: Description of Combined DNA/RNA Molecule:
      Synthetic antisense oligonucleotide, can be
      RNA, DNA or chimera
<220> FEATURE:
<223> OTHER INFORMATION: Description of Artificial Sequence: Synthetic
      antisense oligonucleotide, can be RNA, DNA
      or chimera

<400> SEQUENCE: 48
auaaaaaaug uggcaccg                                                  18

<210> SEQ ID NO 49
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic antisense oligonucleotide, can be
      RNA, DNA or chimera
<220> FEATURE:
<223> OTHER INFORMATION: Description of Artificial Sequence: Synthetic
      antisense oligonucleotide, can be RNA, DNA
      or chimera

<400> SEQUENCE: 49
cacauggcca caauaaaaaa u                                              21

<210> SEQ ID NO 50
<211> LENGTH: 16
<212> TYPE: DNA
<213> ORGANISM: Artificial Sequence
<220> FEATURE:
<223> OTHER INFORMATION: Description of Combined DNA/RNA Molecule:
      Synthetic antisense oligonucleotide, can be
      RNA, DNA or chimera
```

```
<220> FEATURE:
<223> OTHER INFORMATION: Description of Artificial Sequence: Synthetic
      antisense oligonucleotide, can be RNA, DNA
      or chimera

<400> SEQUENCE: 50 gugugucag cugugu                                                          16

<210> SEQ ID NO 51
<211> LENGTH: 13
<212> TYPE: DNA
<213> ORGANISM: Artificial Sequence
<220> FEATURE:
<223> OTHER INFORMATION: Description of Combined DNA/RNA Molecule:
      Synthetic antisense oligonucleotide, can be
      RNA, DNA or chimera
<220> FEATURE:
<223> OTHER INFORMATION: Description of Artificial Sequence: Synthetic
      antisense oligonucleotide, can be RNA, DNA
      or chimera

<400> SEQUENCE: 51
ugauggggug guc                                                            13

<210> SEQ ID NO 52
<211> LENGTH: 17
<212> TYPE: DNA
<213> ORGANISM: Artificial Sequence
<220> FEATURE:
<223> OTHER INFORMATION: Description of Combined DNA/RNA Molecule:
      Synthetic antisense oligonucleotide, can be
      RNA, DNA or chimera
<220> FEATURE:
<223> OTHER INFORMATION: Description of Artificial Sequence: Synthetic
      antisense oligonucleotide, can be RNA, DNA
      or chimera

<400> SEQUENCE: 52
cuuguaggug guggucc                                                        17

<210> SEQ ID NO 53
<211> LENGTH: 17
<212> TYPE: DNA
<213> ORGANISM: Artificial Sequence
<220> FEATURE:
<223> OTHER INFORMATION: Description of Combined DNA/RNA Molecule:
      Synthetic antisense oligonucleotide, can be
      RNA, DNA or chimera
<220> FEATURE:
<223> OTHER INFORMATION: Description of Artificial Sequence: Synthetic
      antisense oligonucleotide, can be RNA, DNA
      or chimera

<400> SEQUENCE: 53
uugaaggcag ucguccc                                                        17

<210> SEQ ID NO 54
<211> LENGTH: 14
<212> TYPE: DNA
<213> ORGANISM: Artificial Sequence
<220> FEATURE:
<223> OTHER INFORMATION: Description of Combined DNA/RNA Molecule:
      Synthetic antisense oligonucleotide, can be
      RNA, DNA or chimera
<220> FEATURE:
<223> OTHER INFORMATION: Description of Artificial Sequence: Synthetic
      antisense oligonucleotide, can be RNA, DNA
      or chimera
```

```
<400> SEQUENCE: 54
ttgctcagat atca                                                          14

<210> SEQ ID NO 55
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic antisense oligonucleotide, can be
      RNA, DNA or chimera
<220> FEATURE:
<223> OTHER INFORMATION: Description of Artificial Sequence: Synthetic
      antisense oligonucleotide, can be RNA, DNA
      or chimera

<400> SEQUENCE: 55
catctccttc ttcatgttct c                                                  21

<210> SEQ ID NO 56
<211> LENGTH: 22
<212> TYPE: DNA
<213> ORGANISM: Artificial Sequence
<220> FEATURE:
<223> OTHER INFORMATION: Description of Combined DNA/RNA Molecule:
      Synthetic antisense oligonucleotide, can be
      RNA, DNA or chimera
<220> FEATURE:
<223> OTHER INFORMATION: Description of Artificial Sequence: Synthetic
      antisense oligonucleotide, can be RNA, DNA
      or chimera

<400> SEQUENCE: 56
tagtccttct cattcaggta ga                                                 22

<210> SEQ ID NO 57
<211> LENGTH: 18
<212> TYPE: DNA
<213> ORGANISM: Artificial Sequence
<220> FEATURE:
<223> OTHER INFORMATION: Description of Combined DNA/RNA Molecule:
      Synthetic antisense oligonucleotide, can be
      RNA, DNA or chimera
<220> FEATURE:
<223> OTHER INFORMATION: Description of Artificial Sequence: Synthetic
      antisense oligonucleotide, can be RNA, DNA
      or chimera

<400> SEQUENCE: 57
tggaagtagg agtaggca                                                      18

<210> SEQ ID NO 58
<211> LENGTH: 19
<212> TYPE: DNA
<213> ORGANISM: Artificial Sequence
<220> FEATURE:
<223> OTHER INFORMATION: Description of Combined DNA/RNA Molecule:
      Synthetic antisense oligonucleotide, can be
      RNA, DNA or chimera
<220> FEATURE:
<223> OTHER INFORMATION: Description of Artificial Sequence: Synthetic
      antisense oligonucleotide, can be RNA, DNA
      or chimera

<400> SEQUENCE: 58
gagagacgct gaggacagt                                                     19
```

<210> SEQ ID NO 59
<211> LENGTH: 20
<212> TYPE: DNA
<213> ORGANISM: Homo sapiens

<400> SEQUENCE: 59
atggggaagg ccgtgagtgg                                              20

<210> SEQ ID NO 60
<211> LENGTH: 20
<212> TYPE: DNA
<213> ORGANISM: Artificial Sequence
<220> FEATURE:
<223> OTHER INFORMATION: Description of Combined DNA/RNA Molecule:
      Synthetic antisense oligonucleotide, can be
      RNA, DNA or chimera
<220> FEATURE:
<223> OTHER INFORMATION: Description of Artificial Sequence: Synthetic
      antisense oligonucleotide, can be RNA, DNA
      or chimera

<400> SEQUENCE: 60
ccactcacgg ccttccccat                                              20

<210> SEQ ID NO 61
<211> LENGTH: 20
<212> TYPE: DNA
<213> ORGANISM: Artificial Sequence
<220> FEATURE:
<223> OTHER INFORMATION: Description of Combined DNA/RNA Molecule:
      Synthetic antisense oligonucleotide, can be
      RNA, DNA or chimera
<220> FEATURE:
<223> OTHER INFORMATION: Description of Artificial Sequence: Synthetic
      antisense oligonucleotide, can be RNA, DNA
      or chimera

<400> SEQUENCE: 61
ccactcactg ccttccccat                                              20

<210> SEQ ID NO 62
<211> LENGTH: 30
<212> TYPE: DNA
<213> ORGANISM: Homo sapiens

<400> SEQUENCE: 62
tgttgggtgg gagcacaggc accgggcacc                                   30

<210> SEQ ID NO 63
<211> LENGTH: 26
<212> TYPE: DNA
<213> ORGANISM: Artificial Sequence
<220> FEATURE:
<223> OTHER INFORMATION: Description of Combined DNA/RNA Molecule:
      Synthetic antisense oligonucleotide, can be
      RNA, DNA or chimera
<220> FEATURE:
<223> OTHER INFORMATION: Description of Artificial Sequence: Synthetic
      antisense oligonucleotide, can be RNA, DNA
      or chimera

<400> SEQUENCE: 63
cccggugccu gugcucccac ccaaca                                       26

<210> SEQ ID NO 64
<211> LENGTH: 29
<212> TYPE: DNA
<213> ORGANISM: Artificial Sequence

```
<220> FEATURE:
<223> OTHER INFORMATION: Description of Combined DNA/RNA Molecule:
      Synthetic antisense oligonucleotide, can be
      RNA, DNA or chimera
<220> FEATURE:
<223> OTHER INFORMATION: Description of Artificial Sequence: Synthetic
      antisense oligonucleotide, can be RNA, DNA
      or chimera

<400> SEQUENCE: 64
ggtgatgtag atgaggtagg gacctcatc                                            29

<210> SEQ ID NO 65
<211> LENGTH: 26
<212> TYPE: DNA
<213> ORGANISM: Artificial Sequence
<220> FEATURE:
<223> OTHER INFORMATION: Description of Combined DNA/RNA Molecule:
      Synthetic antisense oligonucleotide, can be
      RNA, DNA or chimera
<220> FEATURE:
<223> OTHER INFORMATION: Description of Artificial Sequence: Synthetic
      antisense oligonucleotide, can be RNA, DNA
      or chimera

<400> SEQUENCE: 65
cccggtgcct gtgctcccac ccaaca                                               26

<210> SEQ ID NO 66
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 66
cugaugaguc cgugaggacg aa                                                   22

<210> SEQ ID NO 67
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)
<223> OTHER INFORMATION: a, u, c, g, other or unknown
<220> FEATURE:
<221> NAME/KEY: modified_base
<222> LOCATION: (9)
<223> OTHER INFORMATION: a, u, c, g, other or unknown
<220> FEATURE:
<221> NAME/KEY: modified_base
<222> LOCATION: (11)..(12)
<223> OTHER INFORMATION: a, u, c, g, other or unknown
<220> FEATURE:
<221> NAME/KEY: modified_base
<222> LOCATION: (14)
<223> OTHER INFORMATION: a, u, c, g, other or unknown

<400> SEQUENCE: 67
cugangagnc nngncgaaac                                                      20

<210> SEQ ID NO 68
<211> LENGTH: 36
<212> TYPE: RNA
<213> ORGANISM: Artificial Sequence
```

```
-continued

<220> FEATURE:
<223> OTHER INFORMATION: Description of Artificial Sequence: Synthetic
      oligonucleotide

<400> SEQUENCE: 68
augguccauu auaugguguu gcacacaaag agacca                              36

<210> SEQ ID NO 69
<211> LENGTH: 42
<212> TYPE: DNA
<213> ORGANISM: Artificial Sequence
<220> FEATURE:
<223> OTHER INFORMATION: Description of Combined DNA/RNA Molecule:
      Synthetic ribozyme oligonucleotide
<220> FEATURE:
<223> OTHER INFORMATION: Description of Artificial Sequence: Synthetic
      ribozyme oligonucleotide

<400> SEQUENCE: 69
aguccuaagc ugaugagucc gugaggacga acagaaacac cc                       42

<210> SEQ ID NO 70
<211> LENGTH: 35
<212> TYPE: DNA
<213> ORGANISM: Artificial Sequence
<220> FEATURE:
<223> OTHER INFORMATION: Description of Combined DNA/RNA Molecule:
      Synthetic ribozyme oligonucleotide
<220> FEATURE:
<223> OTHER INFORMATION: Description of Artificial Sequence: Synthetic
      ribozyme oligonucleotide

<400> SEQUENCE: 70
ggctggcuga ugaguccgug aggacgaact cttgg                               35

<210> SEQ ID NO 71
<211> LENGTH: 12
<212> TYPE: DNA
<213> ORGANISM: Artificial Sequence
<220> FEATURE:
<223> OTHER INFORMATION: Description of Combined DNA/RNA Molecule:
      Synthetic antisense oligonucleotide, can be
      RNA, DNA or chimera
<220> FEATURE:
<223> OTHER INFORMATION: Description of Artificial Sequence: Synthetic
      antisense oligonucleotide, can be RNA, DNA
      or chimera

<400> SEQUENCE: 71
gtcgggcggt tc                                                        12

<210> SEQ ID NO 72
<211> LENGTH: 12
<212> TYPE: DNA
<213> ORGANISM: Artificial Sequence
<220> FEATURE:
<223> OTHER INFORMATION: Description of Combined DNA/RNA Molecule:
      Synthetic antisense oligonucleotide, can be
      RNA, DNA or chimera
<220> FEATURE:
<223> OTHER INFORMATION: Description of Artificial Sequence: Synthetic
      antisense oligonucleotide, can be RNA, DNA
      or chimera

<400> SEQUENCE: 72
gaaccgcccg ac                                                        12
```

<210> SEQ ID NO 73
<211> LENGTH: 12
<212> TYPE: DNA
<213> ORGANISM: Artificial Sequence
<220> FEATURE:
<223> OTHER INFORMATION: Description of Combined DNA/RNA Molecule:
      Synthetic antisense oligonucleotide, can be
      RNA, DNA or chimera
<220> FEATURE:
<223> OTHER INFORMATION: Description of Artificial Sequence: Synthetic
      antisense oligonucleotide, can be RNA, DNA
      or chimera

<400> SEQUENCE: 73
cacccgccct cc                                                      12

<210> SEQ ID NO 74
<211> LENGTH: 12
<212> TYPE: DNA
<213> ORGANISM: Artificial Sequence
<220> FEATURE:
<223> OTHER INFORMATION: Description of Combined DNA/RNA Molecule:
      Synthetic antisense oligonucleotide, can be
      RNA, DNA or chimera
<220> FEATURE:
<223> OTHER INFORMATION: Description of Artificial Sequence: Synthetic
      antisense oligonucleotide, can be RNA, DNA
      or chimera

<400> SEQUENCE: 74
ggagggcggg tg                                                      12

<210> SEQ ID NO 75
<211> LENGTH: 21
<212> TYPE: DNA
<213> ORGANISM: Homo sapiens

<400> SEQUENCE: 75
agggagggcg gtggggtgga g                                            21

<210> SEQ ID NO 76
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic antisense oligonucleotide, can be
      RNA, DNA or chimera
<220> FEATURE:
<223> OTHER INFORMATION: Description of Artificial Sequence: Synthetic
      antisense oligonucleotide, can be RNA, DNA
      or chimera

<400> SEQUENCE: 76
gaggmggggm ggkgggaggg a                                            21

<210> SEQ ID NO 77
<211> LENGTH: 11
<212> TYPE: DNA
<213> ORGANISM: Artificial Sequence
<220> FEATURE:
<223> OTHER INFORMATION: Description of Combined DNA/RNA Molecule:
      Synthetic antisense oligonucleotide, can be
      RNA, DNA or chimera
<220> FEATURE:
<223> OTHER INFORMATION: Description of Artificial Sequence: Synthetic
      antisense oligonucleotide, can be RNA, DNA
      or chimera

```
<400> SEQUENCE: 77
ggkgggaggg a                                                        11

<210> SEQ ID NO 78
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic antisense oligonucleotide, can be
      RNA, DNA or chimera
<220> FEATURE:
<223> OTHER INFORMATION: Description of Artificial Sequence: Synthetic
      antisense oligonucleotide, can be RNA, DNA
      or chimera

<400> SEQUENCE: 78
ccacccggtg gtgggaggga tcc                                           23

<210> SEQ ID NO 79
<211> LENGTH: 22
<212> TYPE: DNA
<213> ORGANISM: Artificial Sequence
<220> FEATURE:
<223> OTHER INFORMATION: Description of Combined DNA/RNA Molecule:
      Synthetic antisense oligonucleotide, can be
      RNA, DNA or chimera
<220> FEATURE:
<223> OTHER INFORMATION: Description of Artificial Sequence: Synthetic
      antisense oligonucleotide, can be RNA, DNA
      or chimera

<400> SEQUENCE: 79
gtggmggggg mggkgggtgg gt                                            22

<210> SEQ ID NO 80
<211> LENGTH: 11
<212> TYPE: DNA
<213> ORGANISM: Artificial Sequence
<220> FEATURE:
<223> OTHER INFORMATION: Description of Combined DNA/RNA Molecule:
      Synthetic antisense oligonucleotide, can be
      RNA, DNA or chimera
<220> FEATURE:
<223> OTHER INFORMATION: Description of Artificial Sequence: Synthetic
      antisense oligonucleotide, can be RNA, DNA
      or chimera

<400> SEQUENCE: 80
ggtgggtggg t                                                        11

<210> SEQ ID NO 81
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic antisense oligonucleotide, can be
      RNA, DNA or chimera
<220> FEATURE:
<223> OTHER INFORMATION: Description of Artificial Sequence: Synthetic
      antisense oligonucleotide, can be RNA, DNA
      or chimera

<400> SEQUENCE: 81
tccctccckc cmccccmcct c                                             21
```

-continued

<210> SEQ ID NO 82
<211> LENGTH: 11
<212> TYPE: DNA
<213> ORGANISM: Artificial Sequence
<220> FEATURE:
<223> OTHER INFORMATION: Description of Combined DNA/RNA Molecule:
      Synthetic antisense oligonucleotide, can be
      RNA, DNA or chimera
<220> FEATURE:
<223> OTHER INFORMATION: Description of Artificial Sequence: Synthetic
      antisense oligonucleotide, can be RNA, DNA
      or chimera

<400> SEQUENCE: 82
tccctccctc c                                                              11

<210> SEQ ID NO 83
<211> LENGTH: 11
<212> TYPE: DNA
<213> ORGANISM: Artificial Sequence
<220> FEATURE:
<223> OTHER INFORMATION: Description of Combined DNA/RNA Molecule:
      Synthetic antisense oligonucleotide, can be
      RNA, DNA or chimera
<220> FEATURE:
<223> OTHER INFORMATION: Description of Artificial Sequence: Synthetic
      antisense oligonucleotide, can be RNA, DNA
      or chimera
<220> FEATURE:
<221> NAME/KEY: modified_base
<222> LOCATION: (2)..(3)
<223> OTHER INFORMATION: a purine base
<220> FEATURE:
<221> NAME/KEY: modified_base
<222> LOCATION: (5)
<223> OTHER INFORMATION: a, t, u, c, g, other or unknown
<220> FEATURE:
<221> NAME/KEY: modified_base
<222> LOCATION: (10)
<223> OTHER INFORMATION: a purine base
<220> FEATURE:
<221> NAME/KEY: modified_base
<222> LOCATION: (11)
<223> OTHER INFORMATION: a pyrimidine base

<400> SEQUENCE: 83
snnsngatwn n                                                              11

<210> SEQ ID NO 84
<211> LENGTH: 14
<212> TYPE: DNA
<213> ORGANISM: Homo sapiens

<400> SEQUENCE: 84
ctgggtatat cagg                                                           14

<210> SEQ ID NO 85
<211> LENGTH: 14
<212> TYPE: DNA
<213> ORGANISM: Artificial Sequence
<220> FEATURE:
<223> OTHER INFORMATION: Description of Combined DNA/RNA Molecule:
      Synthetic antisense oligonucleotide, can be
      RNA, DNA or chimera
<220> FEATURE:
<223> OTHER INFORMATION: Description of Artificial Sequence: Synthetic
      antisense oligonucleotide, can be RNA, DNA
      or chimera

<400> SEQUENCE: 85
ctgggtatat cagg                                                           14

```
<210> SEQ ID NO 86
<211> LENGTH: 14
<212> TYPE: DNA
<213> ORGANISM: Artificial Sequence
<220> FEATURE:
<223> OTHER INFORMATION: Description of Combined DNA/RNA Molecule:
      Synthetic antisense oligonucleotide, can be
      RNA, DNA or chimera
<220> FEATURE:
<223> OTHER INFORMATION: Description of Artificial Sequence: Synthetic
      antisense oligonucleotide, can be RNA, DNA
      or chimera

<400> SEQUENCE: 86
cctgatatac ccag                                                      14

<210> SEQ ID NO 87
<211> LENGTH: 12
<212> TYPE: DNA
<213> ORGANISM: Artificial Sequence
<220> FEATURE:
<223> OTHER INFORMATION: Description of Combined DNA/RNA Molecule:
      Synthetic antisense oligonucleotide, can be
      RNA, DNA or chimera
<220> FEATURE:
<223> OTHER INFORMATION: Description of Artificial Sequence: Synthetic
      antisense oligonucleotide, can be RNA, DNA
      or chimera

<400> SEQUENCE: 87
tgatataccc ag                                                        12

<210> SEQ ID NO 88
<211> LENGTH: 10
<212> TYPE: DNA
<213> ORGANISM: Homo sapiens

<400> SEQUENCE: 88
aggaaaagga                                                           10

<210> SEQ ID NO 89
<211> LENGTH: 9
<212> TYPE: DNA
<213> ORGANISM: Homo sapiens

<400> SEQUENCE: 89 ggaagaaga                                                             9

<210> SEQ ID NO 90
<211> LENGTH: 15
<212> TYPE: DNA
<213> ORGANISM: Homo sapiens

<400> SEQUENCE: 90
taaaaaaaaa aaaaa                                                     15

<210> SEQ ID NO 91
<211> LENGTH: 12
<212> TYPE: DNA
<213> ORGANISM: Homo sapiens

<400> SEQUENCE: 91
ggataaaggg ga                                                        12
```

```
<210> SEQ ID NO 92
<211> LENGTH: 18
<212> TYPE: DNA
<213> ORGANISM: Homo sapiens

<400> SEQUENCE: 92
aaacaaataa aagaaaa                                                  18

<210> SEQ ID NO 93
<211> LENGTH: 14
<212> TYPE: DNA
<213> ORGANISM: Homo sapiens

<400> SEQUENCE: 93
aaataaaaag aaaa                                                     14

<210> SEQ ID NO 94
<211> LENGTH: 11
<212> TYPE: DNA
<213> ORGANISM: Homo sapiens

<400> SEQUENCE: 94
ggagtaggag g                                                        11

<210> SEQ ID NO 95
<211> LENGTH: 17
<212> TYPE: DNA
<213> ORGANISM: Homo sapiens

<400> SEQUENCE: 95
aaaggaacag aacacag                                                  17

<210> SEQ ID NO 96
<211> LENGTH: 16
<212> TYPE: DNA
<213> ORGANISM: Homo sapiens

<400> SEQUENCE: 96
gaaagaggtg agaaag                                                   16

<210> SEQ ID NO 97
<211> LENGTH: 11
<212> TYPE: DNA
<213> ORGANISM: Homo sapiens

<400> SEQUENCE: 97
aaggaagggg g                                                        11

<210> SEQ ID NO 98
<211> LENGTH: 16
<212> TYPE: DNA
<213> ORGANISM: Homo sapiens

<400> SEQUENCE: 98
gagtgggaag ggaagg                                                   16

<210> SEQ ID NO 99
<211> LENGTH: 17
<212> TYPE: DNA
<213> ORGANISM: Homo sapiens

<400> SEQUENCE: 99
gagggatgag gagggag                                                  17
```

```
<210> SEQ ID NO 100
<211> LENGTH: 16
<212> TYPE: DNA
<213> ORGANISM: Homo sapiens

<400> SEQUENCE: 100
ggggaatggt tgagag                                                    16

<210> SEQ ID NO 101
<211> LENGTH: 12
<212> TYPE: DNA
<213> ORGANISM: Homo sapiens

<400> SEQUENCE: 101
aagaagagaa ta                                                        12

<210> SEQ ID NO 102
<211> LENGTH: 12
<212> TYPE: DNA
<213> ORGANISM: Homo sapiens

<400> SEQUENCE: 102
gggaggcgga gg                                                        12

<210> SEQ ID NO 103
<211> LENGTH: 26
<212> TYPE: DNA
<213> ORGANISM: Homo sapiens

<400> SEQUENCE: 103
aaaaaaaaaa agaaaaaaaa aaagag                                         26

<210> SEQ ID NO 104
<211> LENGTH: 14
<212> TYPE: DNA
<213> ORGANISM: Homo sapiens

<400> SEQUENCE: 104
aggggagggg gggg                                                      14

<210> SEQ ID NO 105
<211> LENGTH: 10
<212> TYPE: DNA
<213> ORGANISM: Homo sapiens

<400> SEQUENCE: 105
ggagggaatg                                                           10

<210> SEQ ID NO 106
<211> LENGTH: 11
<212> TYPE: DNA
<213> ORGANISM: Homo sapiens

<400> SEQUENCE: 106 tttcccctc t                                                          11

<210> SEQ ID NO 107
<211> LENGTH: 12
<212> TYPE: DNA
<213> ORGANISM: Homo sapiens

<400> SEQUENCE: 107
tttgctcttc tt                                                        12
```

```
<210> SEQ ID NO 108
<211> LENGTH: 21
<212> TYPE: DNA
<213> ORGANISM: Homo sapiens

<400> SEQUENCE: 108
ctccacccca ccgccctccc t                                     21

<210> SEQ ID NO 109
<211> LENGTH: 12
<212> TYPE: DNA
<213> ORGANISM: Homo sapiens

<400> SEQUENCE: 109
aagaggggga aa                                               12

<210> SEQ ID NO 110
<211> LENGTH: 12
<212> TYPE: DNA
<213> ORGANISM: Homo sapiens

<400> SEQUENCE: 110
aagaagagca aa                                               12

<210> SEQ ID NO 111
<211> LENGTH: 21
<212> TYPE: DNA
<213> ORGANISM: Homo sapiens

<400> SEQUENCE: 111
agggagggcg gtggggtgga g                                     21

<210> SEQ ID NO 112
<211> LENGTH: 18
<212> TYPE: DNA
<213> ORGANISM: Homo sapiens

<400> SEQUENCE: 112
tttttagtag agacaggg                                         18

<210> SEQ ID NO 113
<211> LENGTH: 18
<212> TYPE: DNA
<213> ORGANISM: Homo sapiens

<400> SEQUENCE: 113
aaagggtctt gtcccctc                                         18

<210> SEQ ID NO 114
<211> LENGTH: 23
<212> TYPE: DNA
<213> ORGANISM: Homo sapiens

<400> SEQUENCE: 114 tattttttt tttttttttt ttt                                    23

<210> SEQ ID NO 115
<211> LENGTH: 16
<212> TYPE: DNA
<213> ORGANISM: Homo sapiens

<400> SEQUENCE: 115
aaaaatttaa aaaatt                                           16
```

```
<210> SEQ ID NO 116
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic antisense oligonucleotide, can be
      RNA, DNA or chimera
<220> FEATURE:
<223> OTHER INFORMATION: Description of Artificial Sequence: Synthetic
      antisense oligonucleotide, can be RNA, DNA
      or chimera

<400> SEQUENCE: 116
aattcataat tctccttccc cat                                              23

<210> SEQ ID NO 117
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic antisense oligonucleotide, can be
      RNA, DNA or chimera
<220> FEATURE:
<223> OTHER INFORMATION: Description of Artificial Sequence: Synthetic
      antisense oligonucleotide, can be RNA, DNA
      or chimera

<400> SEQUENCE: 117
gugatataga taaggtaggg ugu                                              23

<210> SEQ ID NO 118
<211> LENGTH: 20
<212> TYPE: DNA
<213> ORGANISM: Artificial Sequence
<220> FEATURE:
<223> OTHER INFORMATION: Description of Combined DNA/RNA Molecule:
      Synthetic antisense oligonucleotide, can be
      RNA, DNA or chimera
<220> FEATURE:
<223> OTHER INFORMATION: Description of Artificial Sequence: Synthetic
      antisense oligonucleotide, can be RNA, DNA
      or chimera

<400> SEQUENCE: 118
gugatataga taaggtaggg                                                  20

<210> SEQ ID NO 119
<211> LENGTH: 18
<212> TYPE: DNA
<213> ORGANISM: Artificial Sequence
<220> FEATURE:
<223> OTHER INFORMATION: Description of Combined DNA/RNA Molecule:
      Synthetic antisense oligonucleotide, can be
      RNA, DNA or chimera
<220> FEATURE:
<223> OTHER INFORMATION: Description of Artificial Sequence: Synthetic
      antisense oligonucleotide, can be RNA, DNA
      or chimera

<400> SEQUENCE: 119
tgaaaatagg aataagca                                                    18

<210> SEQ ID NO 120
<211> LENGTH: 18
<212> TYPE: DNA
<213> ORGANISM: Artificial Sequence
```

```
<220> FEATURE:
<223> OTHER INFORMATION: Description of Combined DNA/RNA Molecule:
      Synthetic antisense oligonucleotide, can be
      RNA, DNA or chimera
<220> FEATURE:
<223> OTHER INFORMATION: Description of Artificial Sequence: Synthetic
      antisense oligonucleotide, can be RNA, DNA
      or chimera

<400> SEQUENCE: 120
agcagaacat gaggaatt                                                  18

<210> SEQ ID NO 121
<211> LENGTH: 20
<212> TYPE: DNA
<213> ORGANISM: Artificial Sequence
<220> FEATURE:
<223> OTHER INFORMATION: Description of Combined DNA/RNA Molecule:
      Synthetic antisense oligonucleotide, can be
      RNA, DNA or chimera
<220> FEATURE:
<223> OTHER INFORMATION: Description of Artificial Sequence: Synthetic
      antisense oligonucleotide, can be RNA, DNA
      or chimera

<400> SEQUENCE: 121
tcttctcgtt ttccacaccc                                                20

<210> SEQ ID NO 122
<211> LENGTH: 19
<212> TYPE: DNA
<213> ORGANISM: Artificial Sequence
<220> FEATURE:
<223> OTHER INFORMATION: Description of Combined DNA/RNA Molecule:
      Synthetic antisense oligonucleotide
<220> FEATURE:
<223> OTHER INFORMATION: Description of Artificial Sequence: Synthetic
      antisense oligonucleotide

<400> SEQUENCE: 122
cagggacaca gatggaaag                                                 19

<210> SEQ ID NO 123
<211> LENGTH: 24
<212> TYPE: DNA
<213> ORGANISM: Artificial Sequence
<220> FEATURE:
<223> OTHER INFORMATION: Description of Combined DNA/RNA Molecule:
      Synthetic antisense oligonucleotide, can be
      RNA, DNA or chimera
<220> FEATURE:
<223> OTHER INFORMATION: Description of Artificial Sequence: Synthetic
      antisense oligonucleotide, can be RNA, DNA
      or chimera

<400> SEQUENCE: 123
tgccagggac acagatggaa agat                                           24

<210> SEQ ID NO 124
<211> LENGTH: 18
<212> TYPE: DNA
<213> ORGANISM: Artificial Sequence
<220> FEATURE:
<223> OTHER INFORMATION: Description of Combined DNA/RNA Molecule:
      Synthetic antisense oligonucleotide, can be
      RNA, DNA or chimera
<220> FEATURE:
<223> OTHER INFORMATION: Description of Artificial Sequence: Synthetic
      antisense oligonucleotide, can be RNA, DNA
      or chimera
```

<400> SEQUENCE: 124 cattttagc agcatcgg                                                          18

<210> SEQ ID NO 125
<211> LENGTH: 16
<212> TYPE: DNA
<213> ORGANISM: Artificial Sequence
<220> FEATURE:
<223> OTHER INFORMATION: Description of Combined DNA/RNA Molecule:
      Synthetic antisense oligonucleotide, can be
      RNA, DNA or chimera
<220> FEATURE:
<223> OTHER INFORMATION: Description of Artificial Sequence: Synthetic
      antisense oligonucleotide, can be RNA, DNA
      or chimera
<220> FEATURE:
<223> OTHER INFORMATION: Description of Artificial Sequence: Synthetic
      oligonucleotide

<400> SEQUENCE: 125
cgaagttgtc atccag                                                           16

<210> SEQ ID NO 126
<211> LENGTH: 16
<212> TYPE: DNA
<213> ORGANISM: Artificial Sequence
<220> FEATURE:
<223> OTHER INFORMATION: Description of Combined DNA/RNA Molecule:
      Synthetic antisense oligonucleotide, can be
      RNA, DNA or chimera
<220> FEATURE:
<223> OTHER INFORMATION: Description of Artificial Sequence: Synthetic
      antisense oligonucleotide, can be RNA, DNA
      or chimera

<400> SEQUENCE: 126
ctaauaguag aguucc                                                           16

<210> SEQ ID NO 127
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic antisense oligonucleotide, can be
      RNA, DNA or chimera
<220> FEATURE:
<223> OTHER INFORMATION: Description of Artificial Sequence: Synthetic
      antisense oligonucleotide, can be RNA, DNA
      or chimera

<400> SEQUENCE: 127
tacaattcat aattctcctt c                                                     21

<210> SEQ ID NO 128
<211> LENGTH: 27
<212> TYPE: DNA
<213> ORGANISM: Artificial Sequence
<220> FEATURE:
<223> OTHER INFORMATION: Description of Combined DNA/RNA Molecule:
      Synthetic antisense oligonucleotide, can be
      RNA, DNA or chimera
<220> FEATURE:
<223> OTHER INFORMATION: Description of Artificial Sequence: Synthetic
      antisense oligonucleotide, can be RNA, DNA
      or chimera

<400> SEQUENCE: 128
ggtggctagg tgctctgccc tctttga                                               27

```
<210> SEQ ID NO 129
<211> LENGTH: 25
<212> TYPE: DNA
<213> ORGANISM: Artificial Sequence
<220> FEATURE:
<223> OTHER INFORMATION: Description of Combined DNA/RNA Molecule:
      Synthetic antisense oligonucleotide, can be
      RNA, DNA or chimera
<220> FEATURE:
<223> OTHER INFORMATION: Description of Artificial Sequence: Synthetic
      antisense oligonucleotide, can be RNA, DNA
      or chimera

<400> SEQUENCE: 129
tggctaggtg ctctgccctc tttga                                           25

<210> SEQ ID NO 130
<211> LENGTH: 24
<212> TYPE: DNA
<213> ORGANISM: Artificial Sequence
<220> FEATURE:
<223> OTHER INFORMATION: Description of Combined DNA/RNA Molecule:
      Synthetic antisense oligonucleotide, can be
      RNA, DNA or chimera
<220> FEATURE:
<223> OTHER INFORMATION: Description of Artificial Sequence: Synthetic
      antisense oligonucleotide, can be RNA, DNA
      or chimera

<400> SEQUENCE: 130
ttactgtgtg aagcaggcca tgaa                                            24

<210> SEQ ID NO 131
<211> LENGTH: 25
<212> TYPE: DNA
<213> ORGANISM: Artificial Sequence
<220> FEATURE:
<223> OTHER INFORMATION: Description of Combined DNA/RNA Molecule:
      Synthetic antisense oligonucleotide, can be
      RNA, DNA or chimera
<220> FEATURE:
<223> OTHER INFORMATION: Description of Artificial Sequence: Synthetic
      antisense oligonucleotide, can be RNA, DNA
      or chimera

<400> SEQUENCE: 131
tctgcacccc tcgtctcatg tacat                                           25

<210> SEQ ID NO 132
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic antisense oligonucleotide, can be
      RNA, DNA or chimera
<220> FEATURE:
<223> OTHER INFORMATION: Description of Artificial Sequence: Synthetic
      antisense oligonucleotide, can be RNA, DNA
      or chimera

<400> SEQUENCE: 132
gtcgtgtgca tgtatcgatt tct                                             23

<210> SEQ ID NO 133
<211> LENGTH: 24
<212> TYPE: DNA
<213> ORGANISM: Artificial Sequence
```

```
<220> FEATURE:
<223> OTHER INFORMATION: Description of Combined DNA/RNA Molecule:
      Synthetic antisense oligonucleotide, can be
      RNA, DNA or chimera
<220> FEATURE:
<223> OTHER INFORMATION: Description of Artificial Sequence: Synthetic
      antisense oligonucleotide, can be RNA, DNA
      or chimera

<400> SEQUENCE: 133
tgtatgtacc cctttattgc tcag                                            24

<210> SEQ ID NO 134
<211> LENGTH: 14
<212> TYPE: DNA
<213> ORGANISM: Artificial Sequence
<220> FEATURE:
<223> OTHER INFORMATION: Description of Combined DNA/RNA Molecule:
      Synthetic antisense oligonucleotide, can be
      RNA, DNA or chimera
<220> FEATURE:
<223> OTHER INFORMATION: Description of Artificial Sequence: Synthetic
      antisense oligonucleotide, can be RNA, DNA
      or chimera

<400> SEQUENCE: 134
gggagtggga ggag                                                       14

<210> SEQ ID NO 135
<211> LENGTH: 18
<212> TYPE: DNA
<213> ORGANISM: Artificial Sequence
<220> FEATURE:
<223> OTHER INFORMATION: Description of Combined DNA/RNA Molecule:
      Synthetic antisense oligonucleotide, can be
      RNA, DNA or chimera
<220> FEATURE:
<223> OTHER INFORMATION: Description of Artificial Sequence: Synthetic
      antisense oligonucleotide, can be RNA, DNA
      or chimera

<400> SEQUENCE: 135
tgtgccattg ggctccat                                                   18

<210> SEQ ID NO 136
<211> LENGTH: 20
<212> TYPE: DNA
<213> ORGANISM: Artificial Sequence
<220> FEATURE:
<223> OTHER INFORMATION: Description of Combined DNA/RNA Molecule:
      Synthetic antisense oligonucleotide, can be
      RNA, DNA or chimera
<220> FEATURE:
<223> OTHER INFORMATION: Description of Artificial Sequence: Synthetic
      antisense oligonucleotide, can be RNA, DNA
      or chimera

<400> SEQUENCE: 136
tgaggaaaaa aagtggaggg                                                 20

<210> SEQ ID NO 137
<211> LENGTH: 19
<212> TYPE: DNA
<213> ORGANISM: Artificial Sequence
<220> FEATURE:
<223> OTHER INFORMATION: Description of Combined DNA/RNA Molecule:
      Synthetic antisense oligonucleotide, can be
      RNA, DNA or chimera
```

```
<220> FEATURE:
<223> OTHER INFORMATION: Description of Artificial Sequence: Synthetic
      antisense oligonucleotide, can be RNA, DNA
      or chimera

<400> SEQUENCE: 137
taaaggcaag ttgggaag                                              19

<210> SEQ ID NO 138
<211> LENGTH: 25
<212> TYPE: DNA
<213> ORGANISM: Artificial Sequence
<220> FEATURE:
<223> OTHER INFORMATION: Description of Combined DNA/RNA Molecule:
      Synthetic antisense oligonucleotide, can be
      RNA, DNA or chimera
<220> FEATURE:
<223> OTHER INFORMATION: Description of Artificial Sequence: Synthetic
      antisense oligonucleotide, can be RNA, DNA
      or chimera

<400> SEQUENCE: 138
gtgatgagga tgagccgtgg taacc                                      25

<210> SEQ ID NO 139
<211> LENGTH: 18
<212> TYPE: DNA
<213> ORGANISM: Artificial Sequence
<220> FEATURE:
<223> OTHER INFORMATION: Description of Combined DNA/RNA Molecule:
      Synthetic antisense oligonucleotide, can be
      RNA, DNA or chimera
<220> FEATURE:
<223> OTHER INFORMATION: Description of Artificial Sequence: Synthetic
      antisense oligonucleotide, can be RNA, DNA
      or chimera

<400> SEQUENCE: 139
aatggcagag aagggcag                                              18

<210> SEQ ID NO 140
<211> LENGTH: 18
<212> TYPE: DNA
<213> ORGANISM: Artificial Sequence
<220> FEATURE:
<223> OTHER INFORMATION: Description of Combined DNA/RNA Molecule:
      Synthetic antisense oligonucleotide, can be
      RNA, DNA or chimera
<220> FEATURE:
<223> OTHER INFORMATION: Description of Artificial Sequence: Synthetic
      antisense oligonucleotide, can be RNA, DNA
      or chimera

<400> SEQUENCE: 140
ctaggaatgg tcttagca                                              18

<210> SEQ ID NO 141
<211> LENGTH: 18
<212> TYPE: DNA
<213> ORGANISM: Artificial Sequence
<220> FEATURE:
<223> OTHER INFORMATION: Description of Combined DNA/RNA Molecule:
      Synthetic antisense oligonucleotide, can be
      RNA, DNA or chimera
<220> FEATURE:
<223> OTHER INFORMATION: Description of Artificial Sequence: Synthetic
      antisense oligonucleotide, can be RNA, DNA
      or chimera
```

```
-continued
<400> SEQUENCE: 141
aatggcagag aagggcag                                                    18

<210> SEQ ID NO 142
<211> LENGTH: 18
<212> TYPE: DNA
<213> ORGANISM: Artificial Sequence
<220> FEATURE:
<223> OTHER INFORMATION: Description of Combined DNA/RNA Molecule:
      Synthetic antisense oligonucleotide, can be
      RNA, DNA or chimera
<220> FEATURE:
<223> OTHER INFORMATION: Description of Artificial Sequence: Synthetic
      antisense oligonucleotide, can be RNA, DNA
      or chimera

<400> SEQUENCE: 142
tgtgccattg ggtgccat                                                    18

<210> SEQ ID NO 143
<211> LENGTH: 7
<212> TYPE: PRT
<213> ORGANISM: Artificial Sequence
<220> FEATURE:
<223> OTHER INFORMATION: Description of Artificial Sequence: ATPase
      consensus sequence
<220> FEATURE:
<221> NAME/KEY: MOD_RES
<222> LOCATION: (1)
<223> OTHER INFORMATION: Phosphorylated

<400> SEQUENCE: 143

Asp Lys Thr Gly Thr Leu Thr
 1               5
```